(12) United States Patent
Stone et al.

(10) Patent No.: US 9,357,992 B2
(45) Date of Patent: *Jun. 7, 2016

(54) METHOD FOR COUPLING SOFT TISSUE TO A BONE

(71) Applicant: Biomet Sports Medicine, LLC, Warsaw, IN (US)

(72) Inventors: Kevin T. Stone, Winona Lake, IN (US); Gregory J. Denham, Warsaw, IN (US); Daniel Norton, Winona Lake, IN (US)

(73) Assignee: BIOMET SPORTS MEDICINE, LLC, Warsaw, IN (US)

(*) Notice: Subject to any disclaimer, the term of this patent is extended or adjusted under 35 U.S.C. 154(b) by 424 days.

This patent is subject to a terminal disclaimer.

(21) Appl. No.: 13/757,003

(22) Filed: Feb. 1, 2013

(65) Prior Publication Data

US 2013/0144337 A1    Jun. 6, 2013

Related U.S. Application Data

(63) Continuation-in-part of application No. 13/293,825, filed on Nov. 10, 2011, now Pat. No. 9,149,267.

(51) Int. Cl.
*A61B 17/04* (2006.01)
*A61B 17/00* (2006.01)
(Continued)

(52) U.S. Cl.
CPC .......... *A61B 17/0401* (2013.01); *A61B 17/0482* (2013.01); *A61B 17/0485* (2013.01); *A61B 17/1684* (2013.01); *A61B 2017/00336* (2013.01);
(Continued)

(58) Field of Classification Search
CPC ........... A61B 17/0401; A61B 17/0487; A61B 17/06166; A61B 2017/0414; A61B 2017/0458; A61B 2017/06185; A61F 2002/0852; D04C 1/12

See application file for complete search history.

(56) References Cited

U.S. PATENT DOCUMENTS

| 65,499 A | 6/1867 | Miller |
|---|---|---|
| 126,366 A | 4/1872 | Wills |

(Continued)

FOREIGN PATENT DOCUMENTS

| AU | 4957264 | 3/1966 |
|---|---|---|
| AU | 440266 | 10/1967 |

(Continued)

OTHER PUBLICATIONS

International Preliminary Report on Patentability and Written Opinion mailed Nov. 28, 2013 for PCT/US2012/037703, which claims benefit of U.S. Appl. No. 13/109,672, filed May 17, 2011, and U.S. Appl. No. 13/109,667, filed May 17, 2011.

(Continued)

*Primary Examiner* — Dianne Dornbusch
(74) *Attorney, Agent, or Firm* — Schwegman Lundberg & Woessner, P.A.

(57) ABSTRACT

A method for coupling tissue with a flexible member including a tail and a self-locking construct coupled to the tail. The self-locking construct includes a first loop and an adjustable second loop coupled thereto. The method includes implanting an anchor in bone. The anchor is slidably mounted to the tail. The tail is positioned relative to the tissue. An end of the tail is inserted through the first loop. The tail is passed through the first loop. The second loop is pulled into the anchor. The self-locking construct is positioned relative to the tissue. The self-locking construct is tightened against the tissue by pulling on an end of the self-locking construct.

19 Claims, 40 Drawing Sheets

(51) Int. Cl.
*A61B 17/06* (2006.01)
*A61B 17/16* (2006.01)

(52) U.S. Cl.
CPC ............... *A61B 2017/00858* (2013.01); *A61B 2017/0406* (2013.01); *A61B 2017/0409* (2013.01); *A61B 2017/0417* (2013.01); *A61B 2017/0445* (2013.01); *A61B 2017/0458* (2013.01); *A61B 2017/0464* (2013.01); *A61B 2017/0477* (2013.01); *A61B 2017/06185* (2013.01)

(56) References Cited

U.S. PATENT DOCUMENTS

| | | |
|---|---|---|
| 233,475 A | 10/1880 | Cook et al. |
| 261,501 A | 7/1882 | Vandermark |
| 268,407 A | 12/1882 | Hughes |
| 330,087 A | 11/1885 | Binns |
| 394,739 A | 12/1888 | Toulmin |
| 401,677 A | 4/1889 | Autenrieth |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| 2,397,216 A | 3/1946 | Stellin |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,081,781 A | 3/1963 | Stermer |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Himmelstein et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett |
| 3,976,079 A | 8/1976 | Samuels et al. |
| 3,977,050 A | 8/1976 | Perez |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |

(56) References Cited

U.S. PATENT DOCUMENTS

| | | | |
|---|---|---|---|
| 4,013,071 | A | 3/1977 | Rosenberg et al. |
| 4,026,281 | A | 5/1977 | Mayberry et al. |
| 4,036,101 | A | 7/1977 | Burnett |
| 4,050,100 | A | 9/1977 | Barry |
| 4,054,954 | A | 10/1977 | Nakayama et al. |
| 4,084,478 | A | 4/1978 | Simmons |
| 4,085,466 | A | 4/1978 | Goodfellow et al. |
| 4,094,313 | A | 6/1978 | Komamura et al. |
| 4,099,750 | A | 7/1978 | McGrew |
| 4,103,690 | A | 8/1978 | Harris |
| RE29,819 | E | 10/1978 | Bone |
| 4,121,487 | A | 10/1978 | Bone |
| 4,143,656 | A | 3/1979 | Holmes |
| 4,144,876 | A | 3/1979 | DeLeo |
| 4,146,022 | A | 3/1979 | Johnson et al. |
| 4,149,277 | A | 4/1979 | Bokros |
| 4,157,714 | A | 6/1979 | Foltz et al. |
| 4,158,250 | A | 6/1979 | Ringwald |
| 4,160,453 | A | 7/1979 | Miller |
| 4,164,225 | A | 8/1979 | Johnson et al. |
| 4,172,458 | A | 10/1979 | Pereyra |
| 4,175,555 | A | 11/1979 | Herbert et al. |
| 4,185,636 | A | 1/1980 | Gabbay et al. |
| 4,196,883 | A | 4/1980 | Einhorn et al. |
| 4,210,148 | A | 7/1980 | Stivala |
| 4,235,161 | A | 11/1980 | Kunreuther |
| 4,235,238 | A | 11/1980 | Ogiu et al. |
| 4,237,779 | A | 12/1980 | Kunreuther |
| 4,243,037 | A | 1/1981 | Smith |
| 4,249,525 | A | 2/1981 | Krzeminski |
| 4,263,913 | A | 4/1981 | Malmin |
| 4,265,246 | A | 5/1981 | Barry |
| 4,273,117 | A | 6/1981 | Neuhauser et al. |
| 4,275,490 | A | 6/1981 | Bivins |
| 4,275,717 | A | 6/1981 | Bolesky |
| 4,287,807 | A | 9/1981 | Pacharis et al. |
| 4,291,698 | A | 9/1981 | Fuchs et al. |
| 4,301,551 | A | 11/1981 | Dore et al. |
| 4,307,723 | A | 12/1981 | Finney |
| 4,312,337 | A | 1/1982 | Donohue |
| 4,316,469 | A | 2/1982 | Kapitanov et al. |
| 4,326,531 | A | 4/1982 | Shimonaka et al. |
| 4,345,601 | A | 8/1982 | Fukuda |
| 4,349,027 | A | 9/1982 | DiFrancesco |
| 4,388,921 | A | 6/1983 | Sutter et al. |
| 4,400,833 | A | 8/1983 | Kurland |
| 4,402,445 | A | 9/1983 | Green |
| 4,409,974 | A | 10/1983 | Freedland |
| 4,438,769 | A | 3/1984 | Pratt et al. |
| 4,441,489 | A | 4/1984 | Evans et al. |
| 4,454,875 | A | 6/1984 | Pratt et al. |
| 4,462,395 | A | 7/1984 | Johnson |
| 4,463,753 | A | 8/1984 | Gustilo |
| 4,473,102 | A | 9/1984 | Ohman et al. |
| 4,484,570 | A | 11/1984 | Sutter et al. |
| 4,489,446 | A | 12/1984 | Reed |
| 4,489,464 | A | 12/1984 | Massari et al. |
| 4,493,323 | A | 1/1985 | Albright et al. |
| 4,496,468 | A | 1/1985 | House et al. |
| 4,505,274 | A | 3/1985 | Speelman |
| 4,509,516 | A | 4/1985 | Richmond |
| 4,531,522 | A | 7/1985 | Bedi et al. |
| 4,532,926 | A | 8/1985 | O'Holla |
| 4,534,350 | A | 8/1985 | Golden et al. |
| 4,535,764 | A | 8/1985 | Ebert |
| 4,537,185 | A | 8/1985 | Stednitz |
| 4,549,545 | A | 10/1985 | Levy |
| 4,549,652 | A | 10/1985 | Free |
| 4,561,432 | A | 12/1985 | Mazor |
| 4,564,007 | A | 1/1986 | Coombs et al. |
| 4,570,623 | A | 2/1986 | Ellison et al. |
| 4,573,844 | A | 3/1986 | Smith |
| 4,576,608 | A | 3/1986 | Homsy |
| 4,584,722 | A | 4/1986 | Levy et al. |
| 4,587,963 | A | 5/1986 | Leibinger et al. |
| 4,590,928 | A | 5/1986 | Hunt et al. |
| 4,595,007 | A | 6/1986 | Mericle |
| 4,596,249 | A | 6/1986 | Freda et al. |
| 4,602,635 | A | 7/1986 | Mulhollan et al. |
| 4,602,636 | A | 7/1986 | Noiles |
| 4,604,997 | A | 8/1986 | De Bastiani et al. |
| 4,605,414 | A | 8/1986 | Czajka |
| 4,616,650 | A | 10/1986 | Green et al. |
| 4,621,640 | A | 11/1986 | Mulhollan et al. |
| 4,624,254 | A | 11/1986 | McGarry et al. |
| 4,632,100 | A | 12/1986 | Somers et al. |
| 4,635,637 | A | 1/1987 | Schreiber |
| 4,636,121 | A | 1/1987 | Miller |
| 4,641,652 | A | 2/1987 | Hutterer et al. |
| 4,649,916 | A | 3/1987 | Frimberger |
| 4,649,952 | A | 3/1987 | Jobe |
| 4,653,486 | A | 3/1987 | Coker |
| 4,653,487 | A | 3/1987 | Maale |
| 4,653,489 | A | 3/1987 | Tronzo |
| 4,655,777 | A | 4/1987 | Dunn et al. |
| 4,662,068 | A | 5/1987 | Polonsky |
| 4,667,662 | A | 5/1987 | Titone et al. |
| 4,667,675 | A | 5/1987 | Davis |
| 4,669,473 | A | 6/1987 | Richards et al. |
| 4,683,895 | A | 8/1987 | Pohndorf |
| 4,688,561 | A | 8/1987 | Reese |
| 4,690,169 | A | 9/1987 | Jobe |
| 4,696,300 | A | 9/1987 | Anderson |
| 4,705,040 | A | 11/1987 | Mueller et al. |
| 4,708,132 | A | 11/1987 | Silvestrini |
| 4,714,475 | A | 12/1987 | Grundei et al. |
| 4,716,893 | A | 1/1988 | Fischer et al. |
| 4,719,671 | A | 1/1988 | Ito et al. |
| 4,719,917 | A | 1/1988 | Barrows et al. |
| 4,723,540 | A | 2/1988 | Gilmer, Jr. |
| 4,724,839 | A | 2/1988 | Bedi et al. |
| 4,728,332 | A | 3/1988 | Albrektsson |
| 4,738,255 | A | 4/1988 | Goble et al. |
| 4,739,751 | A | 4/1988 | Sapega et al. |
| 4,741,330 | A | 5/1988 | Hayhurst |
| 4,741,336 | A | 5/1988 | Failla et al. |
| 4,744,353 | A | 5/1988 | McFarland |
| 4,744,793 | A | 5/1988 | Parr et al. |
| 4,750,492 | A | 6/1988 | Jacobs |
| 4,760,843 | A | 8/1988 | Fischer et al. |
| 4,760,844 | A | 8/1988 | Kyle |
| 4,760,848 | A | 8/1988 | Hasson |
| 4,770,663 | A | 9/1988 | Hanslik et al. |
| 4,772,261 | A | 9/1988 | Von Hoff et al. |
| 4,772,286 | A | 9/1988 | Goble et al. |
| 4,773,910 | A | 9/1988 | Chen et al. |
| 4,775,380 | A | 10/1988 | Seedhom et al. |
| 4,776,328 | A | 10/1988 | Frey et al. |
| 4,781,190 | A | 11/1988 | Lee et al. |
| 4,784,126 | A | 11/1988 | Hourahane |
| 4,787,882 | A | 11/1988 | Claren et al. |
| 4,790,297 | A | 12/1988 | Luque et al. |
| 4,793,363 | A | 12/1988 | Ausherman et al. |
| 4,809,695 | A | 3/1989 | Gwathmey et al. |
| 4,813,406 | A | 3/1989 | Ogle, II |
| 4,823,794 | A | 4/1989 | Pierce |
| 4,828,562 | A | 5/1989 | Kenna |
| 4,832,026 | A | 5/1989 | Jones |
| 4,834,098 | A | 5/1989 | Jones |
| 4,838,282 | A | 6/1989 | Strasser et al. |
| 4,841,960 | A | 6/1989 | Garner |
| 4,851,005 | A | 7/1989 | Hunt et al. |
| 4,858,608 | A | 8/1989 | McQuilkin et al. |
| 4,860,513 | A | 8/1989 | Whitman |
| 4,863,383 | A | 9/1989 | Grafelmann et al. |
| 4,870,957 | A | 10/1989 | Goble et al. |
| 4,873,976 | A | 10/1989 | Schreiber |
| 4,887,601 | A | 12/1989 | Richards |
| 4,889,110 | A | 12/1989 | Galline et al. |
| 4,890,615 | A | 1/1990 | Caspari et al. |
| 4,893,619 | A | 1/1990 | Dale et al. |
| 4,893,974 | A | 1/1990 | Fischer et al. |
| 4,895,148 | A | 1/1990 | Bays et al. |
| 4,896,668 | A | 1/1990 | Popoff et al. |

(56) References Cited

U.S. PATENT DOCUMENTS

| | | | |
|---|---|---|---|
| 4,898,156 A | 2/1990 | Gatturna et al. | |
| 4,899,743 A | 2/1990 | Nicholson et al. | |
| 4,901,721 A | 2/1990 | Hakki | |
| 4,922,897 A | 5/1990 | Sapega et al. | |
| 4,923,461 A | 5/1990 | Caspari et al. | |
| 4,927,421 A | 5/1990 | Goble et al. | |
| 4,946,377 A | 8/1990 | Kovach | |
| 4,946,468 A | 8/1990 | Li | |
| 4,950,270 A | 8/1990 | Bowman et al. | |
| 4,950,285 A | 8/1990 | Wilk | |
| 4,960,381 A | 10/1990 | Niznick | |
| 4,961,741 A | 10/1990 | Hayhurst | |
| 4,968,315 A | 11/1990 | Gatturna | |
| 4,968,317 A | 11/1990 | Tormala et al. | |
| 4,969,886 A | 11/1990 | Cziffer et al. | |
| 4,974,488 A * | 12/1990 | Spralja | 87/8 |
| 4,976,736 A | 12/1990 | White et al. | |
| 4,978,350 A | 12/1990 | Wagenknecht et al. | |
| 4,979,956 A | 12/1990 | Silvestrini | |
| 4,983,176 A | 1/1991 | Cushman et al. | |
| 4,988,351 A | 1/1991 | Paulos et al. | |
| 4,994,074 A | 2/1991 | Bezwada et al. | |
| 4,997,433 A | 3/1991 | Goble et al. | |
| 5,002,550 A | 3/1991 | Li | |
| 5,002,562 A | 3/1991 | Oberlander | |
| 5,002,574 A | 3/1991 | May et al. | |
| 5,007,921 A | 4/1991 | Brown | |
| 5,030,224 A | 7/1991 | Wright et al. | |
| 5,030,235 A | 7/1991 | Campbell, Jr. | |
| 5,035,701 A | 7/1991 | Kabbara | |
| 5,037,422 A | 8/1991 | Hayhurst et al. | |
| 5,037,426 A | 8/1991 | Goble et al. | |
| 5,041,129 A | 8/1991 | Hayhurst et al. | |
| 5,046,513 A | 9/1991 | Gatturna et al. | |
| 5,047,030 A | 9/1991 | Draenert et al. | |
| 5,053,046 A | 10/1991 | Janese | |
| 5,053,047 A | 10/1991 | Yoon | |
| 5,059,201 A | 10/1991 | Asnis | |
| 5,059,206 A | 10/1991 | Winters | |
| 5,061,277 A | 10/1991 | Carpentier et al. | |
| 5,062,344 A * | 11/1991 | Gerker | 87/8 |
| 5,062,843 A | 11/1991 | Mahony, III | |
| 5,064,431 A | 11/1991 | Gilbertson et al. | |
| 5,071,420 A | 12/1991 | Paulos et al. | |
| 5,074,874 A | 12/1991 | Yoon et al. | |
| 5,078,731 A | 1/1992 | Hayhurst | |
| 5,078,843 A | 1/1992 | Pratt | |
| 5,084,050 A | 1/1992 | Draenert | |
| 5,084,058 A | 1/1992 | Li | |
| 5,085,661 A | 2/1992 | Moss | |
| 5,087,263 A | 2/1992 | Li | |
| 5,087,309 A | 2/1992 | Melton, Jr. | |
| 5,089,012 A | 2/1992 | Prou | |
| 5,092,866 A | 3/1992 | Breard et al. | |
| 5,098,435 A | 3/1992 | Stednitz et al. | |
| 5,100,415 A | 3/1992 | Hayhurst | |
| 5,100,417 A | 3/1992 | Cerier et al. | |
| 5,108,433 A | 4/1992 | May et al. | |
| 5,116,337 A | 5/1992 | Johnson | |
| 5,116,373 A | 5/1992 | Jakob et al. | |
| 5,116,375 A | 5/1992 | Hofmann | |
| 5,123,913 A | 6/1992 | Wilk et al. | |
| 5,123,914 A | 6/1992 | Cope | |
| 5,127,785 A | 7/1992 | Faucher et al. | |
| 5,129,901 A | 7/1992 | Decoste | |
| 5,129,902 A | 7/1992 | Goble et al. | |
| 5,129,904 A | 7/1992 | Illi et al. | |
| 5,129,906 A | 7/1992 | Ross et al. | |
| 5,139,498 A | 8/1992 | Astudillo Ley | |
| 5,139,499 A | 8/1992 | Small et al. | |
| 5,139,520 A | 8/1992 | Rosenberg | |
| 5,143,498 A | 9/1992 | Whitman | |
| 5,147,362 A | 9/1992 | Goble | |
| 5,149,329 A | 9/1992 | Richardson | |
| 5,151,104 A | 9/1992 | Kenna | |
| 5,152,790 A | 10/1992 | Rosenberg et al. | |
| 5,154,189 A | 10/1992 | Oberlander | |
| 5,156,616 A | 10/1992 | Meadows et al. | |
| 5,163,960 A | 11/1992 | Bonutti | |
| D331,626 S | 12/1992 | Hayhurst et al. | |
| 5,169,400 A | 12/1992 | Muhling et al. | |
| 5,176,682 A | 1/1993 | Chow | |
| 5,178,629 A | 1/1993 | Kammerer | |
| 5,183,458 A | 2/1993 | Marx | |
| 5,190,545 A | 3/1993 | Corsi et al. | |
| 5,192,282 A | 3/1993 | Draenert et al. | |
| 5,197,987 A | 3/1993 | Koch et al. | |
| 5,199,135 A | 4/1993 | Gold | |
| 5,203,784 A | 4/1993 | Ross et al. | |
| 5,203,787 A | 4/1993 | Noblitt et al. | |
| 5,207,679 A | 5/1993 | Li | |
| 5,209,753 A | 5/1993 | Biedermann et al. | |
| 5,209,805 A | 5/1993 | Spraggins | |
| 5,211,647 A | 5/1993 | Schmieding | |
| 5,211,650 A | 5/1993 | Noda | |
| 5,214,987 A | 6/1993 | Fenton, Sr. | |
| 5,219,359 A | 6/1993 | McQuilkin et al. | |
| 5,222,976 A | 6/1993 | Yoon | |
| 5,224,946 A | 7/1993 | Hayhurst et al. | |
| 5,230,699 A | 7/1993 | Grasinger | |
| 5,232,436 A | 8/1993 | Janevski | |
| 5,234,435 A | 8/1993 | Seagrave, Jr. | |
| 5,235,238 A | 8/1993 | Nomura et al. | |
| 5,236,445 A | 8/1993 | Hayhurst et al. | |
| 5,236,461 A | 8/1993 | Forte | |
| 5,242,447 A | 9/1993 | Borzone | |
| 5,246,441 A | 9/1993 | Ross et al. | |
| 5,249,899 A | 10/1993 | Wilson | |
| 5,250,053 A | 10/1993 | Snyder | |
| 5,258,015 A | 11/1993 | Li et al. | |
| 5,258,016 A | 11/1993 | DiPoto et al. | |
| 5,258,040 A | 11/1993 | Bruchman et al. | |
| 5,261,908 A | 11/1993 | Campbell, Jr. | |
| 5,268,001 A | 12/1993 | Nicholson et al. | |
| 5,269,160 A | 12/1993 | Wood | |
| 5,269,783 A | 12/1993 | Sander | |
| 5,269,806 A | 12/1993 | Sardelis et al. | |
| 5,269,809 A | 12/1993 | Hayhurst et al. | |
| 5,279,311 A | 1/1994 | Snyder | |
| 5,281,422 A | 1/1994 | Badylak et al. | |
| 5,282,809 A | 2/1994 | Kammerer et al. | |
| 5,282,832 A | 2/1994 | Toso et al. | |
| 5,282,867 A | 2/1994 | Mikhail | |
| 5,285,040 A | 2/1994 | Brandberg et al. | |
| 5,290,217 A | 3/1994 | Campos | |
| 5,290,243 A | 3/1994 | Chodorow et al. | |
| 5,306,301 A | 4/1994 | Graf et al. | |
| 5,312,410 A | 5/1994 | Miller et al. | |
| 5,312,422 A | 5/1994 | Trott | |
| 5,312,438 A | 5/1994 | Johnson | |
| 5,314,429 A | 5/1994 | Goble | |
| 5,318,566 A | 6/1994 | Miller | |
| 5,318,575 A | 6/1994 | Chesterfield et al. | |
| 5,318,577 A | 6/1994 | Li | |
| 5,318,578 A | 6/1994 | Hasson | |
| 5,320,115 A | 6/1994 | Kenna | |
| 5,320,626 A | 6/1994 | Schmieding | |
| 5,320,633 A | 6/1994 | Allen et al. | |
| 5,324,308 A | 6/1994 | Pierce | |
| 5,330,489 A | 7/1994 | Green et al. | |
| 5,333,625 A | 8/1994 | Klein | |
| 5,334,204 A | 8/1994 | Clewett et al. | |
| 5,336,229 A | 8/1994 | Noda | |
| 5,336,231 A | 8/1994 | Adair | |
| 5,336,240 A | 8/1994 | Metzler et al. | |
| 5,339,870 A | 8/1994 | Green et al. | |
| 5,342,369 A | 8/1994 | Harryman, II | |
| 5,346,462 A | 9/1994 | Barber | |
| 5,350,380 A | 9/1994 | Goble et al. | |
| RE34,762 E | 10/1994 | Goble et al. | |
| 5,354,292 A | 10/1994 | Braeuer et al. | |
| 5,354,298 A | 10/1994 | Lee et al. | |
| 5,356,412 A | 10/1994 | Golds et al. | |
| 5,356,413 A | 10/1994 | Martins et al. | |

(56) References Cited

U.S. PATENT DOCUMENTS

| | | |
|---|---|---|
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,690 A | 5/1995 | Sennett et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,613,971 A | 3/1997 | Lower et al. |
| 5,618,290 A | 4/1997 | Toy et al. |
| 5,626,611 A | 5/1997 | Liu et al. |

(56) References Cited

U.S. PATENT DOCUMENTS

| | | |
|---|---|---|
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A * | 12/1997 | Paulson .......................... 57/22 |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,581 A | 3/1998 | Br.ang.nemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,814,056 A | 9/1998 | Prosst et al. |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,973 A | 1/1999 | Michelson |
| 5,860,978 A | 1/1999 | McDevitt et al. |
| 5,868,740 A | 2/1999 | LeVeen et al. |
| 5,868,748 A | 2/1999 | Burke |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,133 A | 8/1999 | Wagner et al. |
| 5,935,149 A | 8/1999 | Ek |

(56) References Cited

U.S. PATENT DOCUMENTS

| | | |
|---|---|---|
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,520 A | 10/1999 | Beck, Jr. et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |

(56) References Cited

U.S. PATENT DOCUMENTS

| | | |
|---|---|---|
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,543,094 B2 | 4/2003 | D'Addario |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B2 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues |
| 6,626,919 B1 | 9/2003 | Swanstrom |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,211 B2 | 11/2003 | Magana |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |

(56) References Cited

U.S. PATENT DOCUMENTS

| | | |
|---|---|---|
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,793,595 B1 | 9/2004 | Monnet |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,719 B2 | 2/2006 | Grafton |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris et al. |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,201,722 B2 | 4/2007 | Krueger |
| 7,207,993 B1 | 4/2007 | Baldwin et al. |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,494,506 B2 | 2/2009 | Brulez et al. |
| D587,807 S | 3/2009 | Wolf et al. |
| 7,500,983 B1 | 3/2009 | Kaiser et al. |
| 7,513,910 B2 | 4/2009 | Buskirk et al. |
| 7,572,298 B2 | 8/2009 | Roller et al. |
| 7,578,825 B2 | 8/2009 | Huebner |
| 7,585,311 B2 | 9/2009 | Green et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,695,503 B1 | 4/2010 | Kaiser et al. |
| 7,717,929 B2 | 5/2010 | Fallman |
| 7,731,732 B2 | 6/2010 | Ken |
| 7,736,364 B2 | 6/2010 | Stone |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,776,041 B1 | 8/2010 | Walters |
| 7,803,173 B2 | 9/2010 | Burkhart et al. |
| 7,819,895 B2 | 10/2010 | Ginn et al. |
| 7,828,820 B2 | 11/2010 | Stone et al. |
| 7,828,850 B2 | 11/2010 | Cauthen, III et al. |
| 7,856,698 B2 | 12/2010 | Hays |
| 7,857,830 B2 | 12/2010 | Stone et al. |

(56) References Cited

U.S. PATENT DOCUMENTS

| | | |
|---|---|---|
| 7,867,264 B2 | 1/2011 | McDevitt et al. |
| 7,875,058 B2 | 1/2011 | Holmes, Jr. |
| 7,878,058 B2 | 2/2011 | Blendinger et al. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,128,658 B2 | 3/2012 | Kaiser et al. |
| 8,137,354 B2 | 3/2012 | Stone |
| 8,137,382 B2 | 3/2012 | Denham et al. |
| 8,162,997 B2 | 4/2012 | Struhl |
| 8,167,906 B2 | 5/2012 | Cauldwell et al. |
| 8,202,318 B2 | 6/2012 | Willobee |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,298,284 B2 | 10/2012 | Cassani |
| 8,303,604 B2 | 11/2012 | Stone et al. |
| 8,317,825 B2 | 11/2012 | Stone |
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,113 B2 | 1/2013 | Stone et al. |
| 8,409,253 B2 | 4/2013 | Stone et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 | 2/2014 | Denham et al. |
| 8,672,968 B2 | 3/2014 | Stone et al. |
| 8,672,969 B2 | 3/2014 | Stone et al. |
| 8,721,650 B2 | 5/2014 | Fanton et al. |
| 8,721,684 B2 | 5/2014 | Denham et al. |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,840,645 B2 | 9/2014 | Denham et al. |
| 8,900,314 B2 | 12/2014 | Metzger et al. |
| 8,932,331 B2 | 1/2015 | Kaiser et al. |
| 8,936,621 B2 | 1/2015 | Denham et al. |
| 8,968,364 B2 | 3/2015 | Berelsman et al. |
| 8,998,949 B2 | 4/2015 | Stone et al. |
| 9,005,287 B2 | 4/2015 | Stone |
| 9,017,381 B2 | 4/2015 | Kaiser et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |

(56) References Cited

U.S. PATENT DOCUMENTS

| | | |
|---|---|---|
| 2003/0208210 A1 | 11/2003 | Dreyfuss et al. |
| 2003/0212456 A1 | 11/2003 | Lipchitz et al. |
| 2003/0216809 A1 | 11/2003 | Ferguson |
| 2003/0220660 A1 | 11/2003 | Kortenbach et al. |
| 2003/0225459 A1 | 12/2003 | Hammer et al. |
| 2003/0229396 A1 | 12/2003 | Andrews |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1* | 10/2004 | Sikora et al. ................. 606/151 |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267361 A1 | 12/2004 | Donnelly et al. |
| 2004/0267362 A1 | 12/2004 | Hwang et al. |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1* | 6/2005 | Fallman ................. 606/213 |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |

(56) References Cited

U.S. PATENT DOCUMENTS

| | | |
|---|---|---|
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0212055 A1 | 9/2006 | Karabey et al. |
| 2006/0229671 A1 | 10/2006 | Steiner et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0071568 A1* | 3/2007 | Dorstewitz ............... 410/97 |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0083236 A1* | 4/2007 | Sikora et al. ............ 606/232 |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1* | 8/2007 | Stone et al. ............ 606/232 |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198036 A1 | 8/2007 | Sklar et al. |
| 2007/0219558 A1 | 9/2007 | Deutsch |
| 2007/0225719 A1 | 9/2007 | Stone et al. |
| 2007/0225805 A1 | 9/2007 | Schmieding |
| 2007/0233241 A1 | 10/2007 | Graf et al. |
| 2007/0239209 A1* | 10/2007 | Fallman ............... 606/232 |
| 2007/0239275 A1 | 10/2007 | Willobee |
| 2007/0250059 A1 | 10/2007 | Weisshaupt et al. |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2008/0027430 A1 | 1/2008 | Montgomery et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1* | 4/2008 | Stone et al. ............... 606/232 |
| 2008/0082128 A1* | 4/2008 | Stone ............... 606/232 |
| 2008/0097430 A1 | 4/2008 | Bernstein et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0300611 A1 | 12/2008 | Houser et al. |
| 2008/0312689 A1* | 12/2008 | Denham et al. ............... 606/232 |
| 2009/0018589 A1 | 1/2009 | Smisson, III et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1* | 3/2009 | Kaiser et al. ............... 606/228 |
| 2009/0099598 A1 | 4/2009 | McDevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |

(56) References Cited

U.S. PATENT DOCUMENTS

| | | |
|---|---|---|
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0022083 A1 | 1/2011 | DiMatteo et al. |
| 2011/0026141 A1 | 2/2011 | Barrows |
| 2011/0046733 A1 | 2/2011 | Eggli |
| 2011/0087284 A1 | 4/2011 | Stone et al. |
| 2011/0098727 A1* | 4/2011 | Kaiser et al. ............ 606/144 |
| 2011/0106153 A1* | 5/2011 | Stone et al. ............. 606/228 |
| 2011/0112537 A1 | 5/2011 | Bernstein et al. |
| 2011/0112538 A1 | 5/2011 | Dell'Oca |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0004669 A1 | 1/2012 | Overes et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0089193 A1 | 4/2012 | Stone et al. |
| 2012/0095470 A1 | 4/2012 | Kaiser et al. |
| 2012/0109156 A1 | 5/2012 | Overes et al. |
| 2012/0116409 A1 | 5/2012 | Stone |
| 2012/0116450 A1 | 5/2012 | McDevitt et al. |
| 2012/0116452 A1 | 5/2012 | Stone et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0143215 A1 | 6/2012 | Corrao et al. |
| 2012/0150223 A1 | 6/2012 | Manos et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0215257 A1 | 8/2012 | McDevitt et al. |
| 2012/0245585 A1 | 9/2012 | Kaiser et al. |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'Oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0035722 A1 | 2/2013 | McDevitt et al. |
| 2013/0046341 A1 | 2/2013 | Stone et al. |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham et al. |
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0237997 A1 | 9/2013 | Arai et al. |
| 2013/0245761 A1 | 9/2013 | Conner et al. |
| 2013/0274812 A1 | 10/2013 | Dell'Oca |
| 2013/0289564 A1 | 10/2013 | Bernstein et al. |
| 2013/0317621 A1 | 11/2013 | Metzger et al. |
| 2013/0331848 A1 | 12/2013 | Kaiser et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsman et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0350674 A1 | 11/2014 | Stone et al. |
| 2015/0012094 A1 | 1/2015 | Denham et al. |
| 2015/0057757 A1 | 2/2015 | Metzger et al. |

FOREIGN PATENT DOCUMENTS

| | | |
|---|---|---|
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 C | 2/1986 |
| DE | 4127550 | 2/1993 |
| DE | 4302397 | 7/1993 |
| DE | 29621340 | 5/1998 |
| DE | 19841252 | 3/2000 |
| DE | 20207781 U1 | 8/2002 |
| EP | 19062 A1 | 11/1980 |
| EP | 0108912 | 5/1984 |
| EP | 0129422 | 12/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 440991 A1 | 8/1991 |
| EP | 0441065 | 8/1991 |

(56) References Cited

FOREIGN PATENT DOCUMENTS

| | | |
|---|---|---|
| EP | 0451932 | 10/1991 |
| EP | 0464480 | 1/1992 |
| EP | 0490417 | 6/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 2238944 A2 | 10/2010 |
| EP | 2544607 A1 | 1/2013 |
| EP | 2709557 A1 | 3/2014 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9609797 A1 | 4/1996 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2005122954 | 12/2005 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |
| WO | WO-2014/100109 A1 | 6/2014 |
| WO | WO-2014151766 A1 | 9/2014 |

OTHER PUBLICATIONS

Notice of Allowance mailed Oct. 7, 2013 for U.S. Appl. No. 12/702,067.

Notice of Allowance mailed Oct. 24, 2013 for U.S. Appl. No. 13/412,127.

Office Action mailed Dec. 13, 2013 for U.S. Appl. No. 13/412,105.

"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique" brochure, Biomet® Sports Medicine. (2013) 16 pages.

Office Action dated Nov. 4, 2014 for U.S. Appl. No. 13/288,459, filed Nov. 3, 2011.

International Search Report and Written Opinion mailed Mar. 6, 2014 for PCT/US2013/075989 which claims benefit of U.S. Appl. No. 13/720,648, filed Dec. 19, 2012.

Ziptight™ Fixation System Featuring Zip Loop™ Technology. Ankle Syndesmosis. Surgical Protocol by Timothy Charlton, M.D. Biomet Sports® Medicine brochure. (Jun. 15, 2011) 8 pages.

"ToggleLoc™ Fixation Device with ZipLoop™ Technology: ACL Reconstruction Bone-Tendon-Bone," by James R. Andrews, M.D., of Biomet Sports Medicine, a Biomet Company Brochure (2013), pp. 1-20.

International Preliminary Report on Patentability and Written Opinion mailed May 30, 2014 for PCT/US2012/064832 which claims benefit of U.S. Appl. No. 13/295,126, filed Nov. 14, 2011.

International Search Report and Written Opinion mailed Jun. 6, 2014 for PCT/US2014/026413 which claims benefit of U.S. Appl. No. 14/095,614, filed Dec. 3, 2013 and U.S. Appl. No. 14/095,639, filed Dec. 3, 2013.

ToggleLoc Fixation Device with ZipLoop Technology: Biceps Tendon Reattachment by Mark J. Albritton, M.D. and Daniel Worrel, M.D. of Biomet Sports Medicine, a Biomet Company Brochure (2099, 2011), pp. 1-12.

"AperFix® System Surgical Technique Guide. Single Tunnel Double Bundle.™" Cayenne Medical brochure. (Aug. 2008) 8 sheets.

(56) References Cited

OTHER PUBLICATIONS

"Arthroscopic Meniscal Repair using the Meniscal Cinch™", Surgical Technique brochure. (2008) Arthrex® 6 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. and it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Suture Tensioner w/Tensiometer," Arthrex®, Inc. catalog "Next Generation in Knee Ligament Reconstruction & Repair Technology," 2009.
"Technique for ACL Reconstruction with Acufex Director Drill Guide and Endobutton CL," by Thomas D. Roseberg, copyright 1999 Smith & Nephew.
"TriTis™ Tibial Fixation System and Implant" brochure. Scandius Biomedical (2006).
A. Weiler, et al; Biodegradierbare Interferenzschrauben in der Kreuzbandchirurgie; OP-Journal 14 pp. 278-284; (Mar. 1998).
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library. http://www.shoulder.com/bass_barber.html Printed May 19, 2005.
F. Alan Barber, M.D., "Using Sutures and Anchors," San Diego Shoulder Arthroscopy Course, 17th Annual Meeting. (Jun. 14, 2000).
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
International Search Report and Written Opinion mailed Feb. 6, 2013 for PCT/US2012/064832 which claims benefit of U.S. Appl. No. 13/295,126, filed Nov. 14, 2011.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Mar. 6, 2013 for PCT/US2012/062738 which claims benefit of U.S. Appl. No. 13/288,459, filed Nov. 3, 2011.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
Interview Summary mailed Nov. 27, 2012 for U.S. Appl. No. 13/098,897.
Interview Summary mailed Jul. 14, 2011 for U.S. Appl. No. 12/196,407.
Interview Summary mailed Jul. 14, 2011 for U.S. Appl. No. 12/196,410.
Interview Summary mailed Jul. 14, 2011 for U.S. Appl. No. 12/196,410, filed Aug. 22, 2008.
Interview Summary mailed Jun. 20, 2011 for U.S. Appl. No. 12/196,405.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jul. 19, 2012, for PCT/US2012/037703 claiming benefit of U.S. Appl. No. 13/109,667, filed May 7, 2011.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Notice of Allowance (Supplemental Notice of Allowability) mailed Apr. 15, 2011 for U.S. Appl. No. 12/196,398, filed Aug. 22, 2008; now U.S. Pat. No. 7,959,650.
Notice of Allowance (Supplemental Notice of Allowability) mailed Mar. 9, 2011 for U.S. Appl. No. 12/196,398, filed Aug. 22, 2008; now U.S. Pat. No. 7,959,650.
Notice of Allowance mailed Oct. 13, 2011 for U.S. Appl. No. 12/196,410.
Notice of Allowance mailed Oct. 26, 2011 for U.S. Appl. No. 12/196,405.
Notice of Allowance mailed Oct. 26, 2011 for U.S. Appl. No. 12/196,407.
Notice of Allowance mailed Mar. 22, 2012 for U.S. Appl. No. 13/102,182.
Notice of Allowance mailed Jun. 1, 2009 for U.S. Appl. No. 11/541,506.
Notice of Allowance mailed Sep. 18, 2009 for U.S. Appl. No. 11/541,505.
Notice of Allowance mailed Jun. 1, 2009 for U.S. Appl. No. 11/541,506, filed Sep. 29, 2006; now U.S. Pat. No. 7,601,165.
Notice of Allowance with Interview Summary mailed Aug. 31, 2011 for U.S. Appl. No. 12/474,802, filed Nov. 3, 2010.
Notice of Allowance with Interview Summary mailed Feb. 3, 2011 for U.S. Appl. No. 12/196,398, filed Aug. 22, 2010; now U.S. Pat. No. 7,959,650.
Office Action from the U.S. Patent Office mailed Mar. 5, 2013 for U.S. Appl. No. 12/702,067.
Office Action from the U.S. Patent Office mailed Mar. 13, 2013 for U.S. Appl. No. 13/181,729.
Office Action from the U.S. Patent Office mailed Mar. 20, 2013 for U.S. Appl. No. 13/399,125.
Office Action from the U.S. Patent Office mailed May 22, 2013 for U.S. Appl. No. 13/098,927.
Office Action from the U.S. Patent Office mailed Jul. 15, 2013 for U.S. Appl. No. 13/587,374.
Office Action from the U.S. Patent Office mailed Aug. 7, 2013 for U.S. Appl. No. 13/412,127.
Office Action from the U.S. Patent Office mailed Sep. 11, 2013 for U.S. Appl. No. 13/412,116.
Office Action mailed Oct. 24, 2012 for U.S. Appl. No. 13/399,125.
Office Action mailed Dec. 7, 2011 for U.S. Appl. No. 12/589,168.

(56) References Cited

OTHER PUBLICATIONS

Office Action mailed Sep. 21, 2012 for U.S. Appl. No. 13/098,897.
Office Action mailed Sep. 24, 2012 for U.S. Appl. No. 13/098,927.
Office Action mailed Apr. 11, 2011 for U.S. Appl. No. 12/196,405.
Office Action mailed May 19, 2009 for U.S. Appl. No. 11/541,505, filed Sep. 29, 2006; now U.S. Pat. No. 7,658,751.
Office Action mailed May 4, 2011 for U.S. Appl. No. 12/196,407, filed Aug. 22, 2008.
Office Action mailed May 9, 2011 for U.S. Appl. No. 12/196,410, filed Aug. 22, 2008.
Office Action mailed Feb. 10, 2012 for U.S. Appl. No. 13/181,729.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Pioneer® Sternal Cable System (2010).
Rapid Sternal Closure (2006) KLS Martin L.P. http://www.rapidsternalclosure.com/medical/demo.php Web accessed Sep. 8, 2008.
Restriction Requirement mailed Mar. 22, 2011 for U.S. Appl. No. 12/196,407, filed Aug. 22, 2008.
Restriction Requirement mailed Mar. 9, 2009 for U.S. Appl. No. 11/541,505, filed Sep. 29, 2006; now U.S. Pat. No. 7,658,751.
Restriction Requirement mailed Mar. 9, 2009 for U.S. Appl. No. 11/541,506, filed Sep. 29, 2006; now U.S. Pat. No. 7,601,165.
Restriction Requirement mailed Sep. 29, 2010 for U.S. Appl. No. 12/196,398, filed Aug. 22, 2008; now U.S. Pat. No. 7,959,650.
Roy Alan Majors, M.D.; "Meniscal repairs: proven techniques and current trends," Lippincott Williams & Wilkins, Inc.; 2002.
Saxena, Pankaj, MCh, DNB et al., "Use of Double Wires in Sternal Closure, A Useful Technique," Texas Heart® Institute. Journal List>Tex Heart Inst J > v.33(4); (2006).
Shoulder Arthroscopy; pp. H-2-H-22. (date unknown).
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Zeitani, Jacob, M.D., "A New Sternal Reinforcement Device to Prevent and Treat Sternal Dehiscence," CTSNet.org (Jun. 30, 2008).
US 6,238,418, 05/2001, Schwartz et al. (withdrawn)

\* cited by examiner

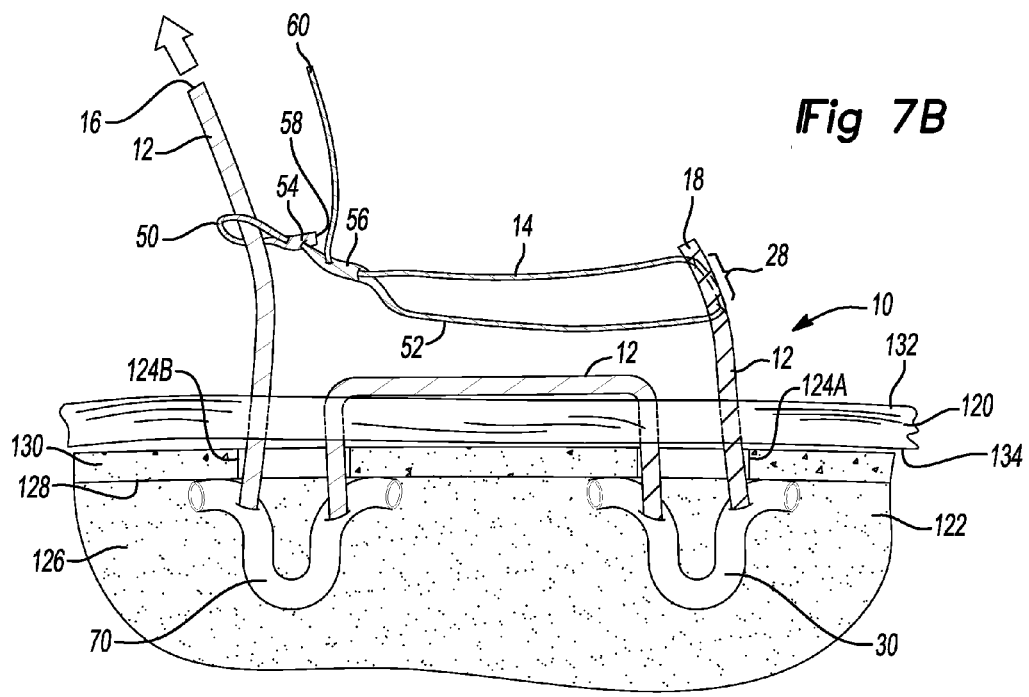
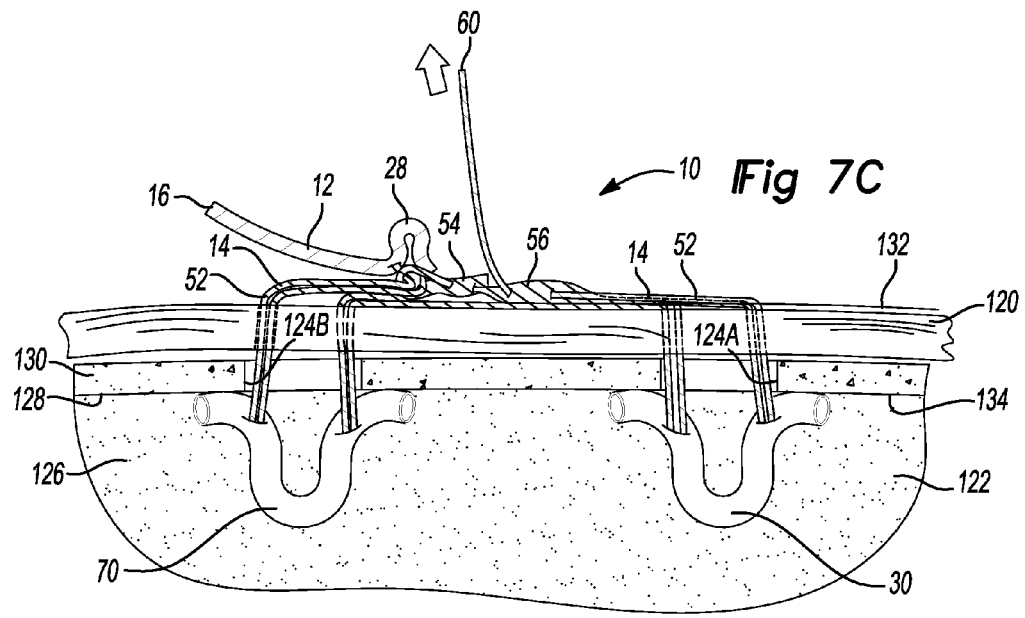

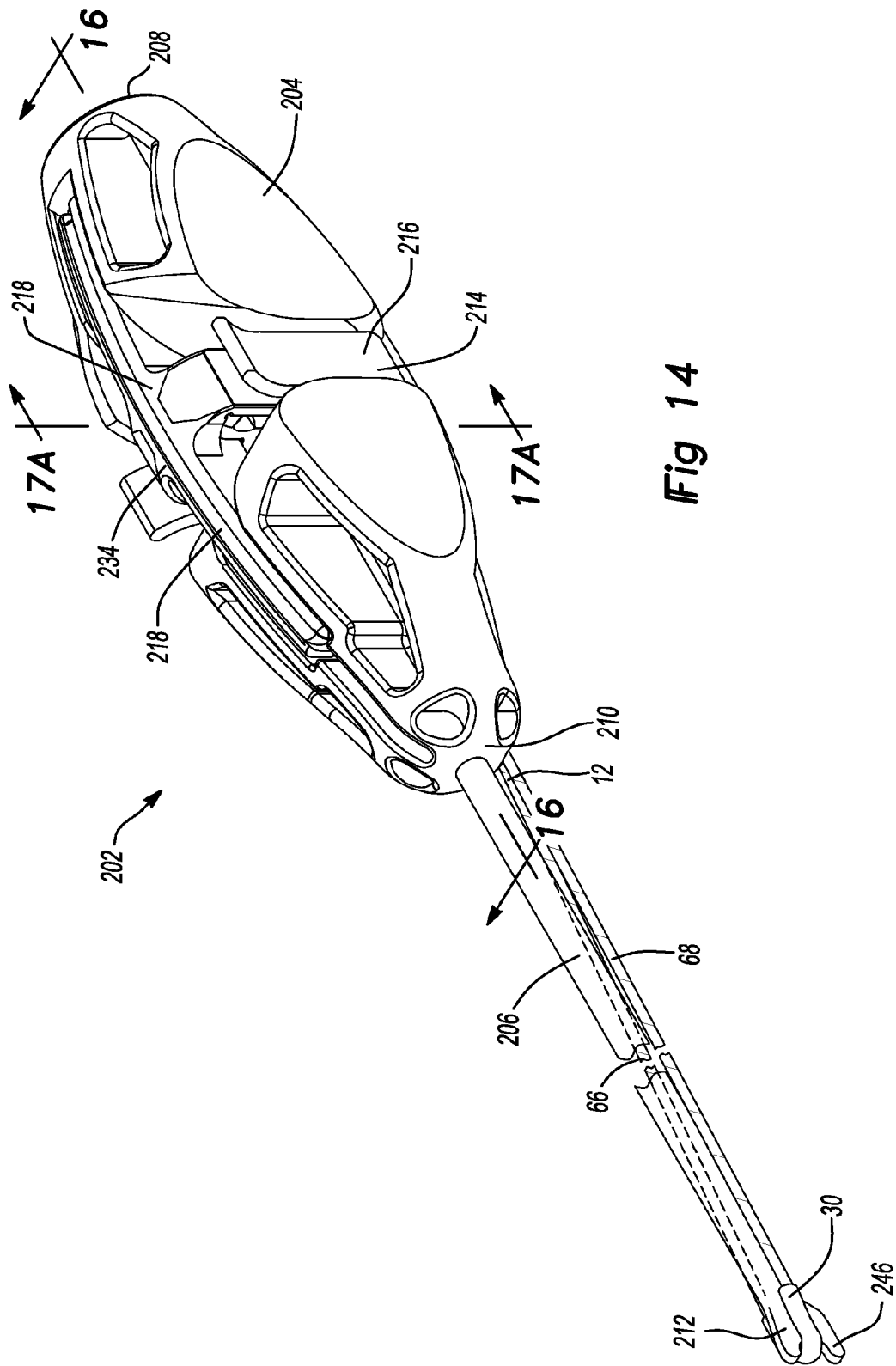

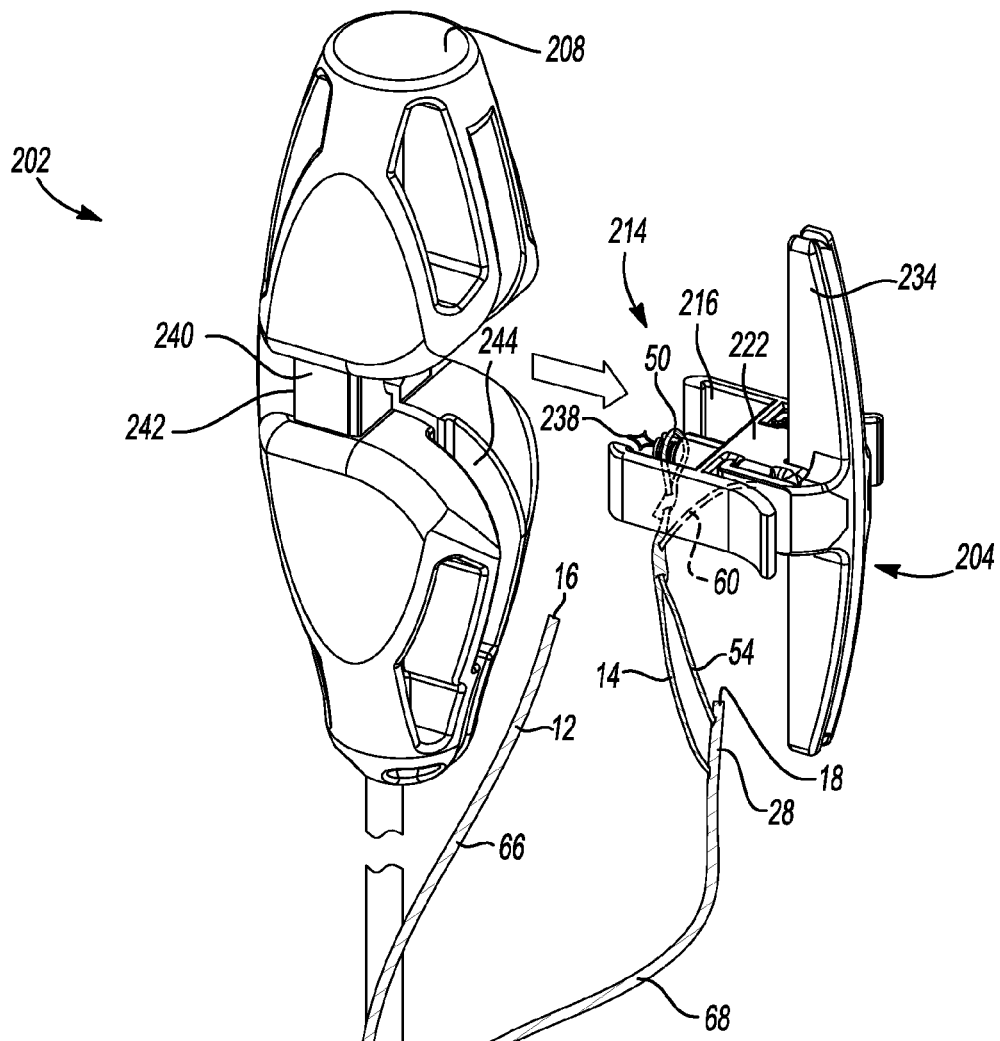
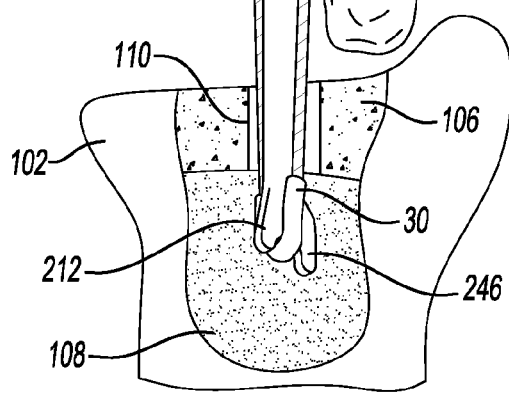
Fig 19

METHOD FOR COUPLING SOFT TISSUE TO A BONE

CROSS-REFERENCE TO RELATED APPLICATIONS

This application is a continuation-in-part of U.S. patent application Ser. No. 13/293,825 filed on Nov. 10, 2011, now U.S. Pat. No. 9,149,267, the entire disclosure of which is incorporated herein by reference.

FIELD

The present disclosure relates to methods for coupling a first tissue to a second tissue, such as coupling soft tissue to bone and methods for coupling two portions of soft tissue together.

BACKGROUND

This section provides background information related to the present disclosure, which is not necessarily prior art.

Arthroscopic procedures often include sutures and anchors to secure soft tissue to bone, and to secure separated portions of soft tissue together. Despite their widespread use, sutures and suture anchors, as well as methods for their use, can be improved. For example, tying sutures into knots may be very time consuming and difficult to perform, particularly inside the joint space. As a result, the cost of the procedure may be increased and the capacity of the surgeon may be limited. Furthermore, the strength of the repair may be limited by the strength of the knot. The methods and apparatuses disclosed herein address these issues and numerous others.

SUMMARY

This section provides a general summary of the disclosure, and is not a comprehensive disclosure of its full scope or all of its features.

The present teachings provide for a method for coupling tissue with a flexible member including a tail and a self-locking construct coupled to the tail. The self-locking construct includes a first loop and an adjustable second loop coupled thereto. The method includes implanting an anchor in bone. The anchor is slidably mounted to the tail. The tail is positioned relative to the tissue. An end of the tail is inserted through the first loop. The tail is passed through the first loop. The second loop is pulled into the anchor. The self-locking construct is positioned relative to the tissue. The self-locking construct is tightened against the tissue by pulling on an end of the self-locking construct.

The present teachings further provide for a method for coupling tissue with a flexible member including a tail and a self-locking construct coupled to the tail. The self-locking construct includes a first loop and a second adjustable loop coupled thereto. The method includes implanting an anchor in bone, the anchor slidably mounted to the tail. The tail is passed through the tissue. An end of the tail is inserted through the first loop. The tail is passed through the first loop. The second adjustable loop is pulled into the anchor. The self-locking construct is positioned through the tissue. The self-locking construct is tightened against the tissue by pulling on an end of the self-locking construct.

The present teachings further provide for a method for coupling tissue with a flexible member including a tail and a self-locking construct coupled to the tail. The self-locking construct includes a first loop and a second adjustable loop coupled thereto. The method includes passing the tail through a first tissue and a second tissue. An end of the tail is inserted through the first loop. The tail is passed through the first loop. The second adjustable loop is pulled into and across both the first tissue and the second tissue. The self-locking construct is tightened against both the first tissue and the second tissue by pulling on an end of the self-locking construct to couple the first tissue to the second tissue.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 7B illustrates the suture tail being passed through the first suture loop;

FIG. 7C illustrates the suture construct tightened against the tissue to secure the tissue to bone;

FIG. 14 is a perspective view of an insertion device according to the present teachings;

FIGS. 18-23 illustrate a method of using the insertion device of FIG. 14 to secure tissue to bone with the knotless suture anchor device;

Corresponding reference numerals indicate corresponding parts throughout the several views of the drawings.

DETAILED DESCRIPTION

Example embodiments will now be described more fully with reference to the accompanying drawings.

Figure 1A:
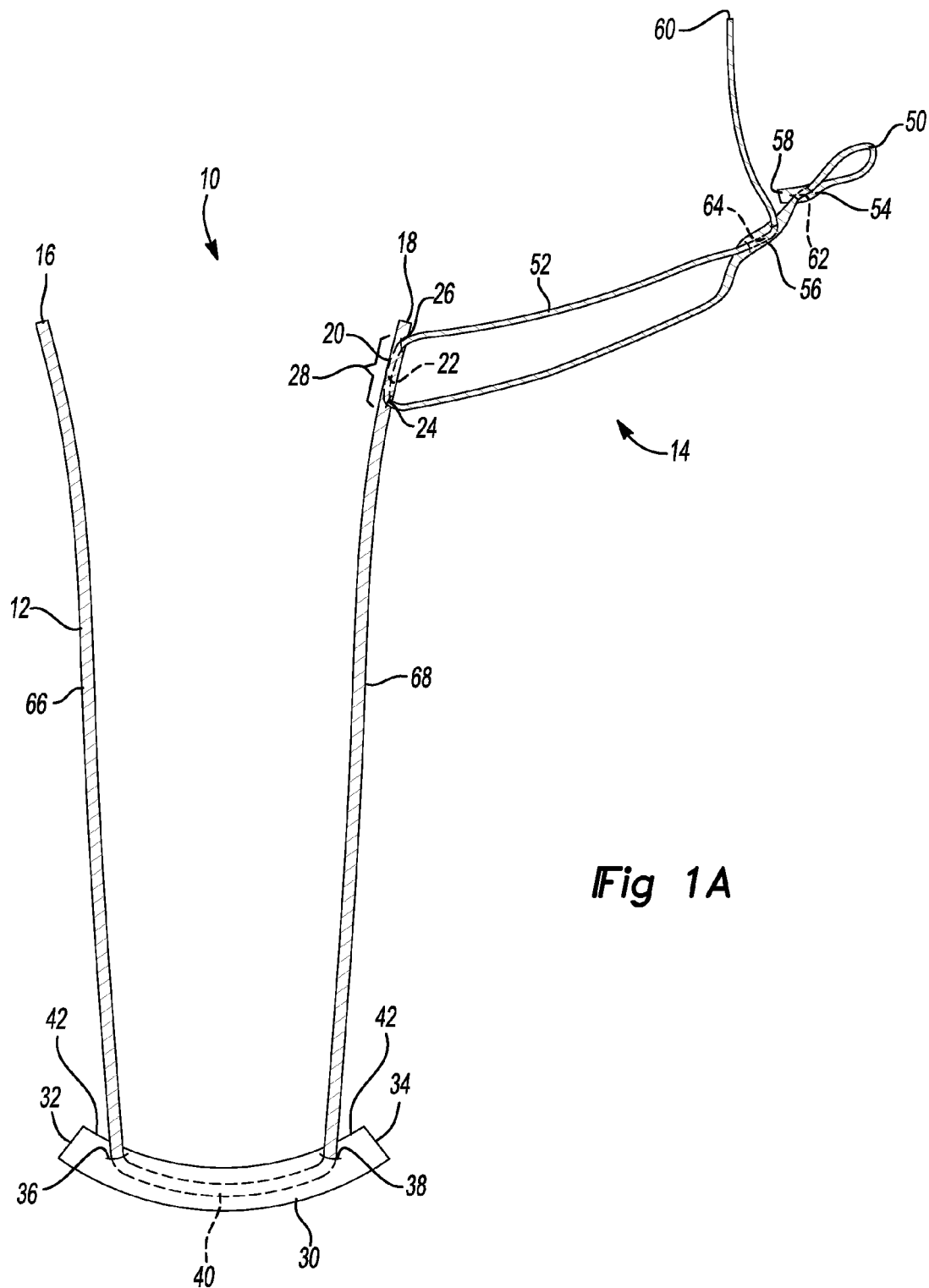
FIG. 1A illustrates a knotless suture anchor device according to the present teachings.

With initial reference to FIG. 1A, a knotless suture anchor device, or assembly, or system is generally illustrated at reference numeral 10. The device generally includes a suture tail 12 and a suture construct 14 connected thereto. The suture tail 12 and the suture construct 14 can be made of any suitable flexible material or member, and need not be made of a suture. The suture tail 12 and the suture construct 14 can be made of the same or different materials. When the suture tail 12 and/or the suture construct 14 are made of sutures, any suitable suture can be used. For example, a braided hollow-core suture can be used. The braided suture can include a first end and a second end with an outer wall that defines a passage therethrough. Any suitable braided suture can be used, such as any of the braided sutures disclosed in U.S. patent application Ser. No. 12/915,962 ('962 application) titled Method and Apparatus for Securing Soft Tissue to Bone, which was filed on Oct. 29, 2010, published as Publication No. 2011/0098727 on Apr. 28, 2011, and is assigned to Biomet Sports Medicine, LLC. The disclosure of the '962 application is incorporated herein by reference. To help distinguish between the suture tail 12 and the suture construct 14, which can be particularly helpful for a surgeon during surgery, the suture tail 12 and the suture construct 14 can be provide with different colors or designs, for example.

The suture tail 12 generally includes a first end 16 and a second end 18, which is opposite to the first end 16. The suture tail 12 can be any suitable length, such as about 30 inches. The suture tail 12 defines a suture tail sleeve portion 20 proximate to the second end 18 of the suture tail 12. While the suture tail sleeve portion 20 is illustrated as being proximate to the second end 18, it may alternatively be proximate to the first end 16 or at any suitable position therebetween. The suture tail sleeve portion 20 defines an elongated passageway 22 extending along at least a portion of the suture tail 12. If the suture tail 12 is a braided hollow-core suture, the passageway 22 can extend from the first end 16 to the second end 18 of the suture tail 12. The passageway 22 exits through an outer wall of the suture tail 12 at a first opening 24 and a second opening 26 at opposite ends of the passageway 22. The second opening 26 is closer to the second end 18 of the suture tail 12 than the first opening 24 is. The second opening 26 is spaced apart from the second end 18. The suture construct 14 extends through the suture tail sleeve portion 20 to connect the suture construct 14 to the suture tail 12. The portion of the suture tail 12 defining the suture tail sleeve portion 20 and the portions of the suture tail 12 proximate to either end thereof define a locking member or portion 28 of the suture tail 12, as further described herein.

The suture tail 12 can include a soft or flexible anchor 30 at any suitable position between the first end 16 and the second end 18, such as about halfway between the first end 16 and the second end 18. The anchor 30 can be an elongate member having a sleeve or tubular configuration with a first anchor end 32 and a second anchor end 34 at opposite ends thereof. An internal passage 40 is defined by a wall of the anchor 30 and extends between the first anchor end 32 and the second anchor end 34. The anchor 30 can be made of resorbable or non-resorbable materials, including braided suture, sponges and sponge-like materials, including braided suture, sponges and sponge-like materials in solid form, perforated materials, woven/braided from biocompatible materials or fibers, such as, for example, polymer, polyester, polyethylene, cotton, silk, or other natural or synthetic materials.

The anchor 30 can have any properties that allow the anchor 30 to change shape. In this regard, the anchor 30 can be, for example, complaint, flexible, foldable, squashable, squeezable, deformable, limp, flaccid, elastic, low-modulus, soft, spongy or perforated, or have any other characteristic property that allows it to change shape. In some aspects, the anchor 30 can be coated with biological or biocompatible coatings and also can be soaked in platelets and other biologics, which can be easily absorbed by the flexible anchor 30. In an exemplary configuration, the anchor 30 can be formed from a strand of No. 5 braided polyester suture. In other words, multiple fibers can be braided together to form a hollow braided suture having a longitudinal passage.

The anchor 30 includes a first opening 36 and a second opening 38 defined in the wall of the anchor 30. The first opening 36 is proximate to, but spaced apart from, the first anchor end 32. The second opening 38 is proximate to, but spaced apart from, the second anchor end 34. The suture tail 12 can be can be passed through the second opening 38, guided into and along the internal passage 40, and passed out of the internal passage 40 through the first opening 36. The first and the second openings 36 and 38 can be apertures or voids in the woven fabric of the anchor 30, such that the first and the second openings 36 and 38 do not disrupt or break the weave of the anchor 30 between the first and the second anchor ends 32 and 34 and the corresponding first and second openings 36 and 38 can define anchoring leg or tail portions 42 that can provide additional resistance for securing the anchor 30 relative to the bone.

In one exemplary configuration, the suture tail 12 can pass only through the first and second openings 36 and 38 and a portion of the internal passage 40 extending therebetween to form a loop that does not extend through the first or the second anchor ends 32 and 34. In another exemplary configuration, the suture tail 12 can extend into the second anchor end 34, through the internal passage 40, and out the first anchor end 32. In such a configuration, the anchor 30 need not include the first opening 36 or the second opening 38. This configuration is described in U.S. application Ser. No. 13/485,304 filed May 31, 2012 and assigned to Biomet Sports Medicine, LLC of Warsaw, Ind., which is incorporated herein by reference and referred to herein as the '304 application. The anchor 30 can be any of the anchors disclosed in the '304 application. For example, the anchors of FIGS. 20 and 21 of the '304 application can be used when it is desirable to add additional flexible anchors In addition to the anchor 30, one or more additional anchors, identical to or substantially similar to the anchor 30, can be mounted to the suture tail 12. The device 10 can be provided with additional anchors mounted to the suture tail 12, and/or additional anchors can be added to the suture tail 12 during the surgical procedure. For example, a health care professional can add additional anchors to the suture tail 12. The additional anchors can be added in any suitable manner, such as by using any one of the anchor reload devices disclosed in the '304 application.

Figure 1B:
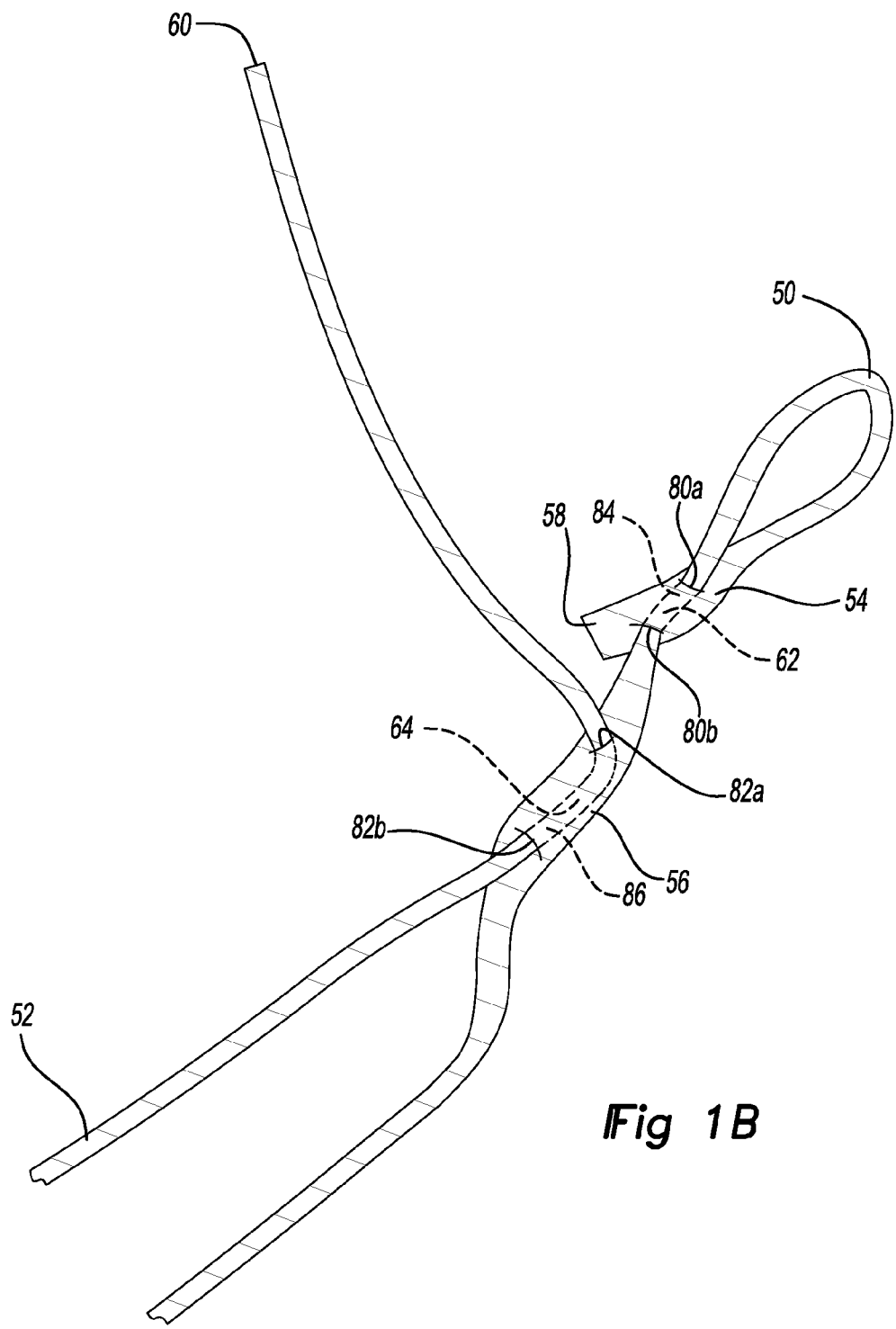
FIG. 1B is a close-up view of a suture construct of the knotless suture anchor device of FIG. 1A.
Figure 1C:
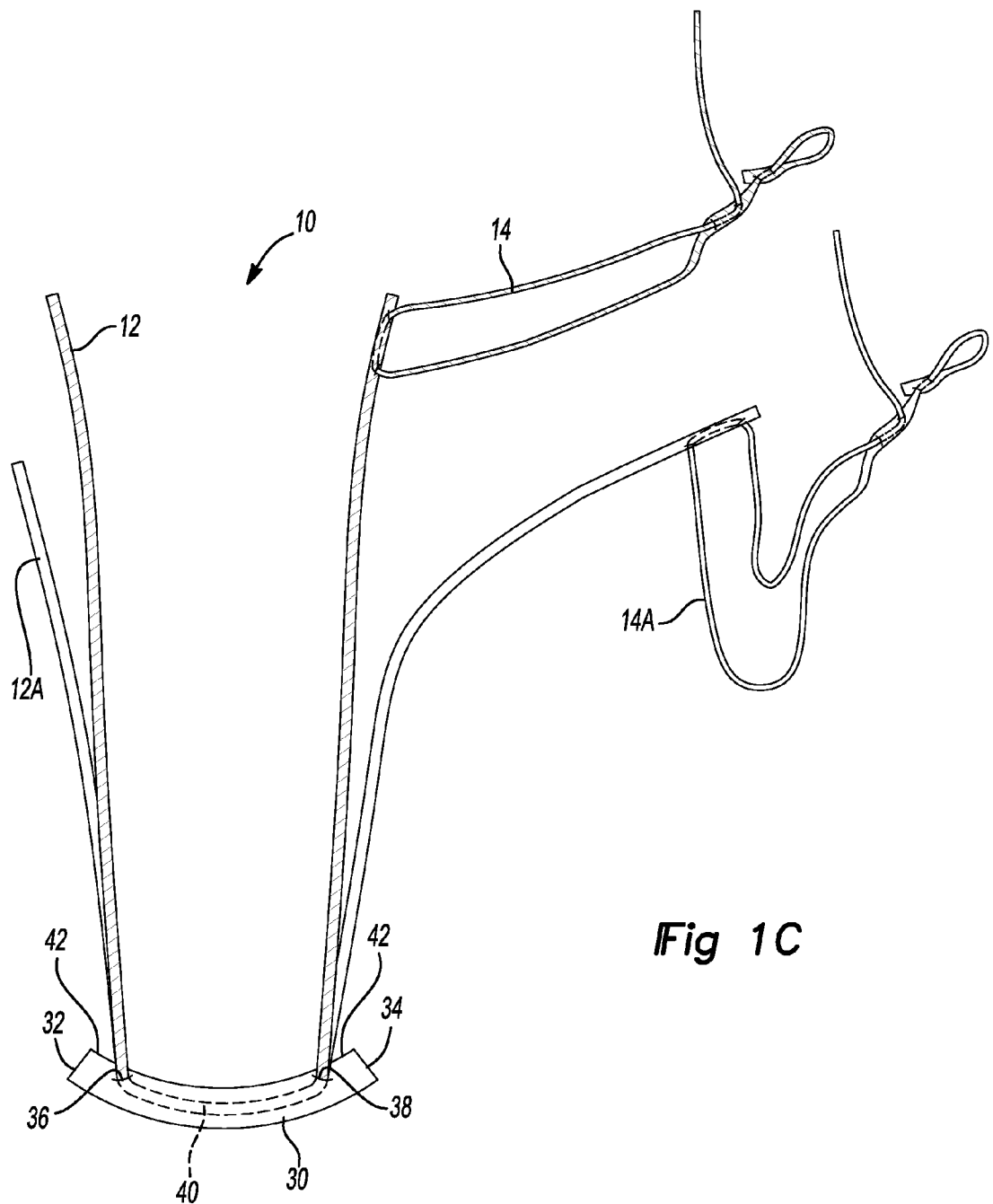
FIG. 1C illustrates another knotless suture anchor device according to the present teachings.

While FIG. 1A illustrates a single suture tail 12 connected to the anchor 30, one or more suture tails 12 each with a separate suture construct 14 can be connected to the anchor 30. The additional suture tail(s) 12 can extend through the internal passage 40 or through an additional anchor sleeve defined by the first anchor 30. For example and as illustrated in FIG. 1C, a second suture tail 12A can be seated in the internal passage 40 and thereby connected to the anchor 30. Connected to the second suture tail 12A is a second suture construct 14A. The second suture tail 12A and the second suture construct 14A can be substantially similar to, or identical to, the suture tail 12 and the suture construct 14 respectively. The suture tail 12 and the suture construct 14 can thus be a first suture tail 12 and a first suture construct 14.

The suture construct 14 is a self-locking suture construct including a braided suture. The suture construct generally includes a first adjustable suture loop 50, a second adjustable suture loop 52, a first suture construct body 54, and a second suture construct body 56. The first adjustable suture loop 50 can be non-adjustable as well. A first end 58 of the suture construct 14 is opposite to a second end 60 of the suture construct 14. With particular reference to FIG. 1B, the first body 54 defines a first passage portion 62. The second body 56 defines a second passage portion 64. The first passage portion 62 defines a first pair of apertures 80a and 80b at opposite ends thereof through a wall of suture construct 14. The second passage portion 64 defines a second pair of apertures 82a and 82b at opposite ends thereof through the wall of the suture construct 14. While the first and the second passage portions 62 and 64 each have two openings 80a/80b and 82a/82b respectively, the first and the second passage portions 62 and 64 can have additional openings and/or can include additional passage portions.

The first body 54 is formed proximate to the first end 58 of the suture construct 14. A portion of the suture construct 14 between the second body 56 and the first end 58 is passed through the first pair of apertures 80a and 80b of the first passage portion 62 to define the first adjustable suture loop or noose 50. The size of the first adjustable suture loop 50 can be adjusted by sliding the first end 58 of the suture construct 14 along the first adjustable suture loop 50. For example, the first adjustable suture loop 50 can be closed (made smaller) by sliding the first end away from the second body 56.

Tension in the first adjustable suture loop 50 can cause the first body 54 defining the first passage portion 62 to be placed in tension and therefore cause first passage portion 62 to constrict about portion 84 passed therethrough. This constriction reduces the diameter of the first passage portion 62, thus forming a mechanical interface between exterior surfaces of portion 84 and an interior surface of the first passage portion 62. This constriction results in static friction between the interior and exterior surfaces at the mechanical interface, causing the first adjustable suture loop 50 to "automatically" lock in a reduced size or diameter configuration in which tension is maintained without use of a knot. This can be used to secure the first adjustable suture loop 50 to the second adjustable suture loop 52, as described herein.

The second end 60 of the suture construct 14 is passed through the first and the second openings 82a and 82b of the second passage portion 64 to define the second adjustable suture loop 52. The size of the second adjustable suture loop 52 can be adjusted by moving the second end 60 of the suture construct 14. For example, the second adjustable suture loop 52 can be closed (made smaller) by pulling on the second end 60. A portion of the suture construct 14 defining the second adjustable suture loop 52 extends through the suture tail sleeve portion 20, and is slidably received in the suture tail sleeve portion 20 to connect the suture construct 14 to the suture tail 12.

The pulling or tensioning of the first end 16 of the suture tail 12 can cause reciprocal movement of portion 86 relative to the second passage portion 64 and the second adjustable suture loop 52 can be reduced to a desired size and placed in a desired tension. Tension in the second adjustable suture loop 52 can cause the second body 56 defining the second passage portion 64 to be placed in tension and therefore cause second passage portion 64 to constrict about portion 86 passed therethrough. This constriction reduces the diameter of the second passage portion 64, thus forming a mechanical interface between exterior surfaces of portion 86 and an interior surface of the second passage portion 64. This constriction results in static friction between the interior and exterior surfaces at the mechanical interface, causing the second adjustable suture loop 52 to "automatically" lock in a reduced size or diameter configuration in which tension is maintained without use of a knot. This can be used to secure a labral tear, a rotator cuff tear, and/or in any other suitable procedure. Any other suitable self-locking suture construct configuration can be included as well, such as any of those disclosed in the '962 application.

With additional reference to FIG. 2, a method for implanting the knotless suture anchor device 10 in a bone 102 to secure a tissue 104 to the bone 102 will now be described. As illustrated, the bone 102 includes a hard, outer cortical bone layer 106 and a softer, inner cancellous bone layer 108. The bone 102 and tissue 104 can be any suitable bone and tissue. For example and as further described herein, the knotless suture anchor device 10 can be used to secure a torn rotator cuff or labrum in place.

Figure 2:
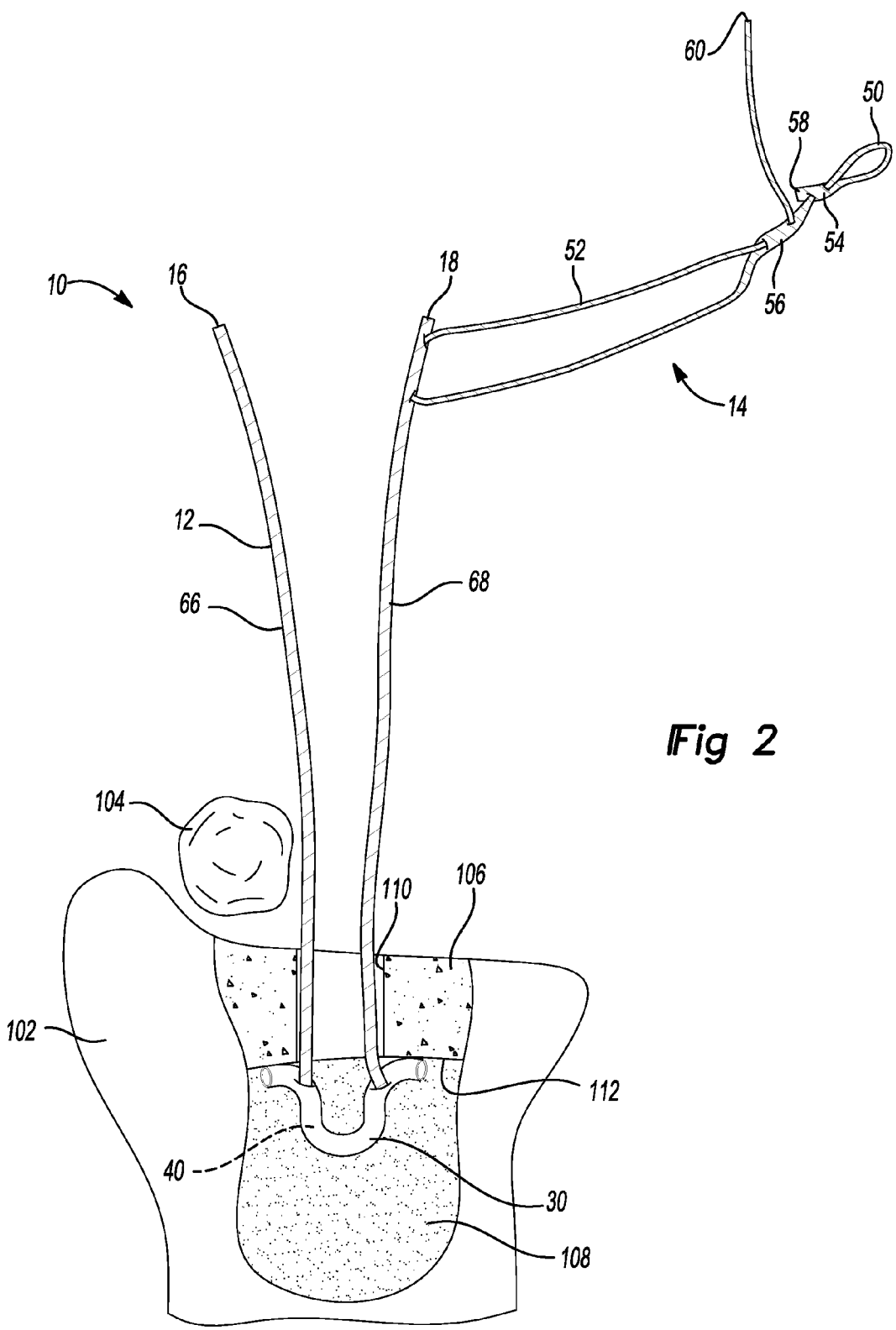
FIG. 2 illustrates the knotless suture anchor device of FIG. 1A implanted in bone.

As illustrated in FIG. 2, a bone hole 110 is formed in the bone 102 using any suitable device, such as a surgical drill. The bone hole 110 is formed proximate to the tissue 104 to be secured to the bone 102. The anchor 30 is inserted into the bone hole 110 and positioned such that the first anchor end 32 and the second anchor end 34 abut an undersurface 112 of the cortical bone layer 106 at opposite sides of the bone hole 110, which restricts the suture tail 12 from being pulled out from within the bone 102. The anchor 30 can be inserted using any suitable inserter, such as those described herein. The '962 application, which is incorporated by reference, provides additional disclosure for forming a bone hole and implanting a flexible anchor. The additional disclosure of the '962 application also applies to the forming of bone hole 110 and insertion of anchor 30 within the bone hole 110.

Figure 3:
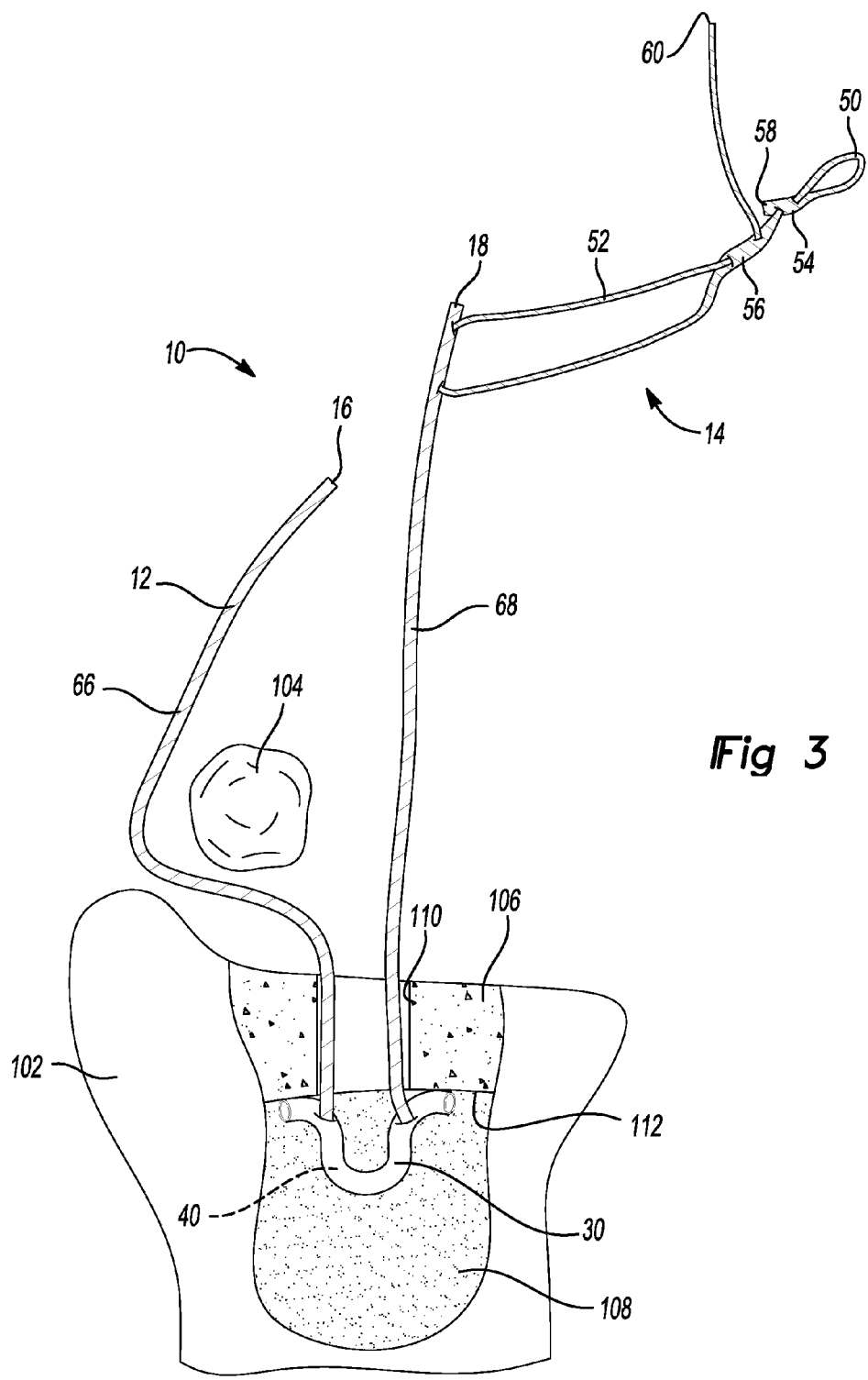
FIG. 3 illustrates a suture tail of the knotless suture anchor device of FIG. 1A passed around tissue.

With additional reference to FIG. 3, the first end 16 of the suture tail 12 is passed around and/or through the tissue 104 such that the tissue 104 is between a first portion 66 and a second portion 68 of the suture tail 12. The first portion 66 is between the first end 16 and the anchor 30. The second portion 68 is between the second end 18 and the anchor 30.

Figure 4:
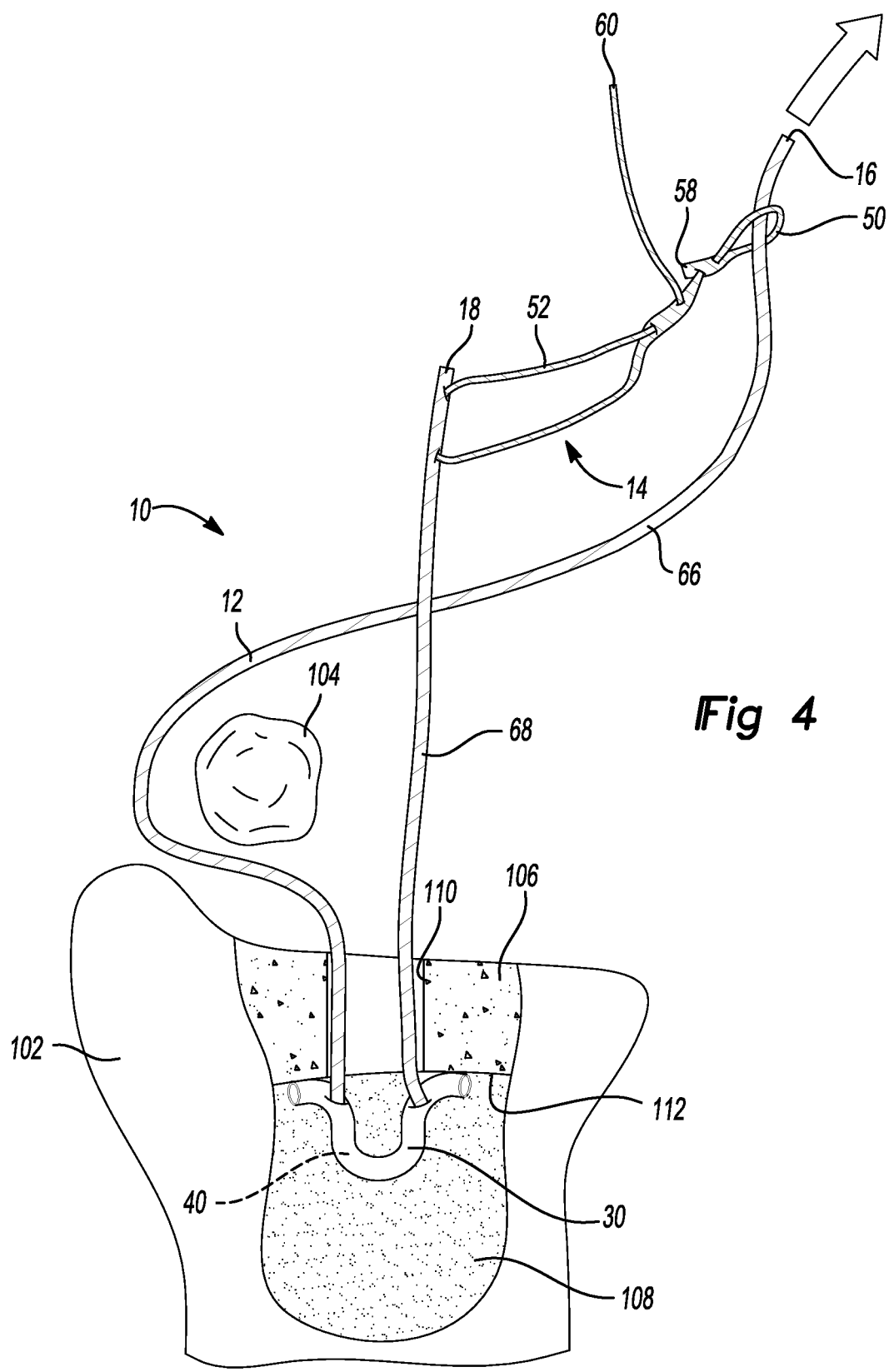
FIG. 4 illustrates the suture tail being passed through a first suture loop of the suture construct of the knotless suture anchor device of FIG. 1A.
Figure 5:
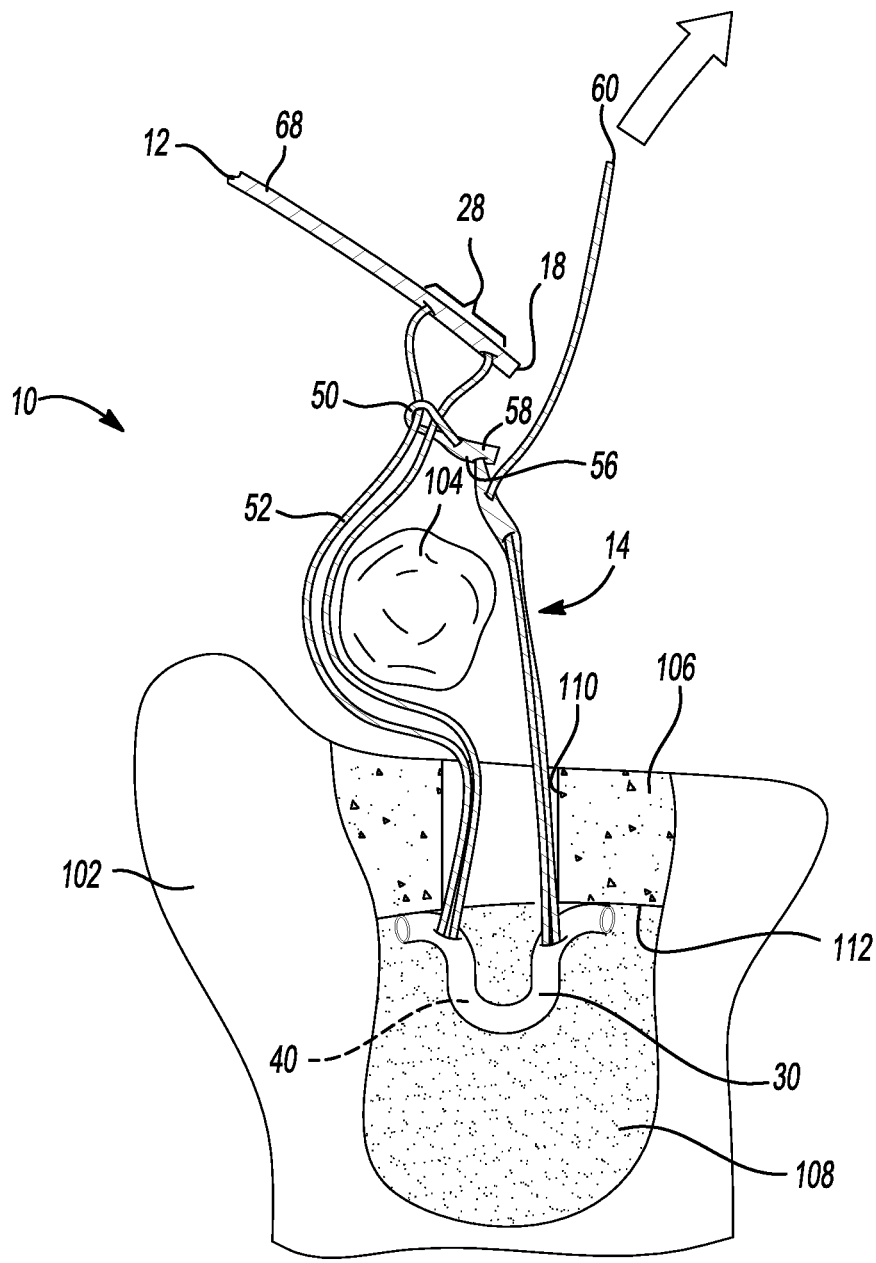
FIG. 5 illustrates the suture construct after it has been pulled through a soft anchor of the knotless suture anchor device of FIG. 1 to surround the tissue.

With additional reference to FIGS. 4 and 5, the first end 16 of the suture tail 12 is inserted through the first adjustable suture loop 50. The entire suture tail 12 is pulled through the first adjustable suture loop 50 and the entire suture tail 12 is pulled through the internal passage 40. Pulling the entire suture tail 12 through the internal passage 40 causes the suture construct 14 to be pulled into the internal passage 40 such that the second adjustable suture loop 52 extends through the internal passage 40. The internal passage 40 is thus dimensioned large enough to permit passage of both the suture tail 12 and the second adjustable suture loop 52. As illustrated in FIG. 5, the tissue 104 is encompassed entirely by the suture construct 14 and the second adjustable suture loop 52 extends through the first adjustable suture loop 50. The internal passage 40 is also dimensioned large enough to permit slidable adjustment of the suture construct 14 through the internal passage 40.

Figure 6:
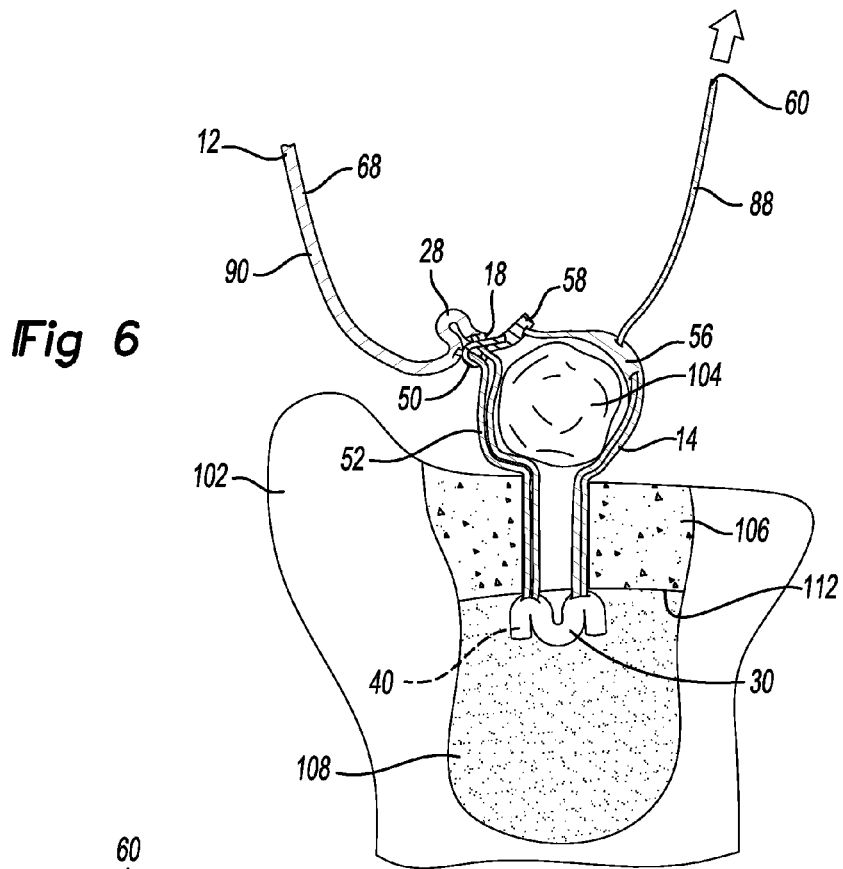
FIG. 6 illustrates the suture construct tightened around the tissue.

With continued reference to FIG. 5 and additional reference to FIG. 6, the second end 60 of the suture construct 14 is pulled to tighten the suture construct 14 around the tissue 104 and retain the tissue 104 against the bone 102 at any suitable tension. As described above, the second adjustable suture loop is self-locking, and thereby secures the tissue 101 without the need for tying a knot. To further secure the suture construct 14 around the tissue 104, the first end 58 of the suture construct 14 is slid away from the second body 56, which closes and tightens the first adjustable suture loop 50 onto the second adjustable suture loop 52 and provides further control over tension applied to the tissue 104. Further pulling of the second end 60 of the suture construct 14 draws the locking member 28 of the suture tail 12 against the first adjustable suture loop 50 to provide the locking member 28 with the locked configuration illustrated in FIG. 6. The first adjustable suture loop 50 and the second adjustable suture loop 52 surround the tissue 104, thereby defining a suture capture region of the device 10. As described above, the first adjustable suture loop is self-locking. Thus, the first adjustable suture loop 50 can be locked onto the second adjustable suture loop 52 without the need to tie a knot.

In the locked configuration of FIG. 6, the portions of the suture tail 12 defining the first opening 24 and the second opening 26 are drawn together, thereby causing the suture tail 12 to assume the locked configuration of FIG. 6, in which the locking member 28 has a generally horseshoe-shaped, u-shaped, or bunched, configuration. In the locked configuration of FIG. 6, the locking member 28 restricts the suture tail 12 from passing back through the first adjustable suture loop 50, which prevents the suture construct 14 from loosening its hold of the tissue 104 against the bone 102.

As illustrated in FIG. 6, upon tensioning the second adjustable suture loop 52 onto the tissue 104, the anchor 30 is forced upward against the undersurface 112 of the bone 102. This force causes the anchor 30 to deform to the collapsed, balled, or squished position of FIG. 6, which further retains the anchor 30 within the bone. Although the other figures herein do not specifically illustrate the anchor 30 within this configuration, further tensioning of the second adjustable suture loop 52 such that the anchor 30 is forced against the undersurface 112 of the bone 102 will cause the anchors 30 to assume the position of FIG. 6.

With continued reference to FIG. 6, excess portion 88 of the suture construct 14 pulled through the second body 56 at the second end 60 of the suture construct 14 can be cut and removed. The excess portion 90 of the suture tail 12 beyond the locking member 28 can be cut and removed as well. While the method for securing the tissue 104 to the bone 102 described above includes implanting the anchor 30 within the bone 102 before passing the suture tail 12 around the tissue 104, the suture tail 12 can be passed around the tissue before the anchor 30 is implanted in the bone 102.

Figure 7A:
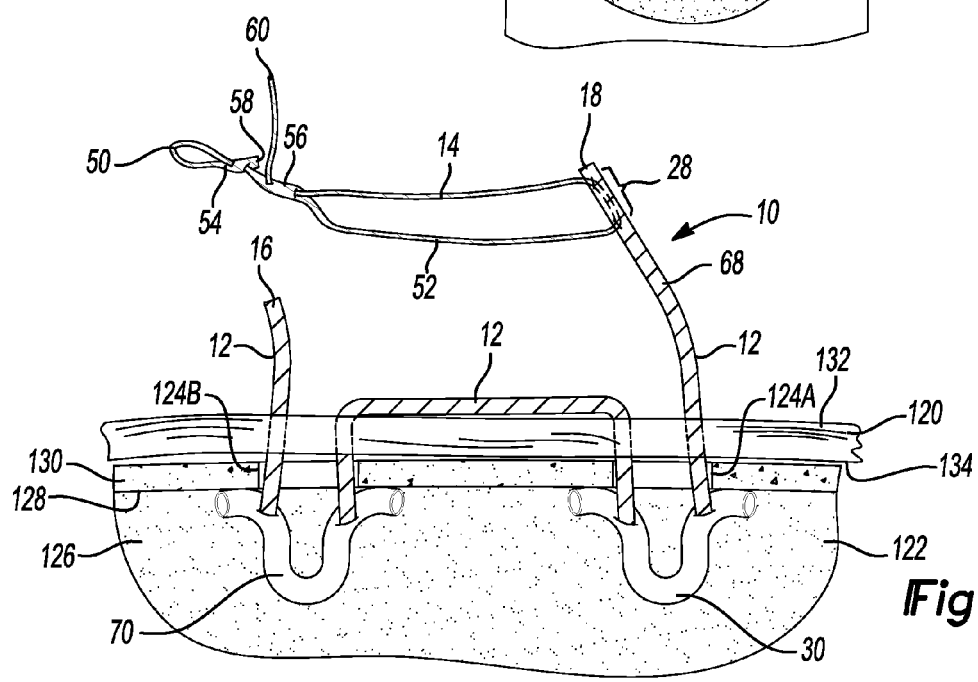
FIG. 7A illustrates the knotless suture anchor device of FIG. 1A implanted in bone and including a second soft anchor, the device implanted through tissue to secure the tissue to bone.

With additional reference to FIGS. 7A and 7B, use of the knotless suture anchor device 10 to secure a separated rotator cuff tissue 120 to a humerus 122 is illustrated. As illustrated, the device 10 includes a second anchor 70 attached to the suture tail 12 in addition to the anchor 30, which is also referred to herein as a first anchor 30. The second anchor 70 is substantially identical to, or the same as, the first anchor 30. The second anchor 70 can be attached to the suture tail 12 in any suitable manner, such as by using the suture anchor reload assembly disclosed in FIGS. 17-21 of the '304 application, which is incorporated herein by reference as set forth above. The second anchor 70 is attached to the suture tail 12 between the first end 16 of the suture tail 12 and the first anchor 30. The knotless suture anchor device 10 can be used to fasten any suitable portion of the tissue 120 to the humerus 122. For example, the device 10 can be arranged to extend in the medial to lateral direction, or to extend in the anterior to posterior direction.

With particular reference to FIG. 7A, the first anchor 30 is first implanted in a first bone hole 124A formed in the humerus 122 and arranged such that the first anchor 30 is secured within a cancellous bone layer 126 due to contact with an undersurface 128 of cortical bone layer 130. The first anchor 30 can be implanted in any suitable manner, such as by using the inserter 150 the '304 application, or any of the inserters described herein. The first anchor 30 is inserted through the rotator cuff tissue 120 such that both the first portion 66 of the suture tail 12 and the second portion 68 of the suture tail 12 extend through the rotator cuff tissue 120.

The second anchor 70 can be implanted in the humerus 122 in a second bone hole 124B in the same way that the first anchor 30 is implanted, such as by using the inserter disclosed in the '304 application or any of the inserters described herein. The second anchor 70 is implanted through the tissue 120, and thus the suture tail 12 extends through the tissue 120. Thus, as illustrated in FIG. 7A, the suture tail 12 extends through the tissue 120 twice at the first anchor 30 (first in through the tissue 120 to the first anchor 30 and then back out through the tissue 120 from the first anchor 30) and twice at the second anchor 70 (first in through the tissue 120 to the second anchor 70 and then back out through the tissue 120 from the second anchor 70).

With additional reference to FIG. 7B, the rotator cuff tissue 120 is tightened against the humerus 122 and secured thereto by inserting the first end 16 of the suture tail 12 through the first adjustable suture loop 50 of the suture construct 14, and pulling the suture tail 12 completely through the first and the second anchors 30 and 70, similar to that which is illustrated in FIGS. 4 and 5. As a result, the suture construct 14 is carried through and extends through both the first anchor 30 and the second anchor 70, as illustrated in FIG. 7C.

With continued reference to FIG. 7C, the first adjustable suture loop 50 is coupled to the second adjustable suture loop 52 at an outer surface 132 of the tissue 120. Pulling the second end 60 of the suture construct 14 tightens the suture construct 14 against the tissue 120 to hold an inner surface 134 of the tissue 120 against the humerus 122. Pulling the second end 60 also allows a surgeon to tension the tissue 120 against the humerus 122. In this arrangement, the suture construct 14 is thus implanted such that it overlaps the outer surface 132 of tissue 120 between the first anchor 30 and the second anchor 70, which permits fastening and tensioning of the tissue 120 to the humerus 122 over a large area. While two anchors 30 and 70 are illustrated, any suitable number of anchors can be added to the suture tail 12, as described in the '304 application for example, and implanted in a similar fashion to fasten a larger area of the tissue 120 to the humerus 122.

Although the tissue 120 is illustrated as one complete piece of tissue 120 in FIGS. 7A-7C, the knotless suture anchor device 10 can be used to couple, secure, and retain two separated (i.e., torn) portions of the tissue 120 together. For example and with reference to FIG. 7C, the knotless suture anchor device 10 can be arranged such that the first and the second anchors 30 and 70 are implanted on opposites of a tear in the tissue 120. Tightening the knotless suture anchor device 10 by pulling on the second end 60 as described above, will pull the two torn pieces together to facilitate healing.

Figure 8A:
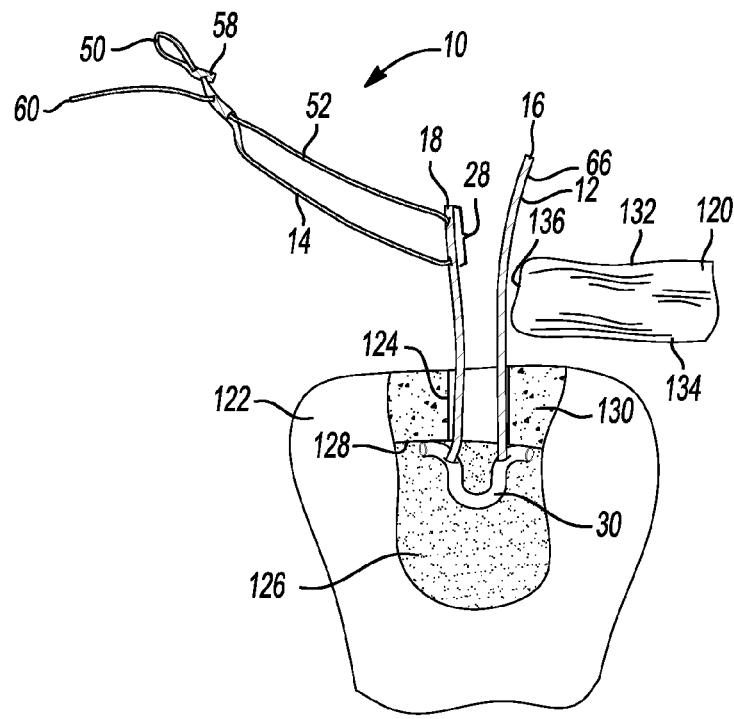
FIG. 8A-8D illustrates another method for coupling tissue to bone using the knotless suture anchor device of FIG. 1A.
Figure 8B:
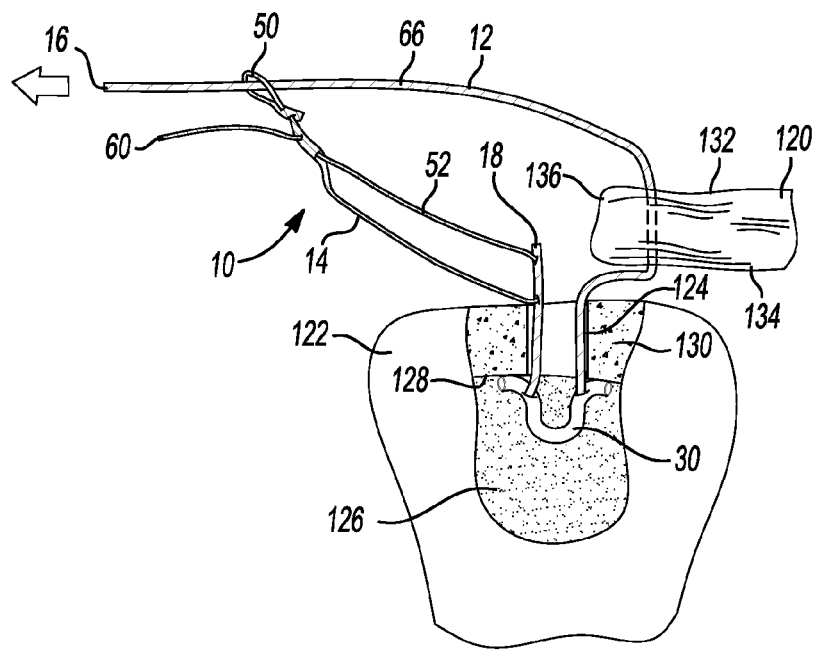
Figure 8C:
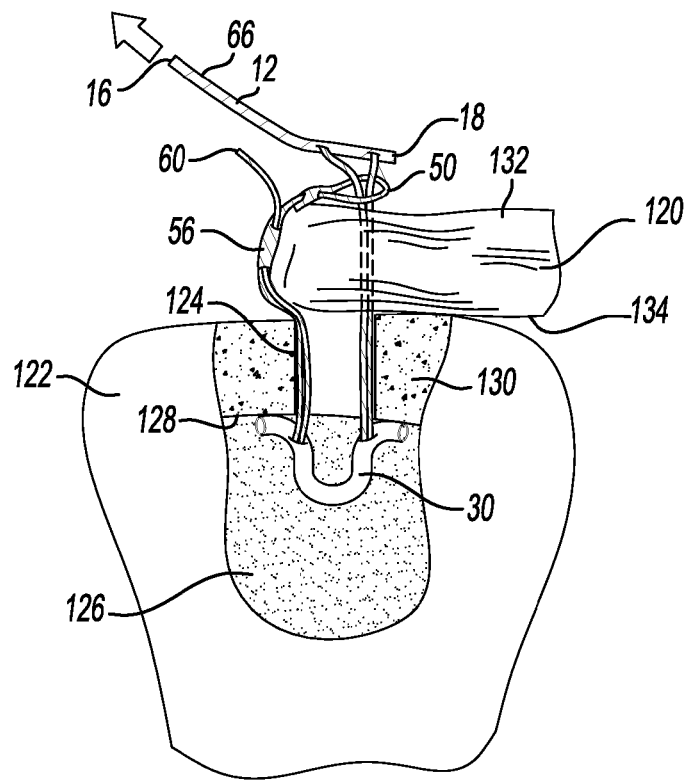
Figure 8D:
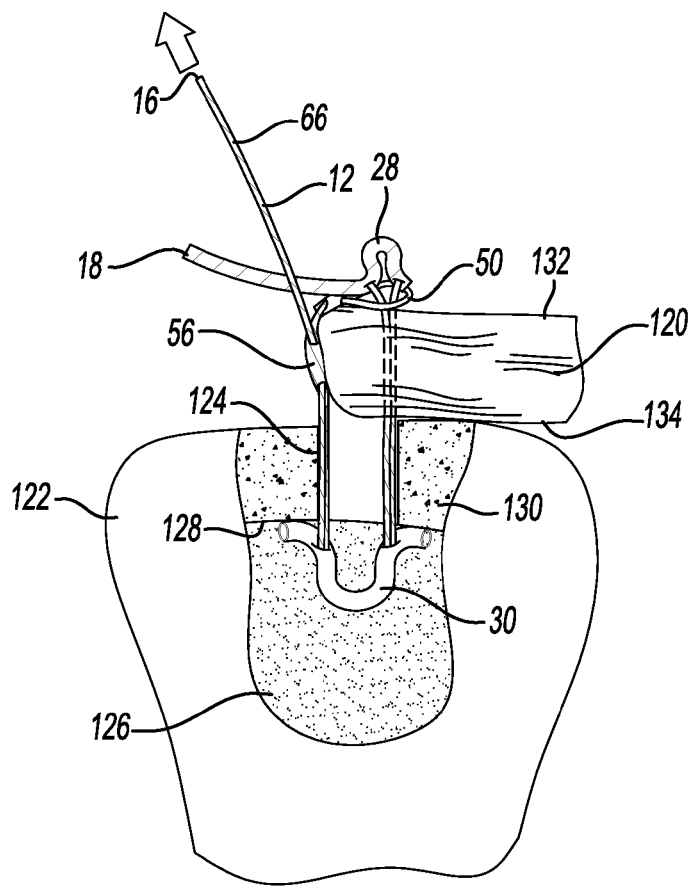

With additional reference to FIGS. 8A and 8B, another method for securing the rotator cuff tissue 120 to the humerus 122 will now be described. As illustrated, bone hole 124 is formed in the humerus 122 laterally offset from an edge 136 of the tissue 120. The first portion 66 of the suture tail 12 is passed through the tissue 120 such that the first end 16 is first inserted into the inner surface 134 and then is pushed or pulled out from the outer surface 132, as illustrated in FIG. 8B. The anchor 30 is implanted in the bone hole 124 either before or after the first portion 66 of the suture tail 12 is passed through the tissue 120. After the anchor 30 is implanted, the first end 16 of the suture tail 12 is inserted through the first adjustable suture loop 50 (FIG. 8B), the suture construct 14 is pulled and carried through the anchor 30 (FIG. 8C), and the suture construct 14 is tightened to secure the tissue 120 to the humerus 122 (FIG. 8D). As illustrated in FIGS. 8C and 8D, pulling the suture construct 14 through the anchor 30 and tightening the suture construct 14 pulls and stretches the tissue 120 in the medial to lateral direction. The suture construct 14 is tightened and the tissue 120 is tensioned by pulling the second end 60 of the suture construct 14. Excess portions 88 of the suture construct 14 and excess portions 90 of the suture tail 12 can then be cut and removed.

Figure 9:
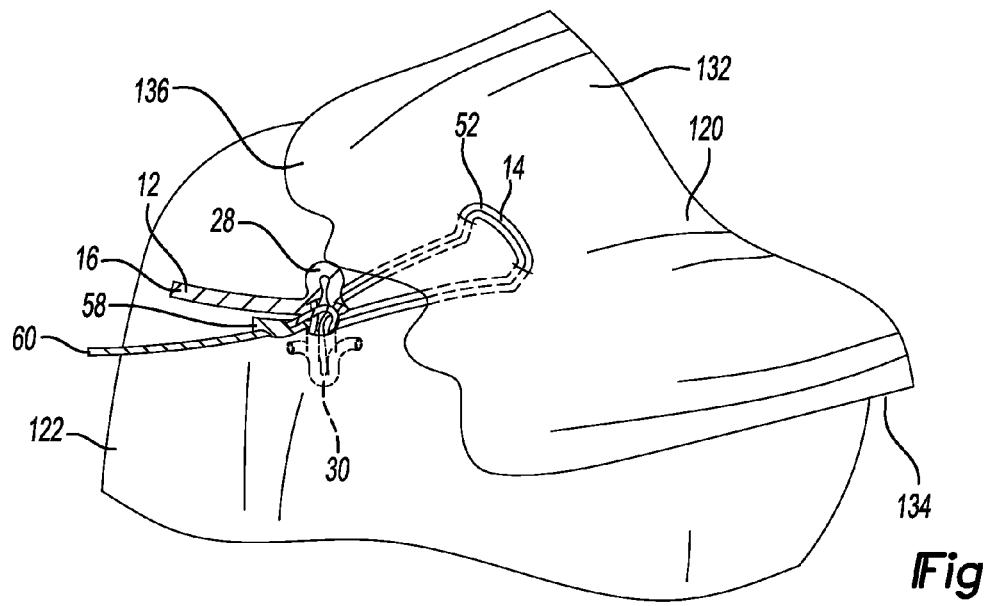
FIG. 9 illustrates an additional arrangement of the knotless suture anchor device of FIG. 1A for coupling tissue to bone.

With reference to FIG. 9, another way in which the rotator cuff tissue 120 can be secured to the humerus 122 is illustrated. The anchor 30 is implanted in the bone hole 124 formed either under the tissue 120 or laterally offset therefrom. The first end 16 of the suture tail 12 is then passed through the tissue 120 from the inner surface 134 to the outer surface 132, and then back through the tissue 120 through the outer surface 132 and out the inner surface 134. The first end 16 is inserted through the first adjustable suture loop 50 and the suture construct 14 is pulled through the tissue 120 along the same path that that the suture tail 12 was inserted. The second end 60 of the suture construct 14 is then pulled to tension the tissue 120 and secure the tissue 120 to the humerus 122.

Figure 10:
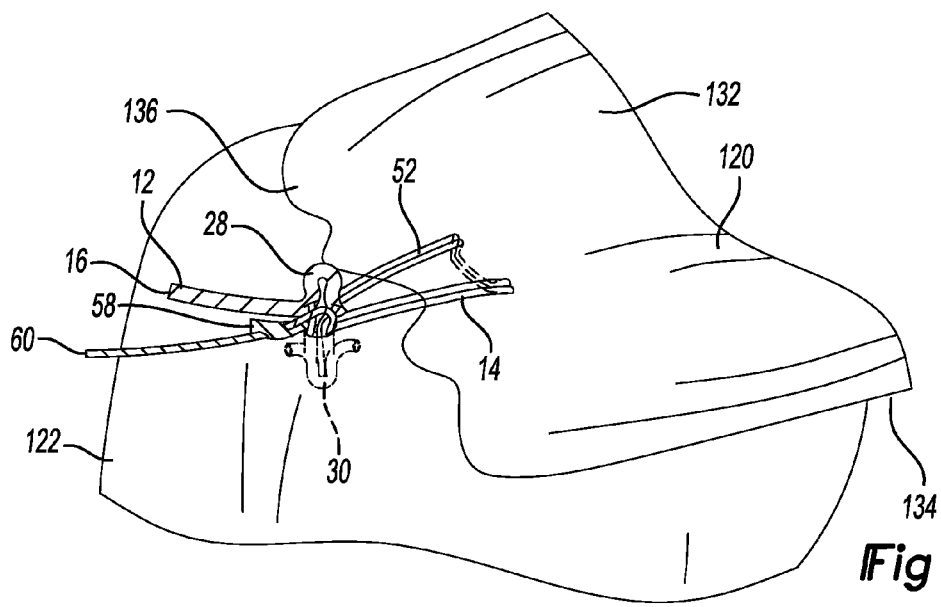
FIG. 10 illustrates yet another arrangement of the knotless suture anchor device of FIG. 1A for coupling tissue to bone.

An additional way to secure the tissue 120 to the humerus 122 is illustrated in FIG. 10. The configuration of FIG. 10 is similar to that of FIG. 9, except that the suture tail 12 is passed through the tissue 120 in the opposite direction. Specifically, the first end 16 of the suture tail 12 is inserted into the tissue 120 at the outer surface 132, through the tissue 120 such that the first end 16 exits the tissue 120 at the inner surface 134, back into the tissue 120 at the inner surface 134, and out from within the tissue 120 at the outer surface 132. The first end 16 of the suture tail 12 is then inserted through the first adjustable suture loop 50 and the suture construct 14 is pulled through the tissue 120 along the path that the suture tail 12 was inserted. The suture construct 14 is tightened against the tissue 120, and the tissue 120 is tensioned against the humerus 122, by pulling the second end 60 of the suture construct 14.

Figure 11A:
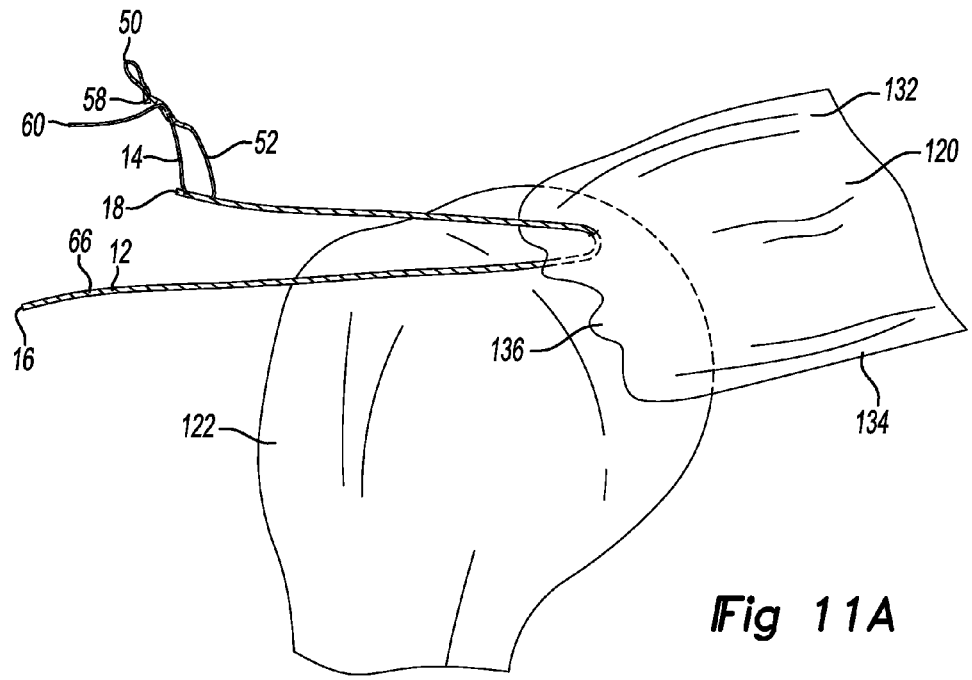
FIGS. 11A-11E illustrate yet another method for coupling tissue to bone using the knotless suture anchor device of FIG. 1A.
Figure 11B:
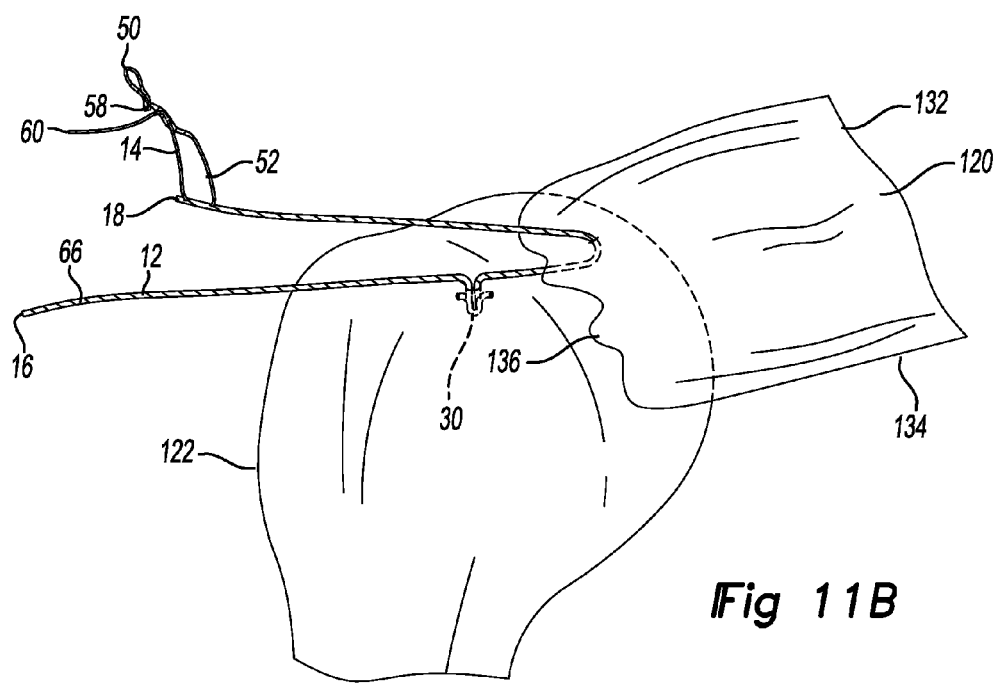

FIGS. 11A-11E illustrate another way to use the knotless suture anchor device 10 to secure the tissue 120 to the humerus 122. With initial reference to FIG. 11A, the first end 16 of the suture tail 12 is first passed through the tissue 120. The first end 16 is inserted into the outer surface 132 of the tissue 120, pushed or pulled through the tissue 120, and then pulled out of the tissue 120 at the inner surface. The first anchor 30 is added to the first portion 66 of the suture tail 12 in any suitable manner, such as described in the '304 application. The first anchor 30 is implanted in the humerus 122 in any suitable manner using any suitable insertion device, such as those described herein or in the '304 application. FIG. 11B illustrates the first anchor 30 implanted in the humerus.

Figure 11C:
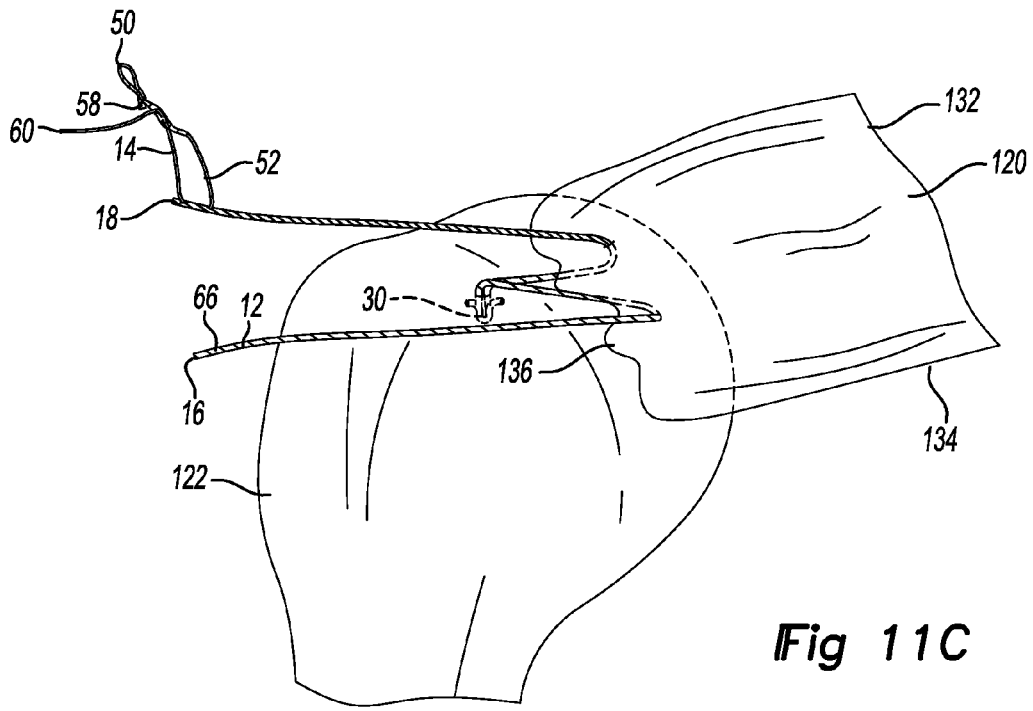
Figure 11D:
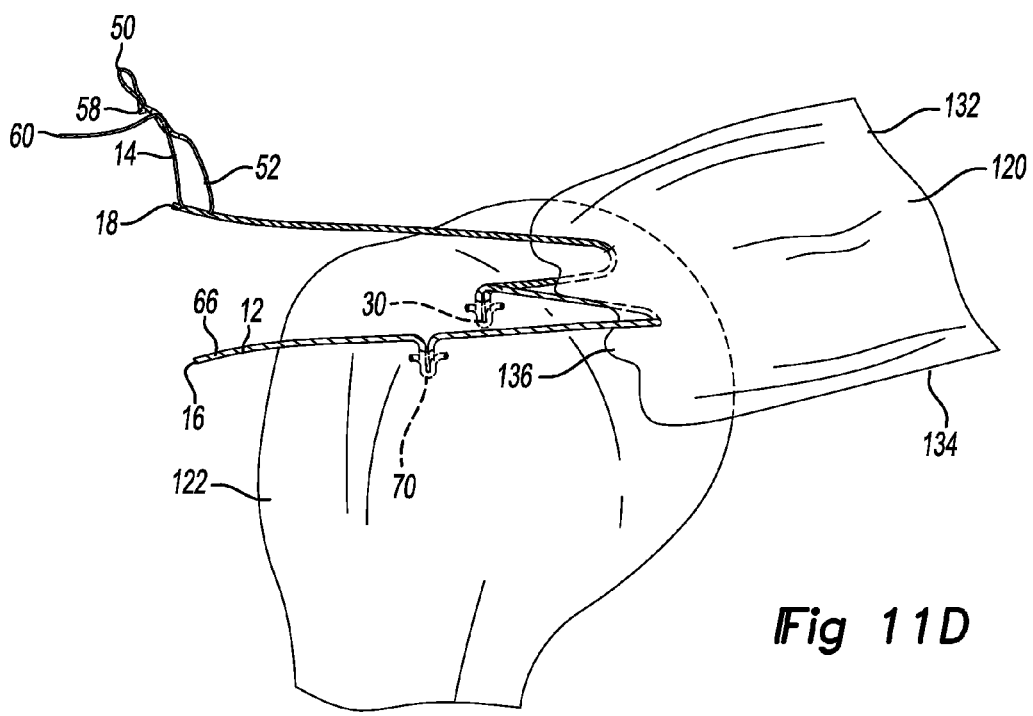

With additional reference to FIG. 11C, the first end 16 of the suture tail 12 is again inserted through the tissue 120. This time the first end 16 is inserted into the tissue 120 at the inner surface 134 and passed through the tissue 120 such that the suture tail 12 exits from the outer surface 132 of the tissue 120. With additional reference to FIG. 11D, the second anchor 70 is mounted to the first portion 66 of the suture tail 12 between the first end 16 and the tissue 120 in any suitable manner, such as described in the '304 application. The second anchor 70 is then implanted in the humerus 122. The suture tail 12 need not be passed through the tissue 120 for the second time. Thus, the suture tail 12 can extend from the first anchor 30 directly to the second anchor 70 without passing through the tissue 120 therebetween.

Figure 11E:
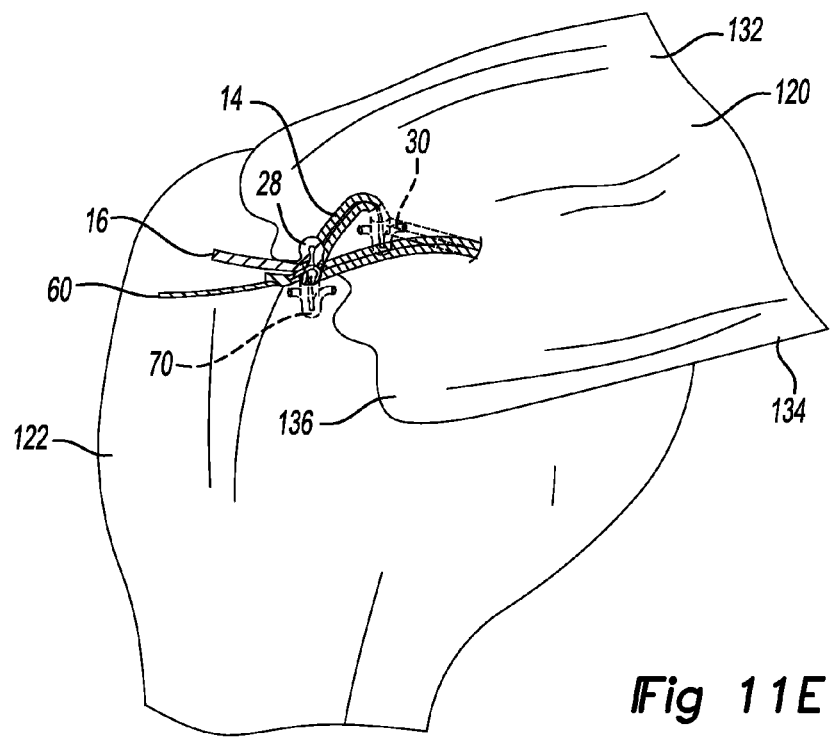

After the second anchor 70 is implanted, the first end 16 of the suture tail 12 is inserted through the first adjustable suture loop 50, and the suture tail 12 is pulled entirely through both the first anchor 30 and the second anchor 70 such that the suture construct 14 connects the tissue 120 to the first and the second anchors 30 and 70. The suture construct 14 is tightened by pulling on the second end 60 of the suture construct 14, which stretches and tensions the tissue 120 laterally. To further secure the suture construct 14, the first adjustable suture loop 50 can be slid away from the second body 56 to prevent the first adjustable suture loop 50 from passing over the locking member 28. FIG. 11E illustrates the suture construct 14 in its final position with excess portions of the suture tail 12 and the second end 60 of the suture construct 14 removed.

Figure 12:
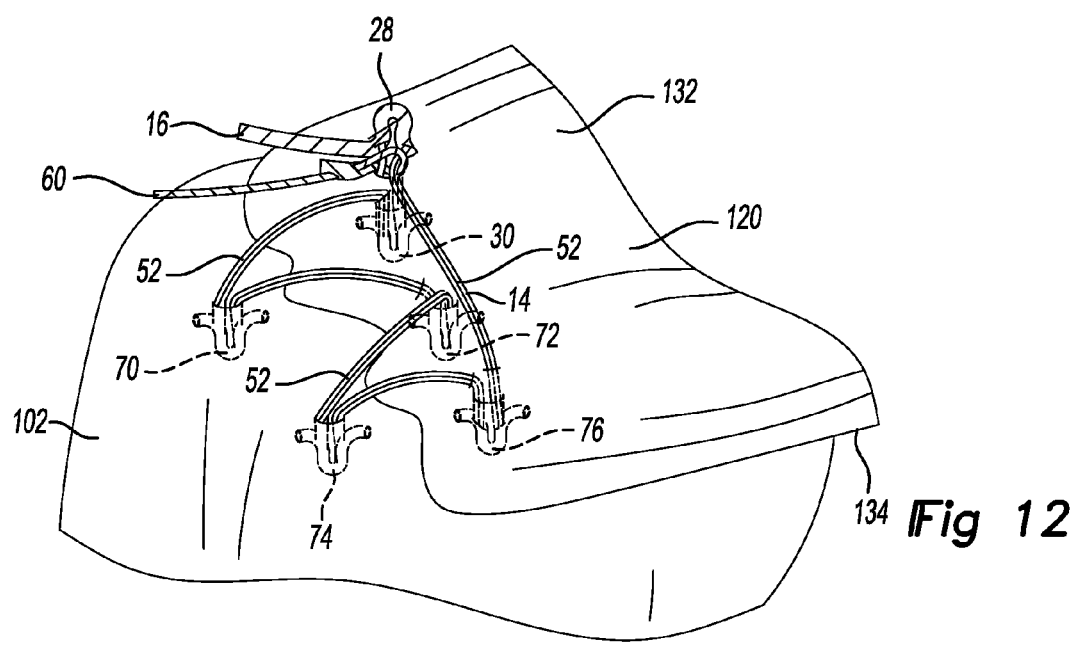
FIG. 12 illustrates a further arrangement of the knotless suture anchor device of FIG. 1A for coupling tissue to bone.

With additional reference to FIG. 12, the tissue 120 can be secured to the humerus 122 with more than two anchors. FIG. 12 illustrates five anchors, but any suitable number of anchors can be used. The anchors can be implanted in most any suitable arrangement. For example, anchors 30, 72, and 76 can be arranged medially and generally in alignment in the anterior to posterior direction. Anchors 70 and 74 can be arranged laterally and also aligned in the anterior to posterior direction. The second adjustable suture loop 52 can be connected to the anchors 30, 70, 72, 74, and 76 in any suitable pattern and configuration. For example, and as illustrated in FIG. 12, the second adjustable suture loop 52 can be arranged in an overlapping configuration in which the second adjustable suture loop 52 overlaps the outer surface 132 between each of the anchors 30, 70, 72, 74, and 76. The second adjustable suture loop 52 is threaded through the tissue 120 and secured thereto in the same manner described above with respect to the other ways in which the knotless suture anchor device 10 can be used to fasten the tissue 120 to the bone 102.

With additional reference to FIGS. 13A-13D, the knotless suture anchor device 10 can be used to secure two pieces of separated tissue together without anchoring the tissue to bone. Because the tissue is not anchored to bone, the device 10 does not include an anchor, such as the first anchor 30. Therefore, FIGS. 13A-13D the knotless suture anchor device 10 does not include an anchor at all.

With initial reference to 13A, a first tissue portion 140A and a second tissue portion 140B are illustrated. The first and second tissue portions 140A and 140B are separated to define a space therebetween. The first tissue portion 140A includes an outer surface 142A and an inner surface 144A that is opposite to the outer surface 142A. Similarly, the second tissue portion 140B includes an outer surface 142B and an inner surface 144B that is opposite to the outer surface 142B.

Figure 13A:
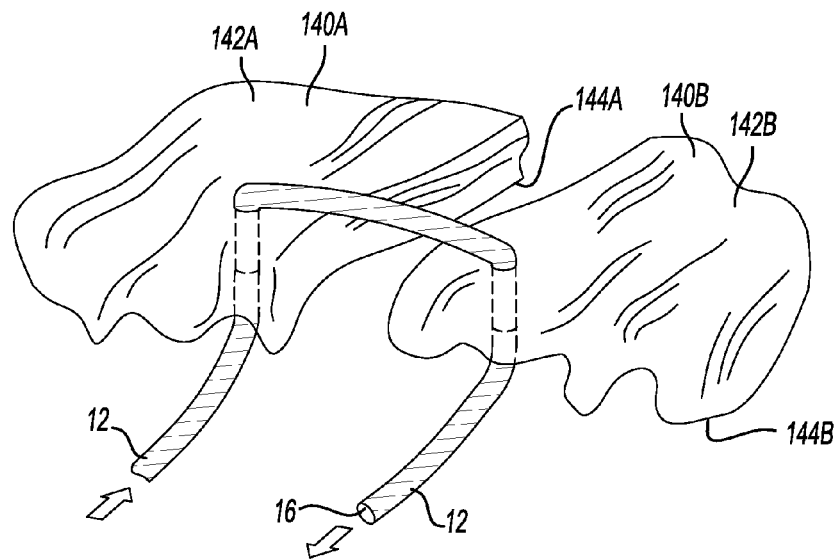
FIGS. 13A-13D illustrate a method for coupling two separated tissue portions using the knotless suture anchor device of FIG. 1A.
Figure 13B:
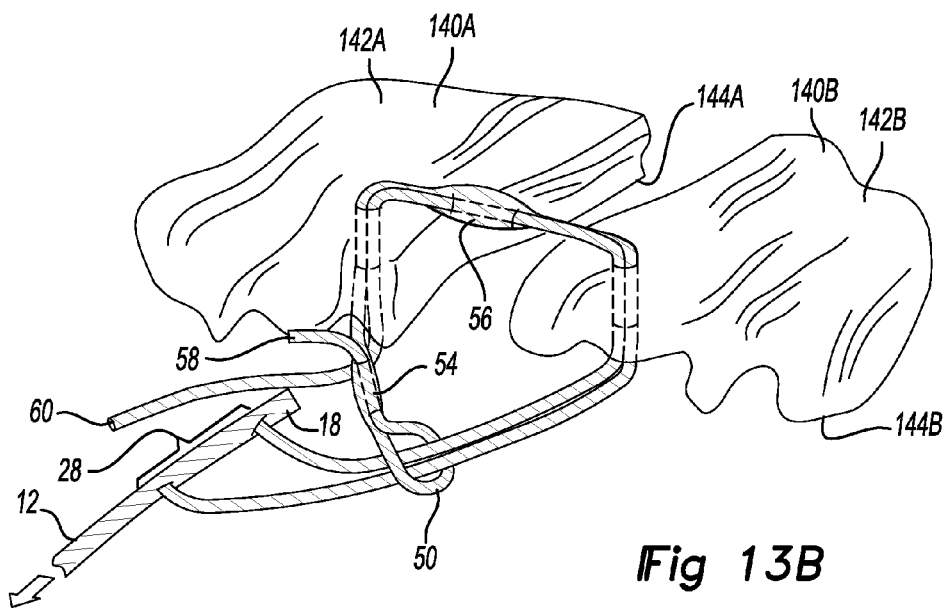
Figure 13C:
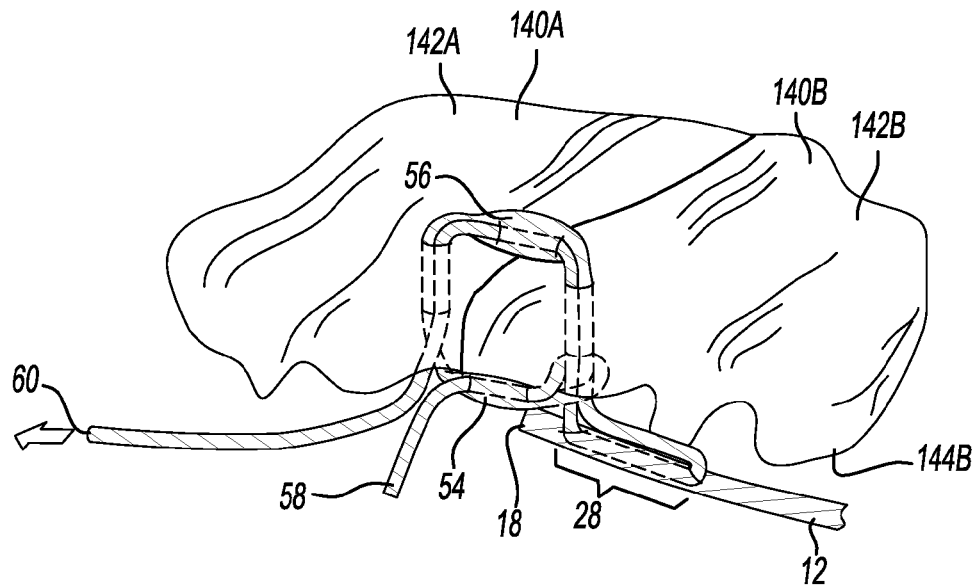
Figure 13D:
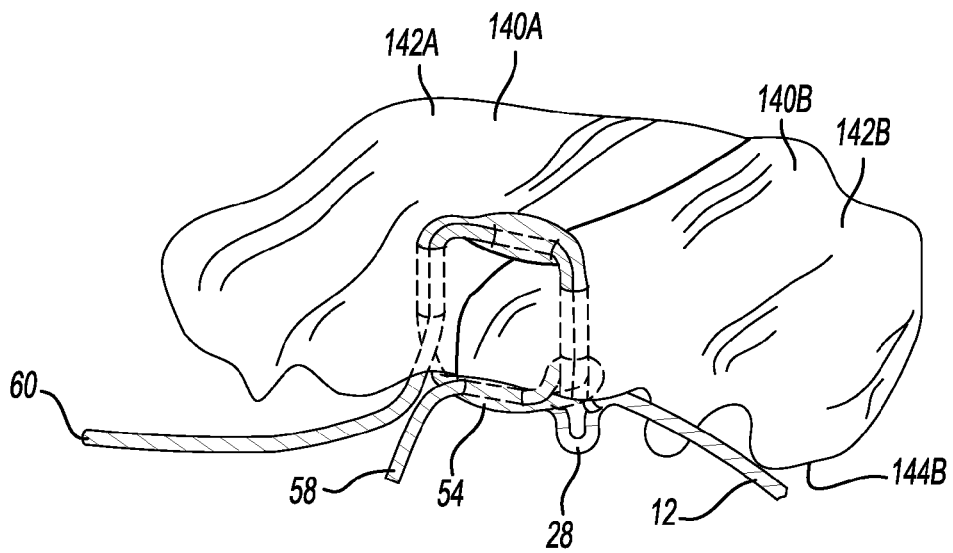

To secure the first and the second tissue portions 140A and 140B together, the first end 16 of the suture tail 12 is inserted into the inner surface 144A of the first tissue portion 140A, passed through the first tissue portion 140A, and pulled out from within the first tissue portion 140A at the outer surface 142A. From the outer surface 142A, the first end 16 is pulled across the space between the first and the second tissue portions 140A and 140B and passed through the second tissue portion 140B. The suture tail 12 enters the second tissue portion 140B at the outer surface 142B and exits the second tissue portion 140B at the inner surface 144B. The suture tail 12 is pulled entirely through both the first and second tissue portions 140A and 140B and passed through the first adjustable suture loop 50. Passing the suture tail 12 entirely through the first and the second tissue portions 140A and 140B carries the suture construct through the first and the second tissue portions 140A and 140B and connects the suture construct 14 to the first and the second tissue portions 140A and 140B, as illustrated in FIG. 13B. The second adjustable suture loop 52 is tightened by pulling on the second end 60, which draws the first tissue portion 140A and the second tissue portion 140B together. To lock the first adjustable suture loop 50 onto the second adjustable suture loop 52, the first body 54 is pushed away from the second body 56 to close the first adjustable suture loop 50. This procedure is faster, stronger, and more readily reproducible than tying a knot. As illustrated in FIG. 13D, locking member 28 further secures the first adjustable suture loop 50 onto the second adjustable suture loop 52.

With additional reference to FIG. 14, an insertion device according to the present teachings is illustrated at reference numeral 202. The insertion device 202 generally includes a handle 204 and a rod or shaft 206 that extends from the handle 204. The handle 204 includes a proximal end 208 and a distal end 210. At an end of the rod 206 opposite to the handle 204 is a tip 212.

Figure 15:
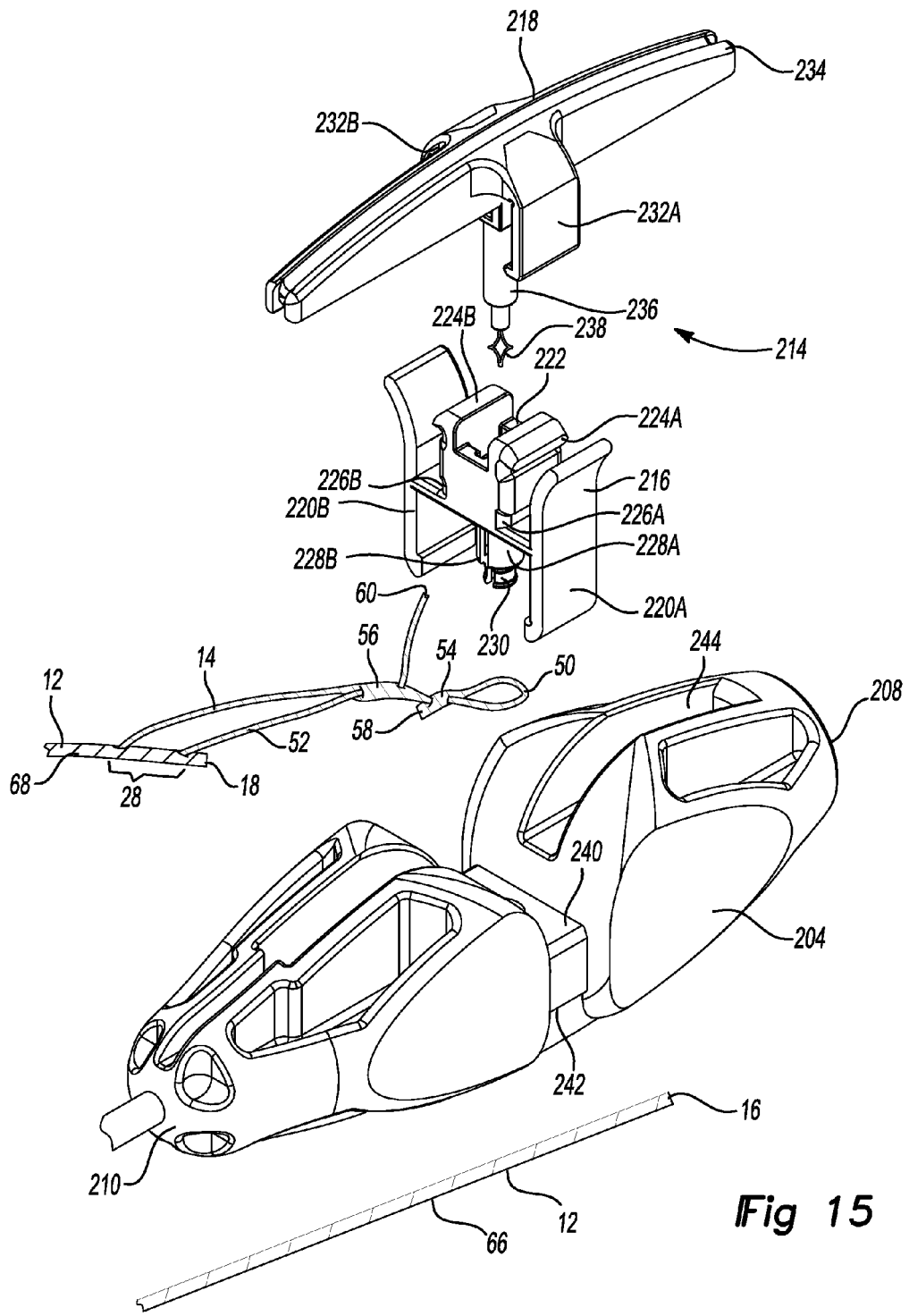
FIG. 15 is a perspective view of a handle and a suture retention assembly of the insertion device of FIG. 14.

With additional reference to FIG. 15, the insertion device 202 includes a suture retention assembly 214. The suture retention assembly 214 generally includes an anchor 216 and a passing device 218. The anchor 216 includes a first locking tab 220A and a second locking tab 220B at opposite sides of the anchor 216. Each of the first and the second locking tabs 220A and 220B are pivotable to permit the anchor 216 to be clipped onto the handle 204 and removed from the handle 204. Between the first and the second locking tabs 220A and 220B is a passing device retention member 222, which includes a first flange 224A and a second flange 224B on opposite sides thereof. The passing device retention member 222 further defines a first recess 226A and a second recess 226B on opposite sides of the passing device retention member 222. Extending from an undersurface of the anchor 216 opposite to the passing device retention member 222 is a first projection 228A and a second projection 228B. The first and second projections 228A and 228B are substantially similar to one another and face one another. They are both flexible, and biased to be compressed inward toward one another. Together, the first and the second projections 228A and 228B define a rim 230 at a distal end thereof. As further described herein, the rim 230 is configured for the first adjustable suture loop 50 to be secured thereto.

The passing device 218 includes a first clip 232A and a second clip 232B extending from opposite sides of an elongated grip 234. Between the first clip 232A and the second clip 232B is a post 236 with a ring 238 extending therefrom. The ring 238 can be made out of any suitable material having any suitable configuration that will suitable retain the suture tail 12 within the ring 238 when passed therethrough. For example, the ring 238 can be a flexible Nitinol™ ring. As further described herein, the passing device 218 is coupled with the anchor 216 such that the post 236 is seated between the first projection 228A and the second projection 228B to extend the first and the second projections 228A and 228B outward. The passing device 218 is also positioned such that the ring 238 extends beyond the rim 230. The passing device 218 is coupled to the anchor 216 in a first position through cooperation between the first clip 232A and the first recess 226A, and between the second clip 232B and the second recess 226B. The grip 234 can be moved to a second position by pulling on the grip 234 such that the first clip 232A abuts the first flange 224A and the second clip 232B abuts the second flange 224B. In the second position, the ring 238 is retracted into the first and the second projections 238A and 238B, and the post 236 is not between the first and the second projections 228A and 228B, thereby allowing the first and the second projections 228A and 228B to return to their contracted position, which will release the first adjustable suture loop 50 from the rim 230. As described further herein, when the suture tail 12 is inserted within the ring 238 and the grip 234 is moved from the first position to the second position, the suture tail 12 is pulled through the first adjustable suture loop 50.

With continued reference to FIG. 15, the suture retention assembly 214 is coupled to the handle 204 at recess 240, which is about equidistant between the proximal end 208 and the distal end 210. The first and the second locking tabs 220A and 220B extend over the flange 242 to couple the first and the second locking tabs 220A and 220B to the handle 204. When the suture retention assembly 214 is coupled to the handle 204, the grip 234 of the passing device 218 is seated within grip cutout 244 of the handle 204. To decouple the suture retention assembly 214 from the handle 204, the first and the second locking tabs 220A and 220B are pressed inward toward the passing device retention member 222, which causes the first and the second locking tabs 220A and 220B to disengage the flange 242.

Figure 16:
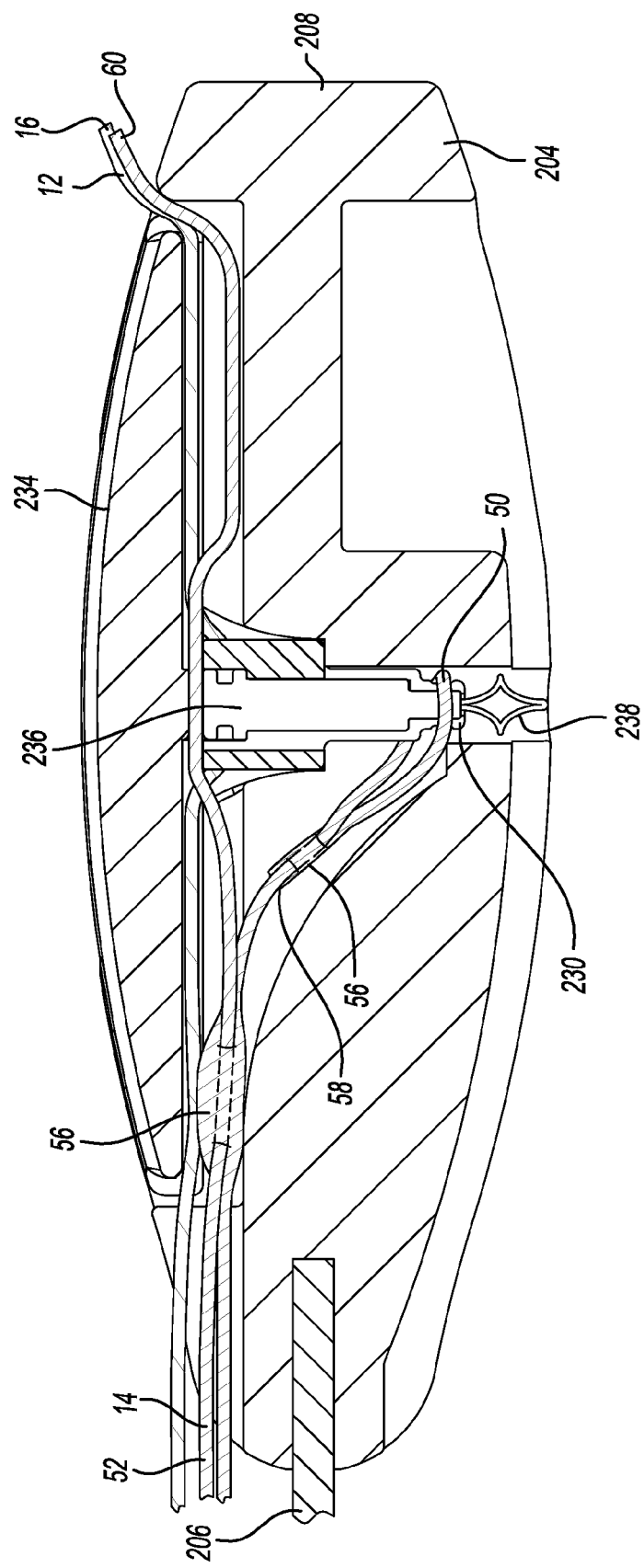
FIG. 16 is a cross-sectional view of the handle of the insertion device of FIG. 14 taken along line 16-16 of FIG. 14.

With additional reference to FIG. 16, connection of the knotless suture anchor device 10 to the insertion device 202 will now be described. The knotless suture anchor device 10 is mounted to the insertion device 202 such that the anchor 30 is at the tip 212 between two prongs of a forked portion 246. From the anchor 30, the first portion 66 of the suture tail 12 extends to the handle 204 and is seated under the grip 234 in the grip cutout 244. The suture construct 14 is also seated in the grip cutout underneath the grip 234. The first adjustable suture loop 50 is seated on the rim 230 such that the first and the second projections 228A and 228B extend through the first adjustable suture loop 50. The second end 60 of the suture construct 14 is also seated in the grip cutout 244 underneath the grip 234. The second end 60 extends towards the proximal end 208 of the handle 204 and at its tip can extend out from underneath the grip 234. The second end 60 can be fixedly secured to the suture retention assembly 214 to facilitate passage of the first end 16 through the first adjustable suture loop 50, as further described herein.

Figure 17A:
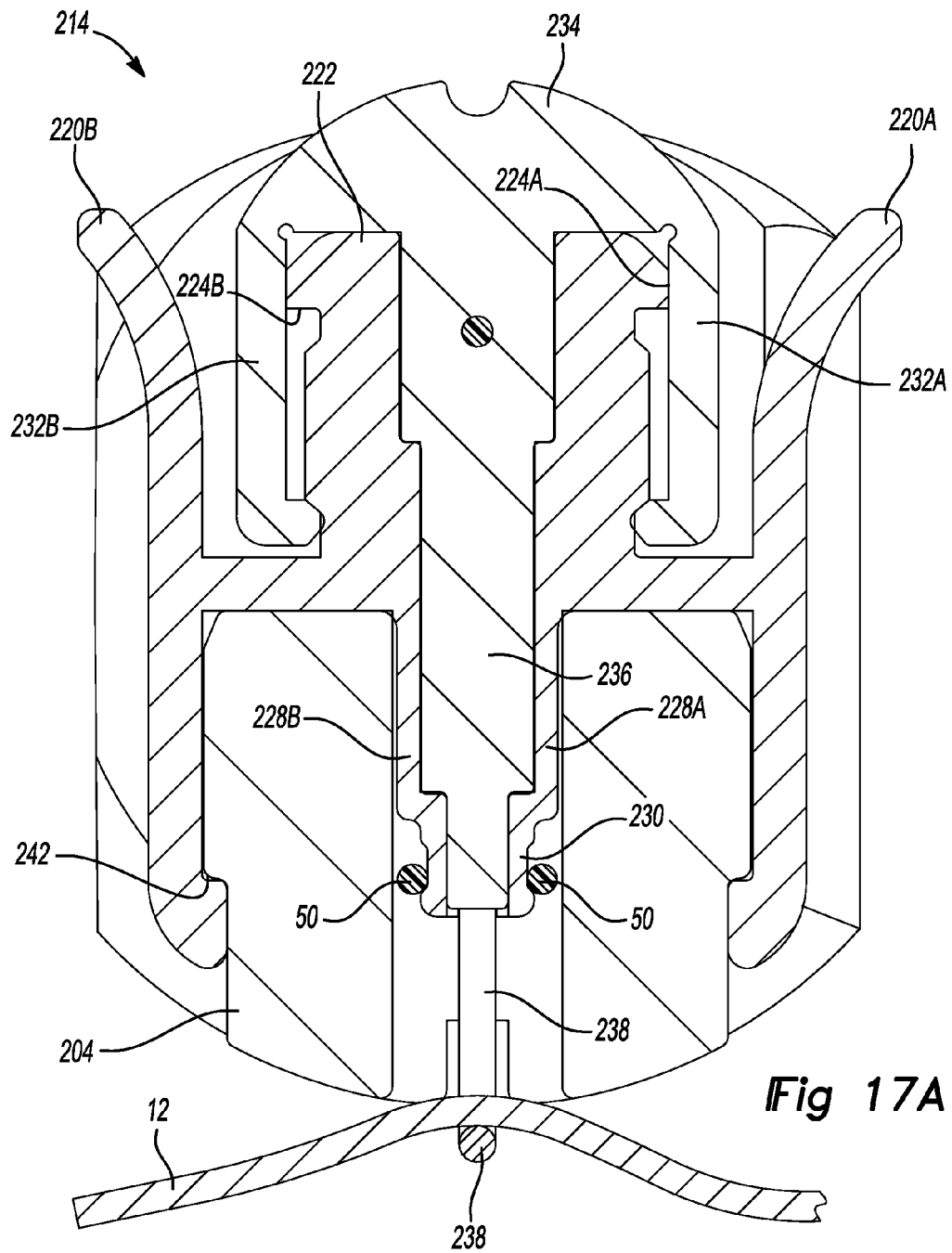
FIG. 17A is a cross-sectional view taken along line 17A-17A of FIG. 14 of the suture retention assembly of the insertion device of FIG. 14 in a first position.
Figure 17B:
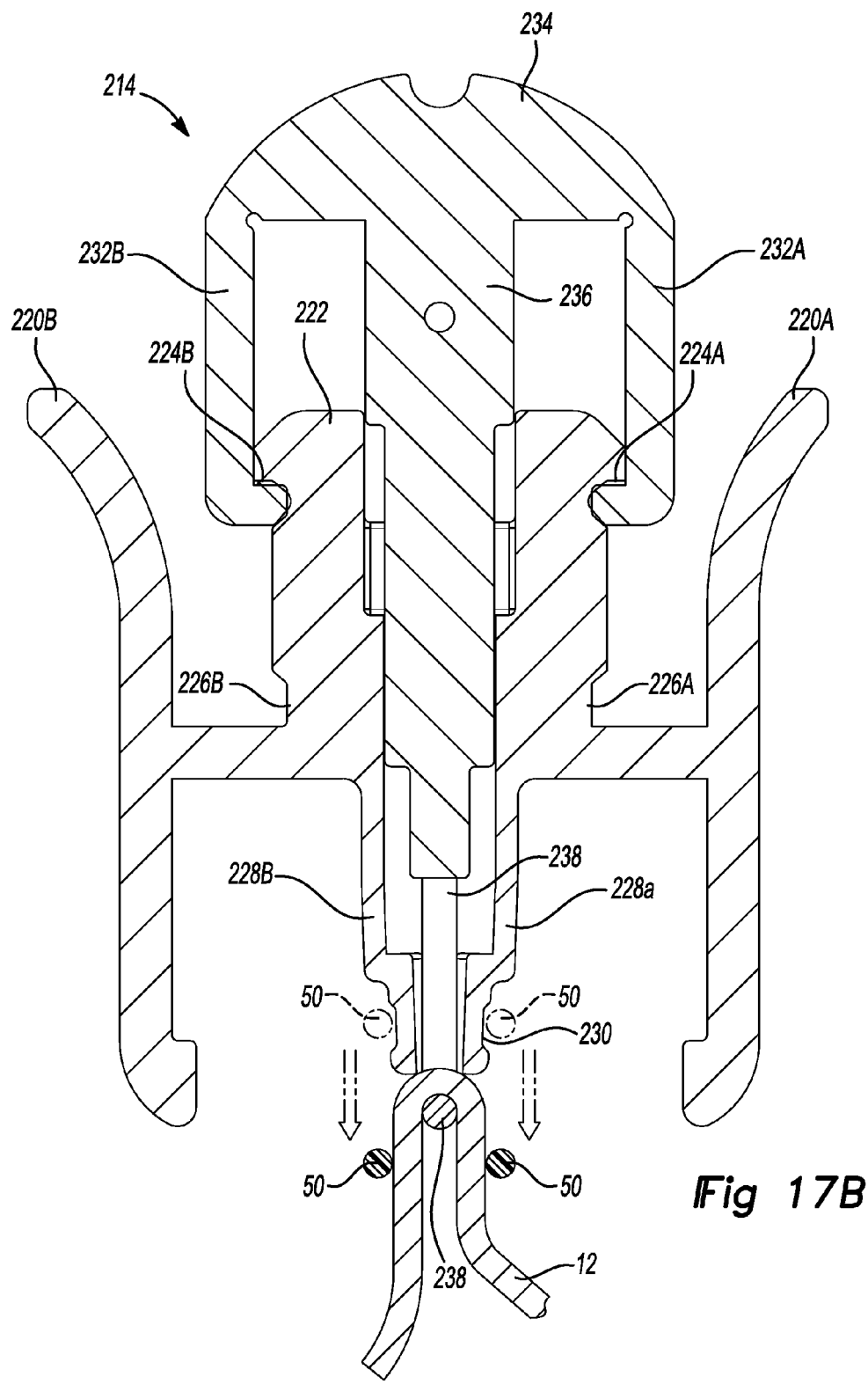
FIG. 17B is a cross-sectional view of the suture retention assembly in a second position.

With additional reference to FIGS. 17A and 17B, a cross-sectional view of the suture retention assembly 214 is illustrated. FIG. 17A illustrates the suture retention assembly 214 coupled to the handle 204. The suture retention assembly 214 is in the first position and the suture tail 12 is arranged such that it extends through the ring 238. With reference to FIG. 17B, the suture retention assembly 214 is illustrated decoupled from the handle 204 and the grip 234 is pulled outward to place the suture retention assembly 214 in the second position such that the first and the second clips 232A and 232B are seated against the first flange 224A and the second flange 224B respectively. In the second position, the post 236 and ring 238 pull the suture tail 12 into the first adjustable suture loop 50. The post 236 also no longer biases the first and the second projections 228A and 228B outward, thereby allowing the first and the second projections 228A and 228B to return to their biased inward positions and facilitate release of the first adjustable suture loop 50 from the rim 230.

With reference to FIGS. 18-23, use of the insertion device 202 to secure the tissue 104 to the bone 102 with the knotless suture anchor device 10 will now be described. The insertion device 202 can also be used to implant the knotless suture anchor device 10 to any other bone to secure any other type of tissue, such as a labrum as further described herein. The bone hole 110 can be formed in the bone 102 in any suitable manner using any suitable devices. Exemplary methods and device for forming the bone hole 110 are described in the '962 application, which is incorporated herein by reference.

Figure 18:
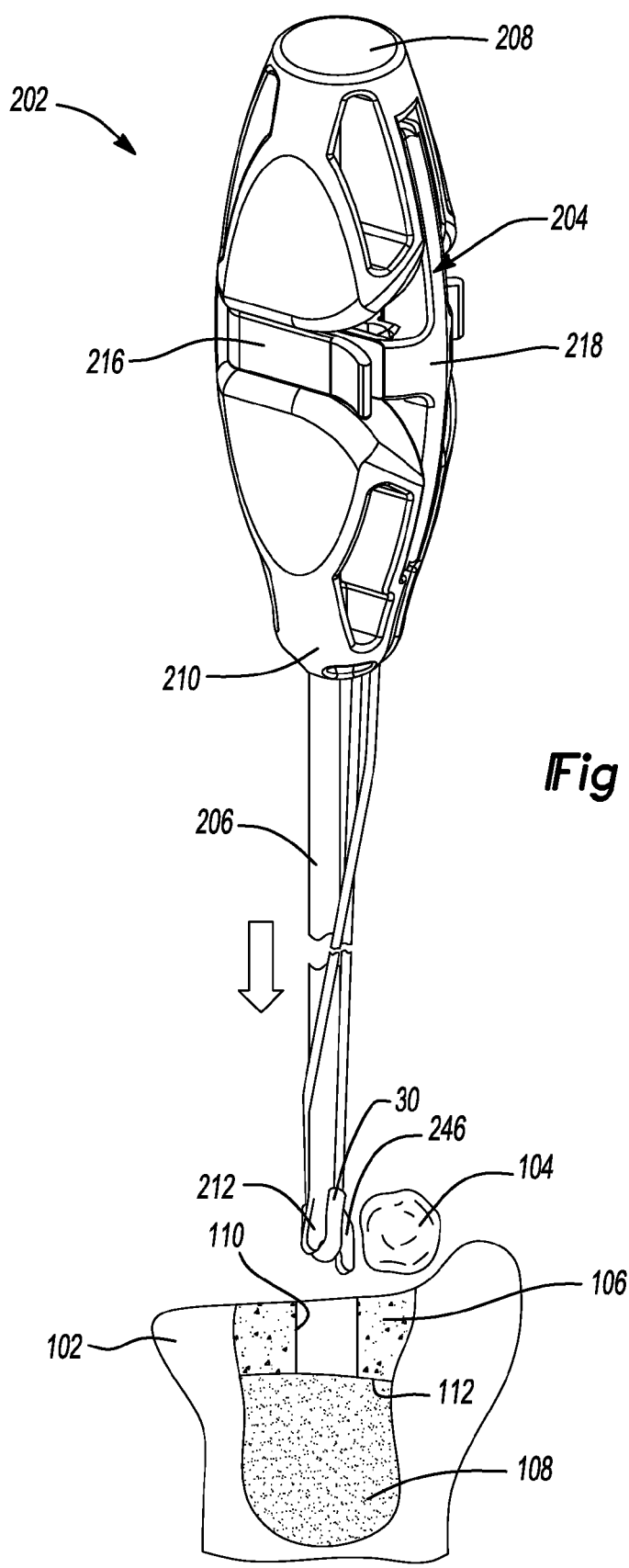

With initial reference to FIG. 18, with the knotless suture anchor device 10 mounted thereto, the insertion device 202 is aligned above the bone hole 110 and inserted into the bone hole 110 to implant the first anchor 30 in the inner cancellous bone layer 108 against the undersurface 112 of the outer cortical bone layer 106. With reference to FIG. 19, after the anchor 30 is positioned in the bone 102, the suture retention assembly 214 is disconnected from the handle 204. As the suture retention assembly 214 is disconnected, the first end 16 of the suture tail 12 is released from being clamped within the grip cutout 244, as is the suture construct 14. The first adjustable suture loop 50 remains coupled to the rim 230 of the first and the second projections 228A and 228B.

Figure 20:
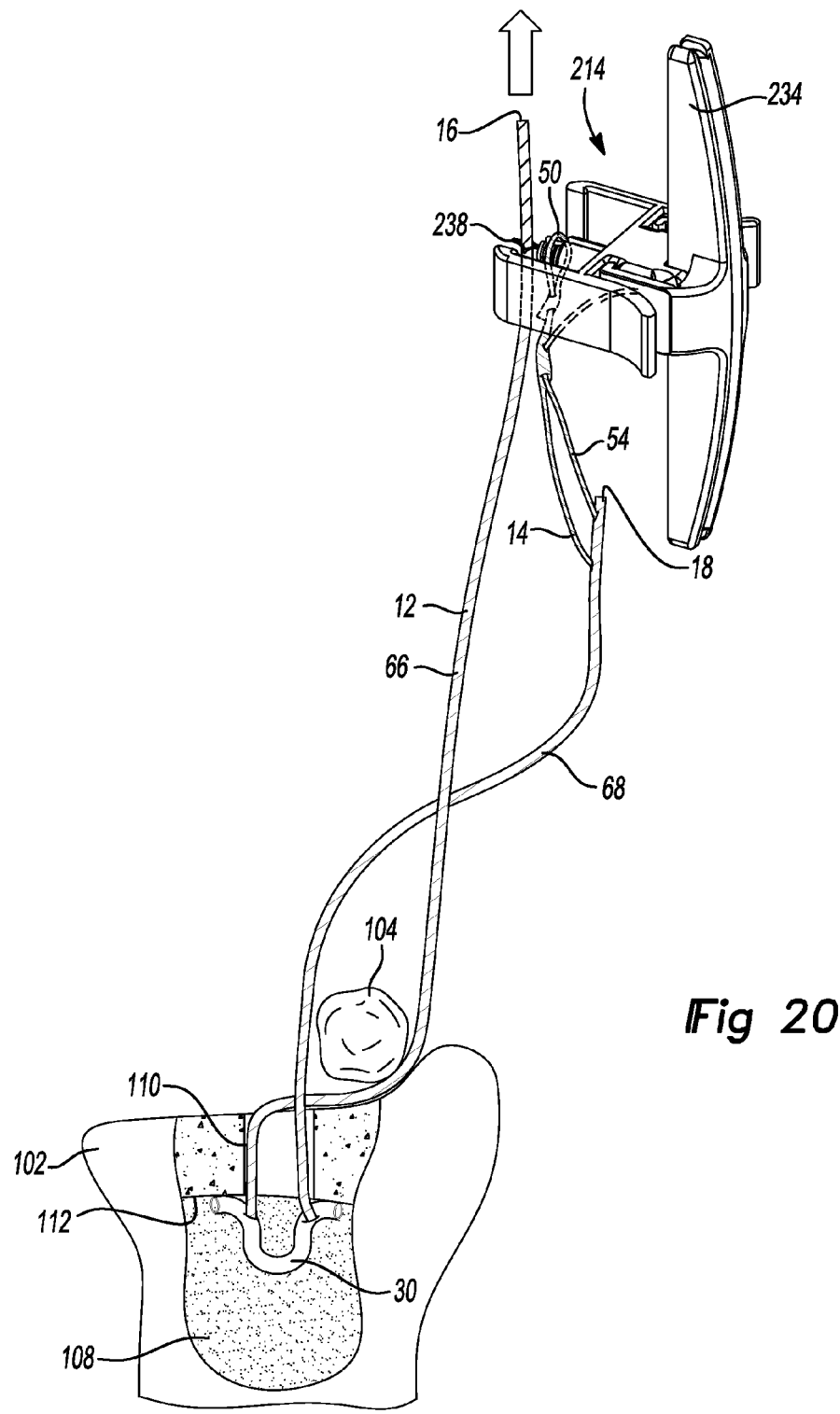
Figure 21:
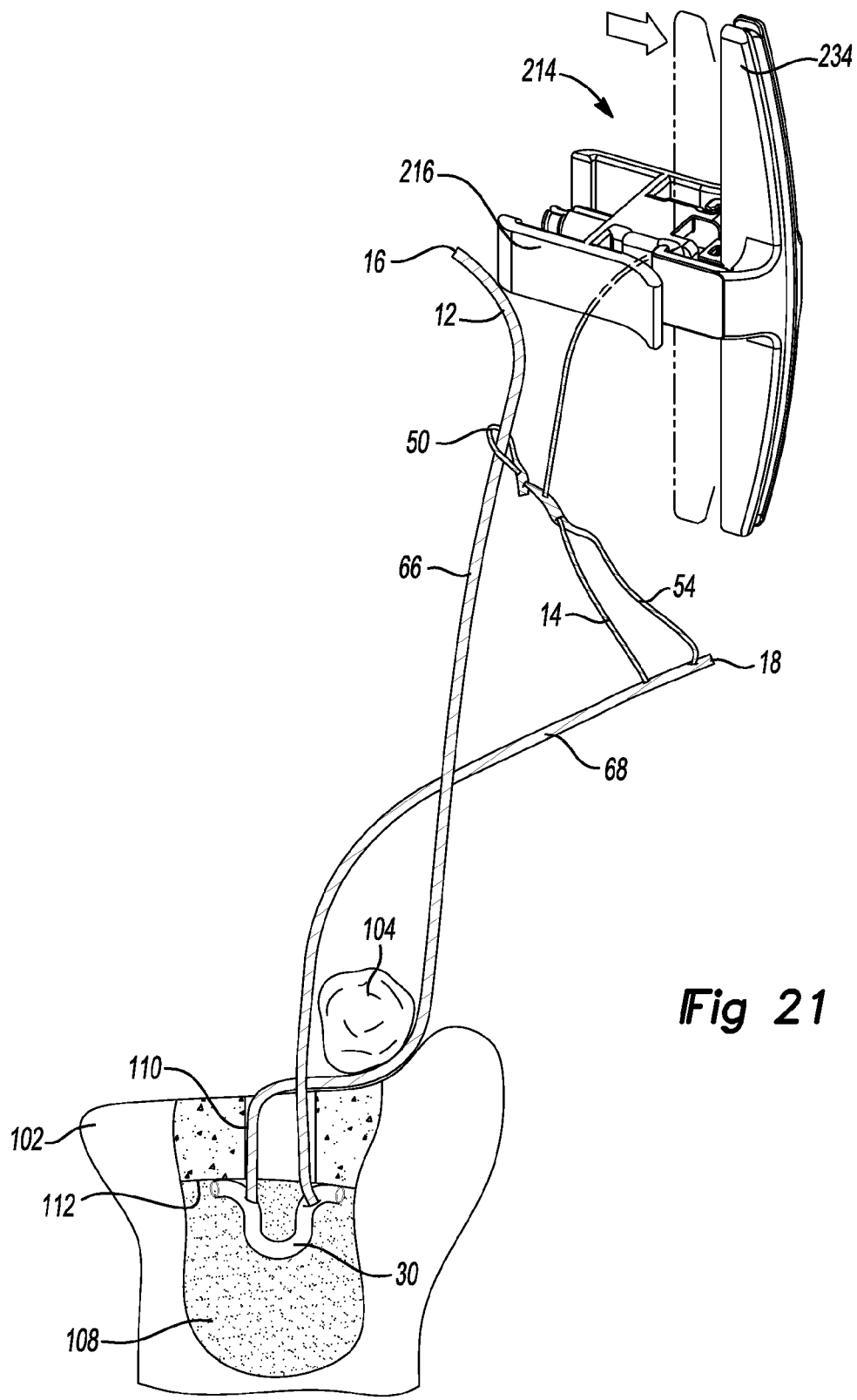

As illustrated in FIG. 20, the first portion 66 of the suture tail 12 is inserted through the ring 238 of the grip 234. The grip 234 is then moved from the first position to the second position in which the ring 238 is pulled in between the first and the second projections 228A and 228B to pull the first end 16 of the suture tail 12 into the first adjustable suture loop 50. As the post 236 of the grip 234 is pulled out from between the first and the second projections 228A and 228B, the first and the second projections 228A and 228B contract to facilitate release of the first adjustable suture loop 50 from the rim 230. As a result and as illustrated in FIG. 21, the suture tail 12 is threaded through the first adjustable suture loop 50, which decouples from the rim 230. The suture construct 14 remains connected to the suture retention assembly 214 by way of attachment of the second end 60 of the suture construct 14 to the suture retention assembly 214.

Figure 22:
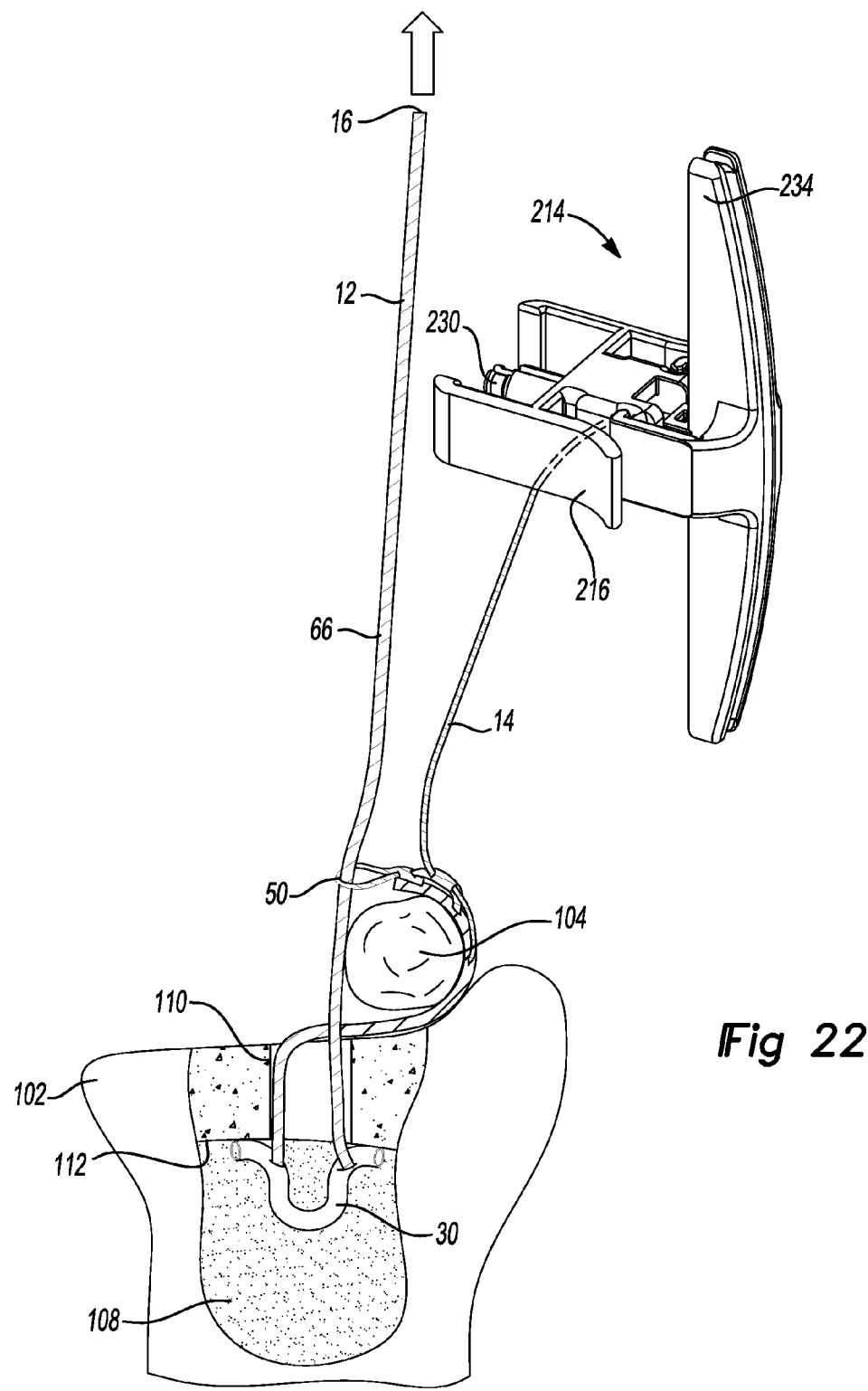
Figure 23:
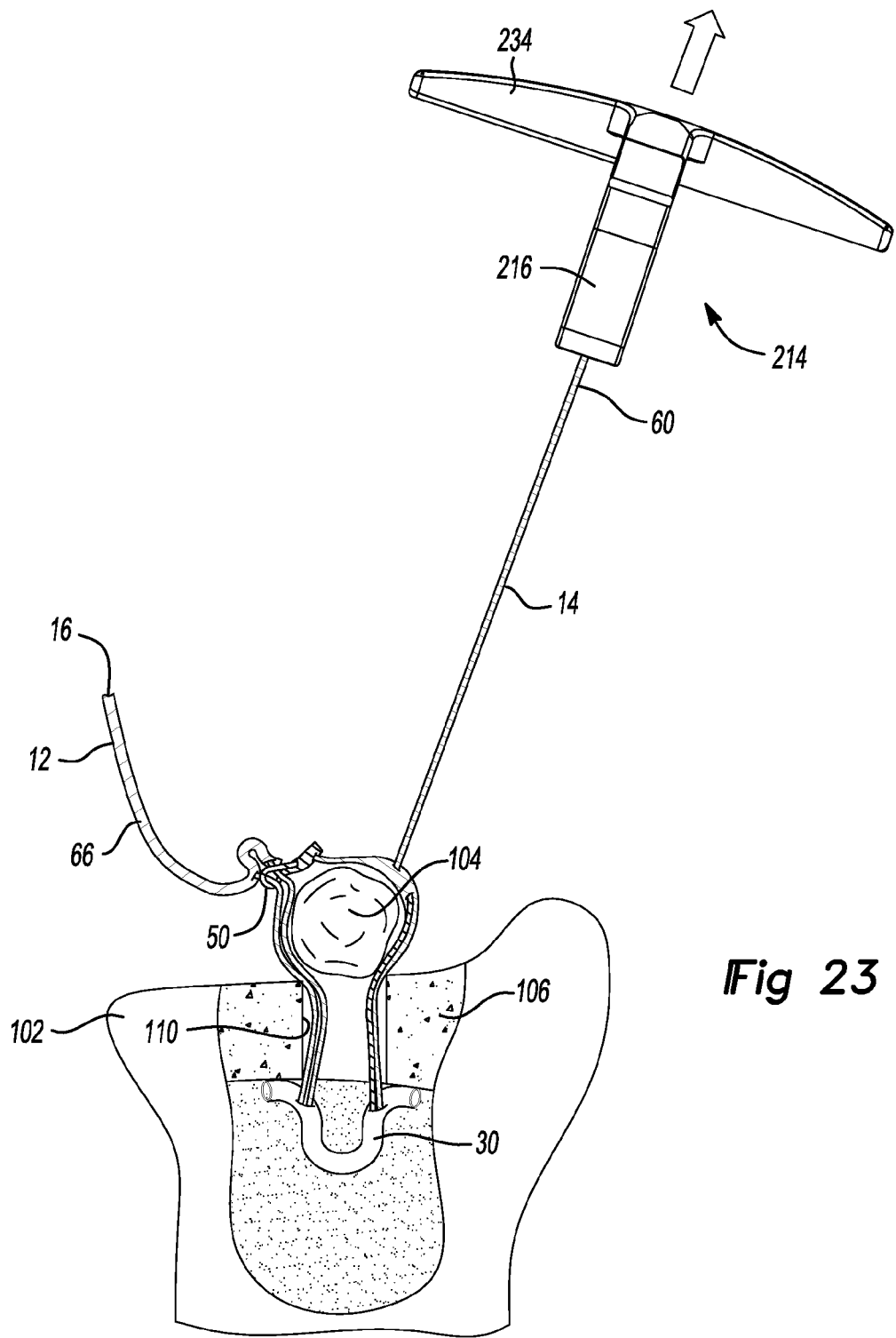

With additional reference to FIGS. 22 and 23, the suture tail 12 is pulled entirely through the anchor 30, thereby drawing the second adjustable suture loop 52 connected thereto into and through the internal passage 40 of the anchor 30. As a result, the suture construct 14 connects the tissue 104 to the anchor 30. Prior to tightening the second adjustable suture loop 52 to the tissue 104, the suture construct 14 can by adjusted about the tissue 102 by sliding the second adjustable suture loop 52 through the internal passage 40 of the anchor 30 because the internal passage 40 is dimensioned to permit the suture construct 14 to slide therethrough. To tighten the suture construct 14 against the tissue 104 and adjust the tension of the suture construct 14, the second end 60 of the suture construct 14 is pulled. Because the second end 60 is still secured to the suture retention assembly 214, pulling of the suture second end 60 can be facilitated by pulling on the grip 234 of the suture retention assembly. Once the suture construct 14 has been tensioned to a desired degree, excess portions 88 of the suture construct extending from the second passage portion 64 can be removed. Excess portions 90 of the suture tail 12 can be removed any time after the suture tail 12 is pulled through the anchor 30 and the first adjustable suture loop 50 is secured to the second adjustable suture loop 52.

Figure 24:
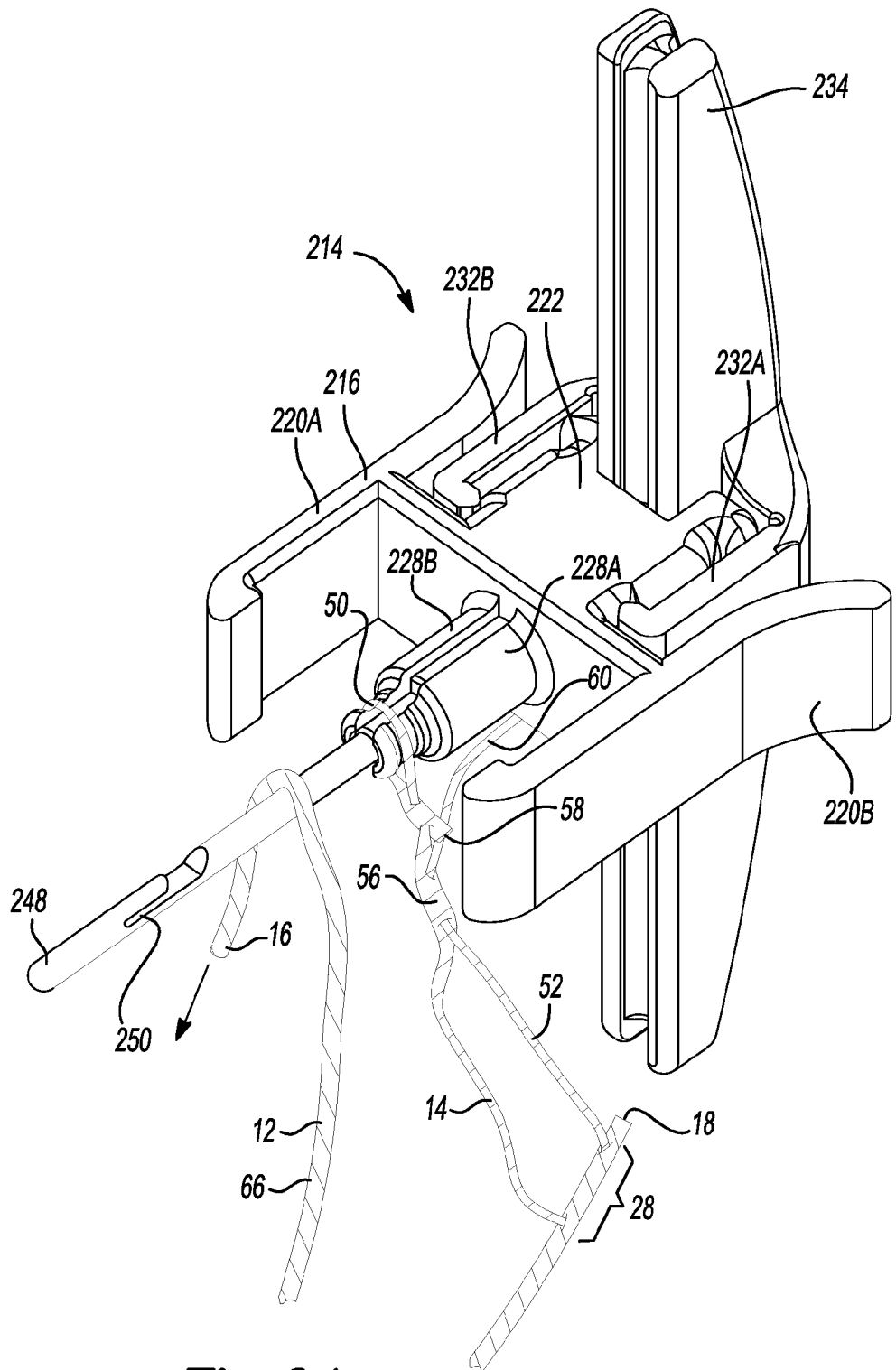
FIG. 24 is a perspective view of another suture retention assembly for the insertion device of FIG. 14.

With additional reference to FIG. 24, the suture retention assembly 214 can be modified to replace the ring 238 with a rod 248 defining a slot 250. The slot 250 is configured to receive and retain the suture tail 12 therein. The suture retention assembly 214 as illustrated in FIG. 24 will work the same way as the suture retention assembly 214 illustrated in FIGS. 14-23.

Figure 25:
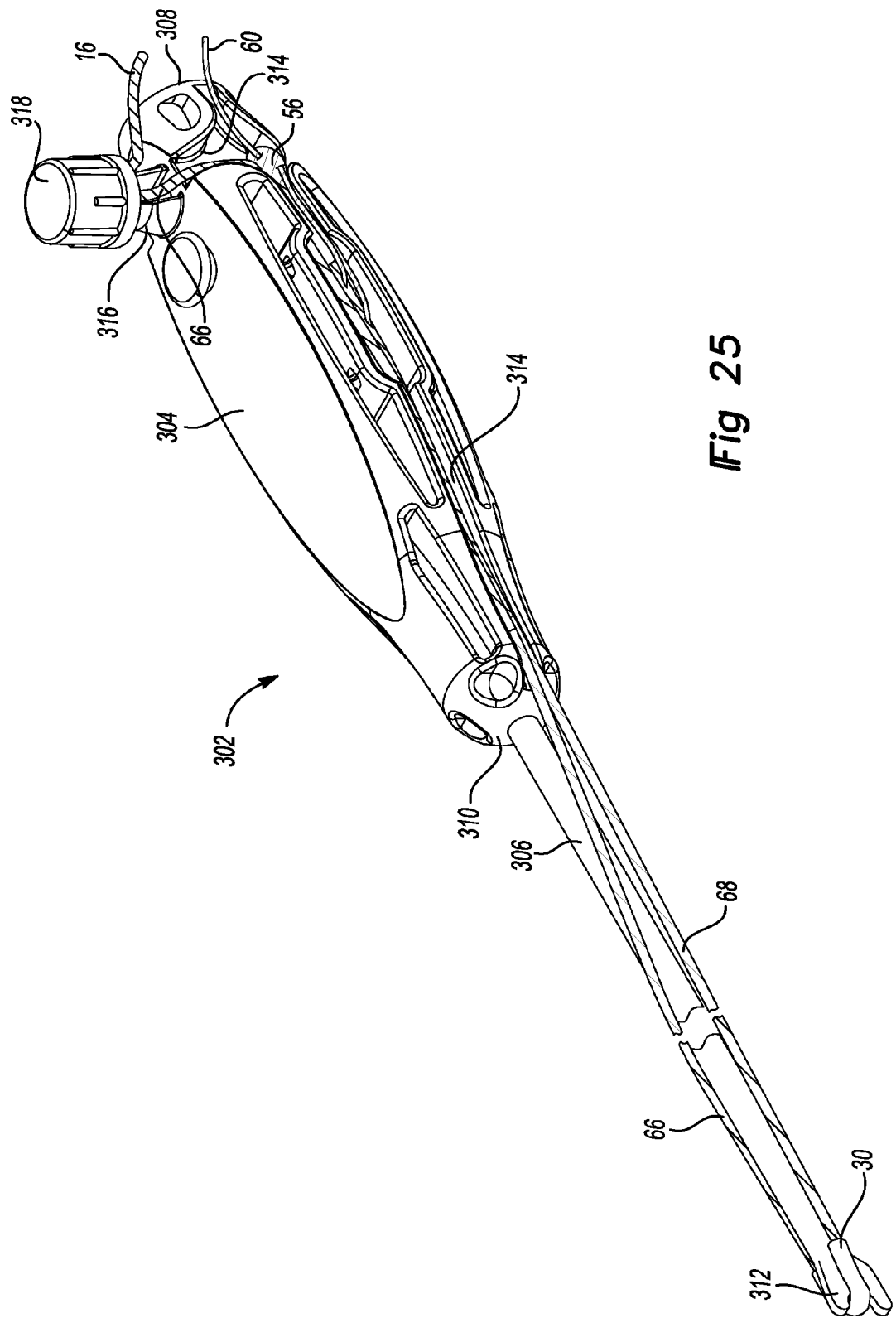
FIG. 25 is a perspective view of another insertion device according to the present teachings.
Figure 26:
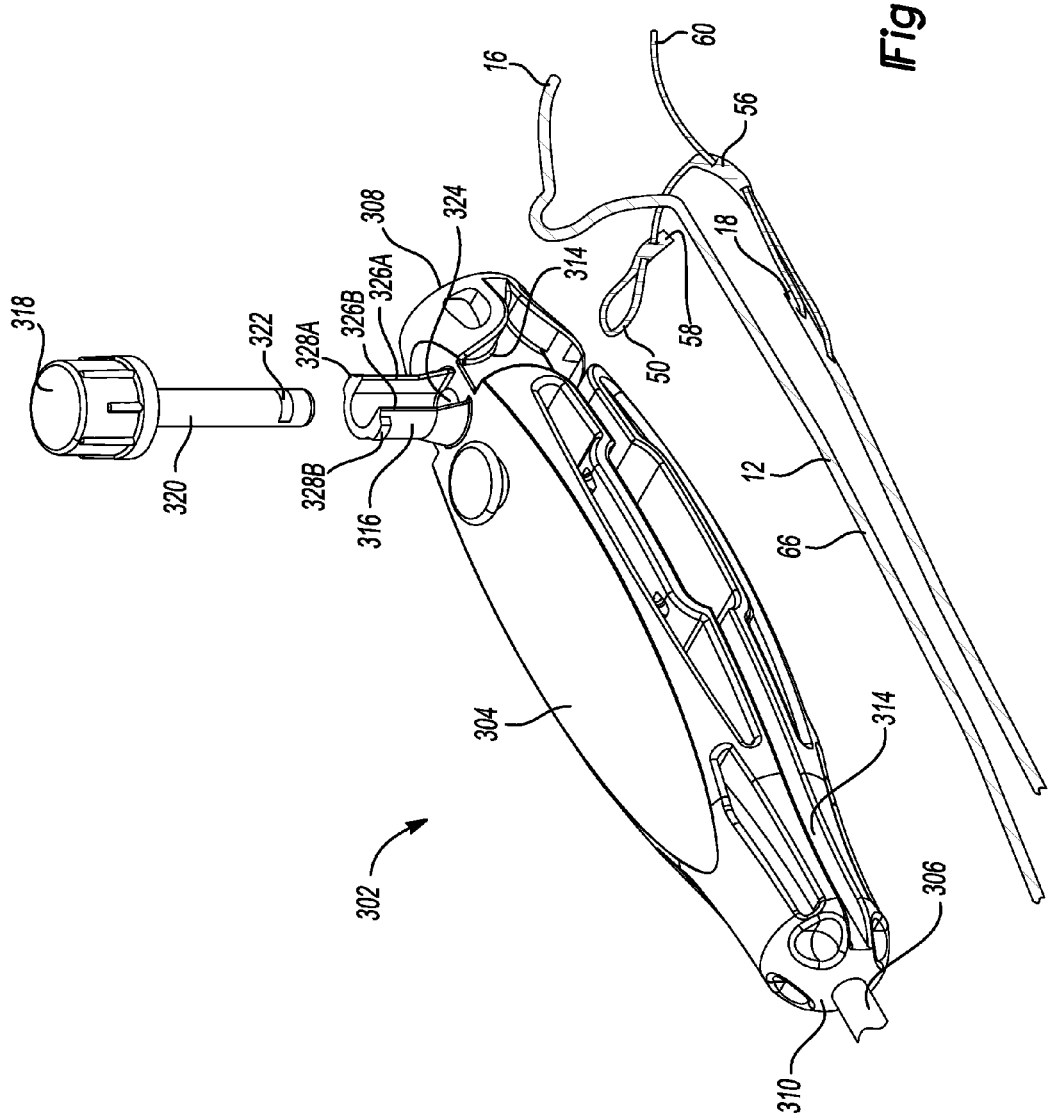
FIG. 26 is a perspective view of a handle of the insertion tool of FIG. 25.
Figure 27:
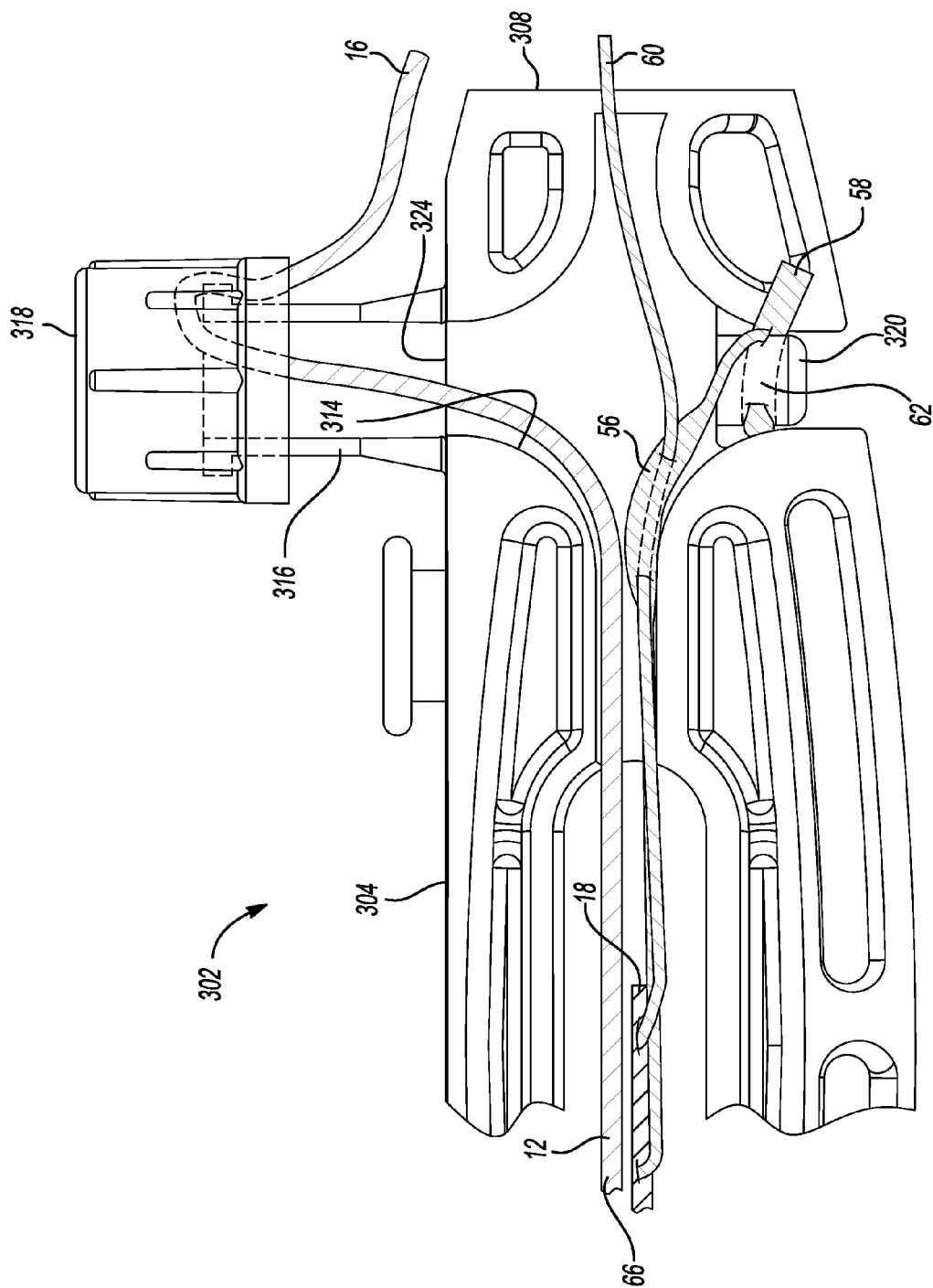
FIG. 27 is side view of the handle of the insertion tool of FIG. 25.

With additional reference to FIGS. 25-27, an additional insertion device is illustrated at reference numeral 302. The insertion device 302 generally includes a handle 304 and a rod 306 extending from the handle 304. The handle 304 includes a proximal end 308 and a distal end 310. The rod 306 extends from the distal end 310 and terminates at a tip 312 opposite to the distal end 310. The handle 304 defines a recess 314 that extends from the distal end 310 to the proximal end 308. The recess 314 also extends to a flange 316, which protrudes from the handle 304. A cap 318 can be fastened to the flange 316.

As illustrated in FIG. 26, extending from the cap 318 is a post 320 that defines an annular recess 322 at a distal end thereof. The post 320 is sized to be received within an aperture 324 of the handle 304. The aperture 324 is aligned with the flange 316 such that when the cap 318 is connected to the flange 316, the post extends through the aperture 324 to an opposite side of the handle 304, as illustrated in FIG. 27. The flange 316 includes a first edge 326A and a second edge 326B that is opposite to the first edge 326A. The first and the second edges 326A and 326B are spaced apart to define a gap therebetween. An end of the flange 316 opposite to the aperture 324 includes a first tab 328A and a second tab 328B.

The knotless suture anchor device 10 is mounted to the insertion device such that the anchor 30 is seated between forked portions 330 of the tip 312. Both the first portion 66 and the second portion 68 of the suture tail 12 extend from the anchor 30 to the handle 304 and are seated within the recess 314 of the handle 304. The first portion 66 of the suture tail 12 further extends through the aperture 324 and out of the flange 316, as illustrated in FIG. 27. When the cap 368 is connected to the flange 316, the first portion 66 of the suture tail 12 is pinched between the cap 318 and the flange 316 to retain the first portion proximate to the first end 16 at the flange 316. With further reference to FIG. 27, the first adjustable suture loop 50 is seated within the annular recess 322 of the post 320.

Insertion device 302 is used to implant the anchor 30 in bone in the same manner as that described above with respect to the insertion device 202. After the anchor 30 has been implanted, the cap 318 is disconnected from the flange 316 to release the first portion 66 of the suture tail 12 from being coupled to the handle 304. As the post 320 is pulled out from within the aperture 324, the first adjustable suture loop 50 will contact the handle 304 and be pushed out from within the annular recess 322, thereby detaching the suture construct from the post 320 and from the handle 304. Once detached from the handle 304, the knotless suture anchor device 10 can be freely used to secure a desired tissue to bone or two tissues together. For example, the anchor 30 can be implanted in the bone hole 110 using any suitable flexible anchor insertion device. The suture tail 12 is then threaded through the first adjustable suture loop 50 by hand, and the suture construct 14 is fastened to the desired tissue as described above in connection with FIGS. 1A through 6.

Figure 28:
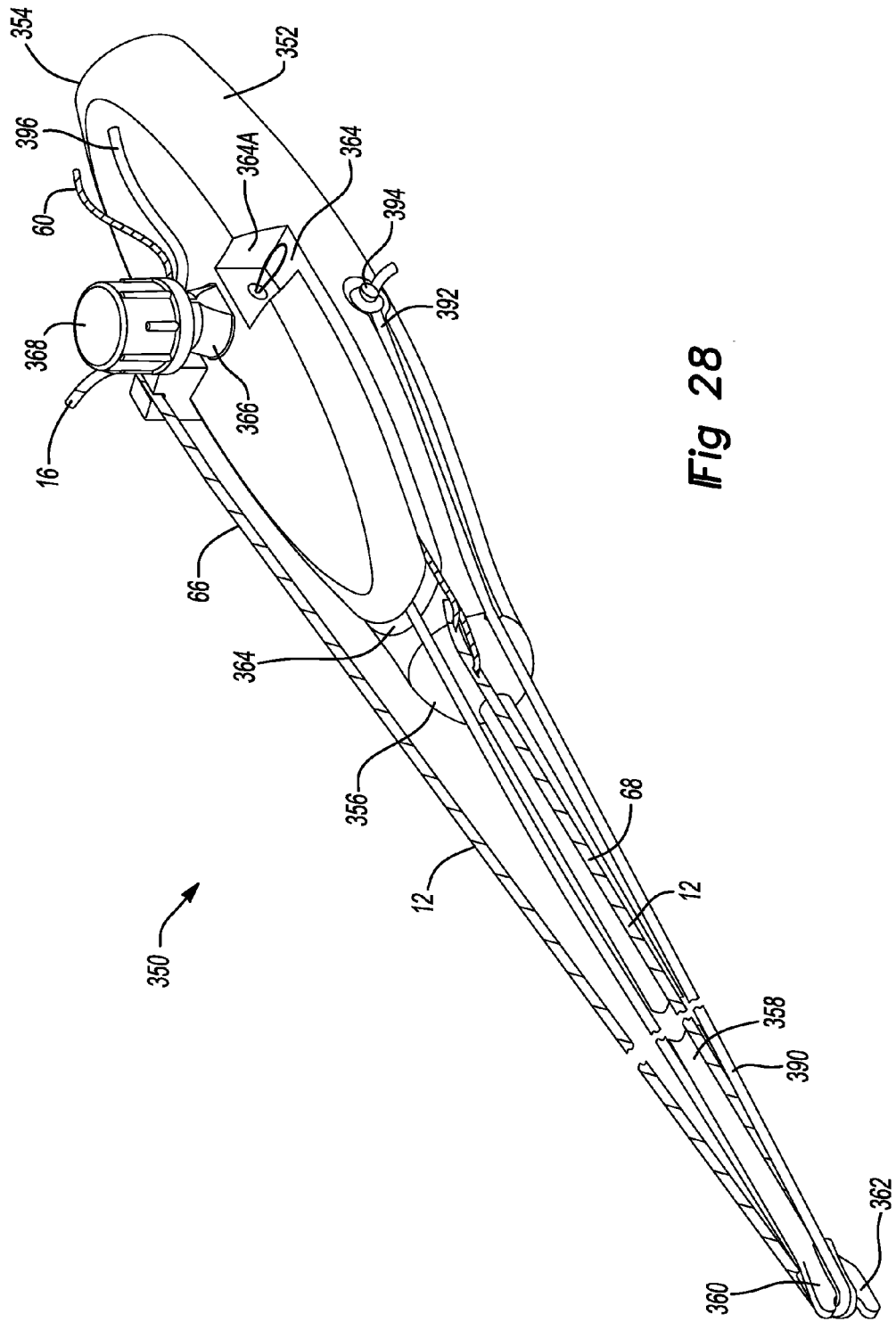
FIG. 28 is a perspective view of another insertion device according to the present teachings.

With general reference to FIGS. 28-32 and initial reference to FIG. 28, another insertion device according to the present teachings is illustrated at reference numeral 350. The insertion device 350 includes a handle 352 with a proximal end 354 and a distal end 356 that is opposite to the proximal end 354. A rod 358 extends from the distal end 356 of the handle 352. The rod 358 terminates opposite to the distal end 356 of the handle 352 at a tip 360. The tip 360 includes a forked portion 362 that provides a retention portion for the anchor 30, as further described herein.

Figure 29:
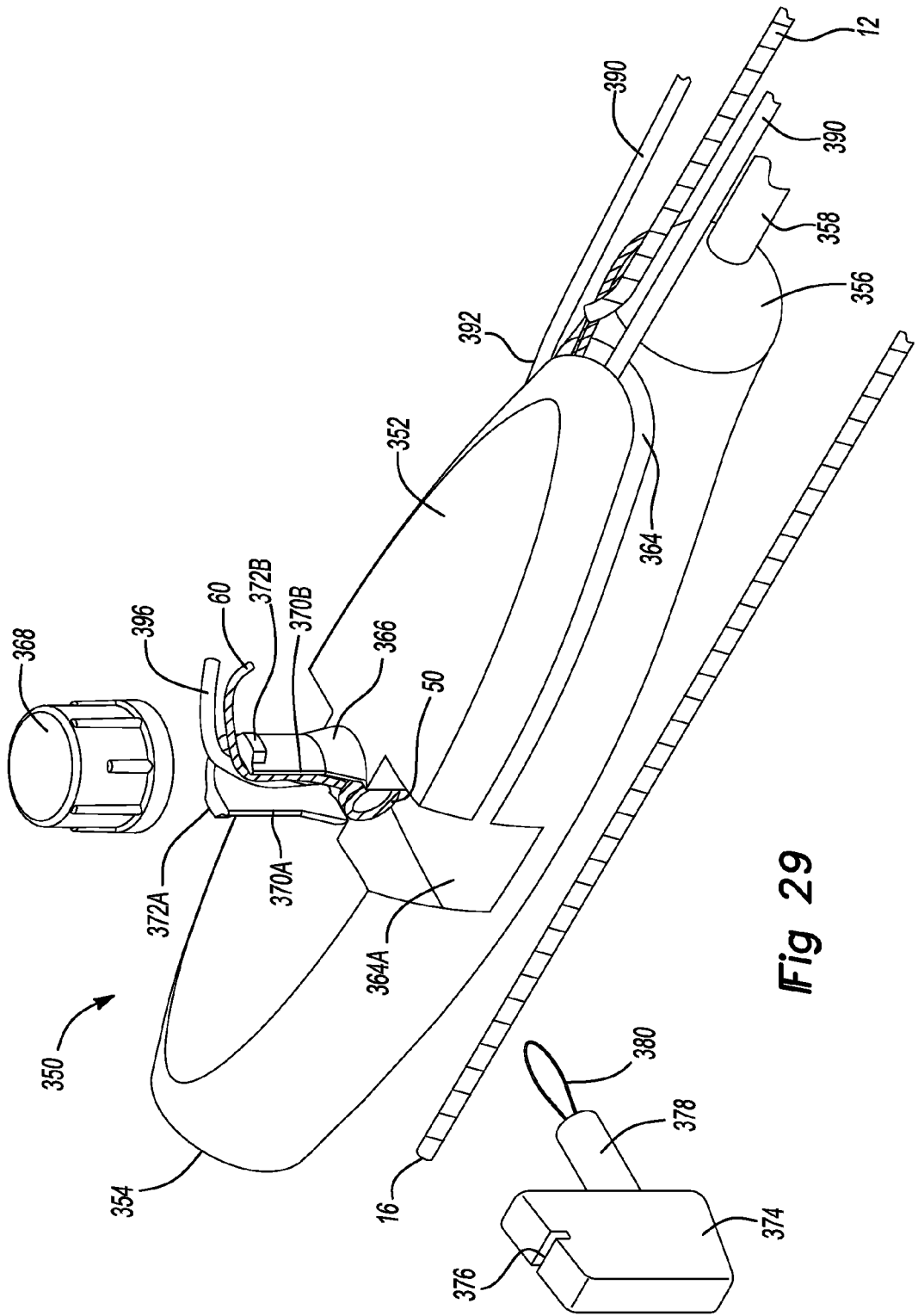
FIG. 29 is a perspective view of a handle of the insertion device of FIG. 28.

The handle 352 further includes a slot 364 that extends from one side of the handle to the other. The slot 364 provides a passageway for the knotless suture anchor device 10 to extend to flange 366, as further described herein. A cap 368 is configured to be releasably connected to the flange 366, to retain the second end 60 of the suture construct 14 connected to the handle 352, as further described herein. As illustrated in FIG. 29, the flange 366 includes a first flange edge 370A and a second flange edge 370B that is spaced apart from the first flange edge 370A to define a gap between the first and the second flange edges 370A and 370B. The flange 366 further includes a first tab 372A and a second tab 372B that are configured to cooperate with the cap 368 to secure the cap 368 to the flange 366.

The insertion device 350 further includes a pin 374. A slot 376 is defined within the pin 374. Extending from the pin 374 is a post 378. A loop 380 extends from the post 378. The pin 374 is removably connected to the handle 352 in a transverse portion 364A of the slot.

With continued reference to FIGS. 28 and 29, arrangement of the knotless suture anchor device 10 when coupled to the insertion device 350 will now be described. The device 10 is described for exemplary purposes only as any suitable retention device can be connected to the insertion device 350. The anchor 30 is positioned at the tip 360 between forks of the forked portion 362. The first portion 66 of the suture tail 12 extends towards the handle 352 and is seated within the slot 376 of the pin 374, which is seated in the transverse portion 364A of the slot 364. The second portion 68 of the suture tail 12 extends from the anchor 30 to the slot 364 and into the slot 364. The suture construct 14 connected to the second portion 68 is arranged such that the first adjustable suture loop 50 is seated within the transverse portion 364A of the slot 364 and the second end 60 of the suture construct 14 extends up through the flange 366 and out of the flange 366. The cap 368 is coupled to the flange 366 over the suture construct 14 proximate to the second end 60 to secure the suture construct 14 to the handle 352. The pin 374 is seated in the transverse portion 364A such that the post 378 extends through the first adjustable suture loop 50 and the loop 380 is on a side of the first adjustable suture loop 50.

To further retain the knotless suture anchor device 10 to the handle 352, the insertion device 350 can also include a retention strand 390. The retention strand 390 includes a first end 392 that is coupled to knob 394 of the handle 352. From the knob 394 the retention strand 390 extends to the tip 360 of the rod 358 and overlaps the anchor 30. From the anchor 30 the retention strand 390 extends into the slot 364 and to the flange 366. The retention strand 390 extends out through the flange and terminates at a second end 396 that is opposite to the first end 392. The cap 368 is secured to the flange 366 over the retention strand 390 to secure the portion of the retention strand 390 proximate to the second end 396 to the handle 352.

Figure 30:
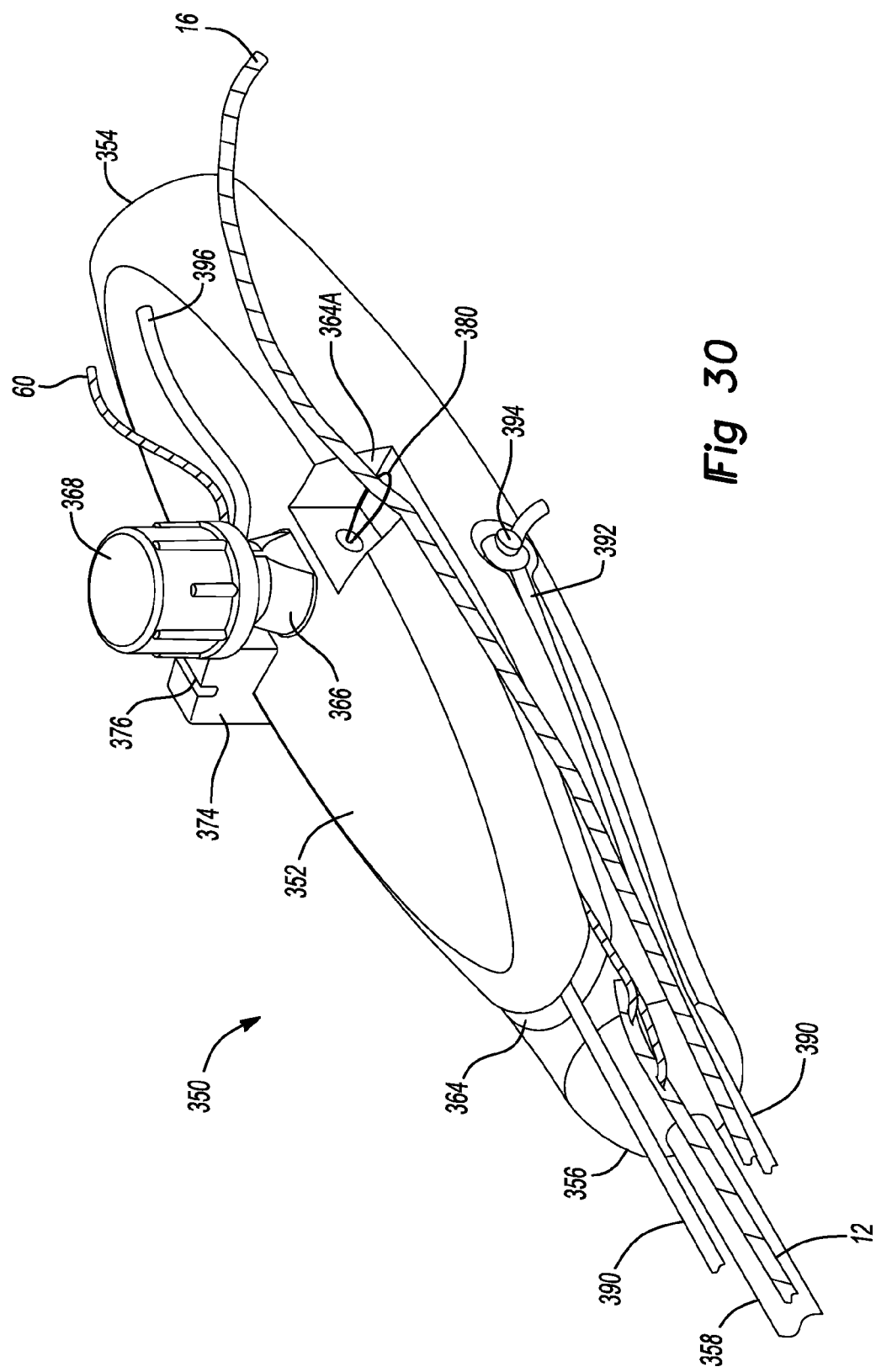
FIG. 30 is another perspective view of the handle of the insertion device of FIG. 28.
Figure 31:
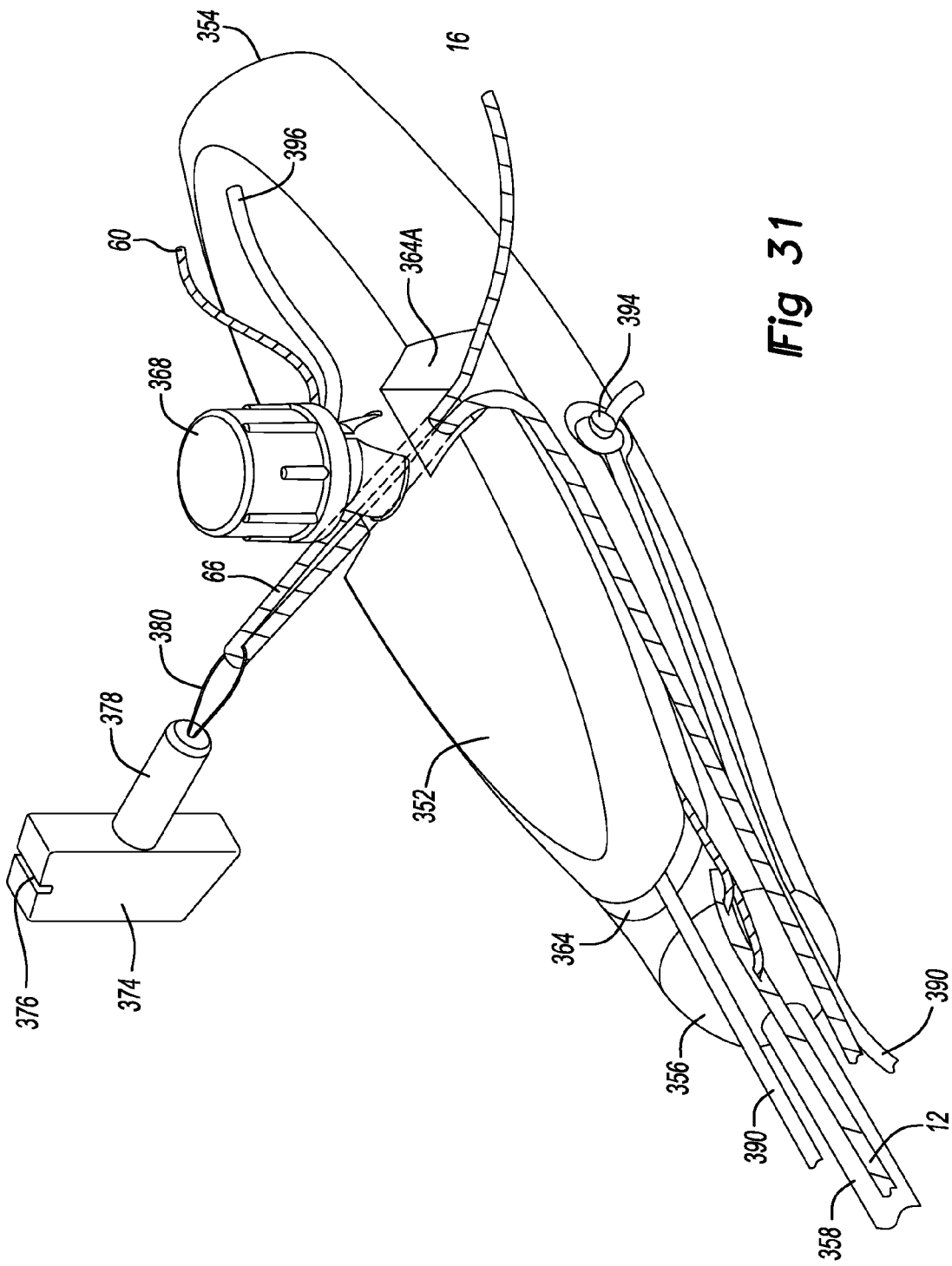
FIG. 31 is a perspective view of the handle of the insertion device of FIG. 28 showing a pin being withdrawn from the handle.
Figure 32:
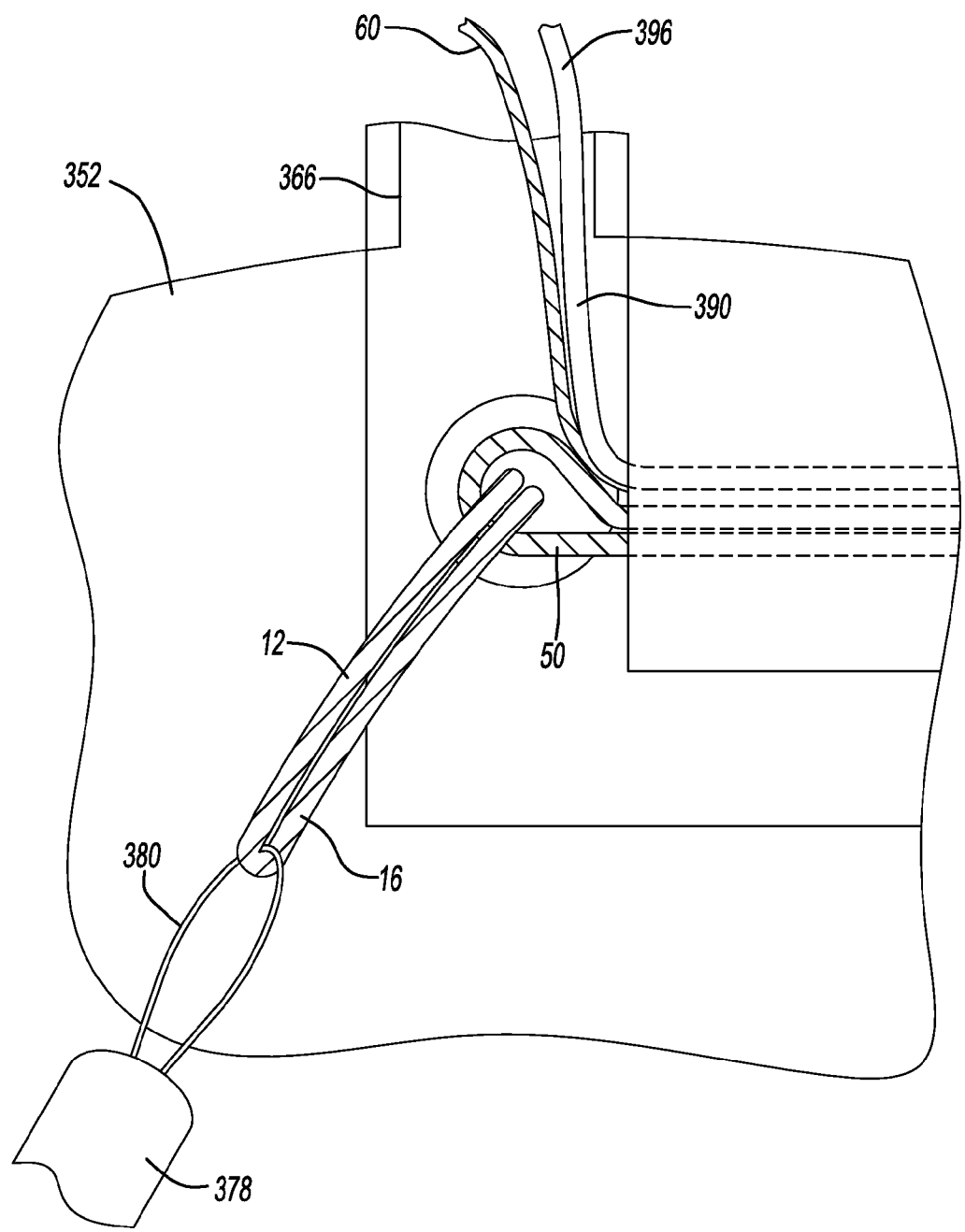
FIG. 32 illustrates the suture tail being passed through the first suture loop of the suture construct with the pin of FIG. 31.

With additional references to FIGS. 30-32, operation of the insertion device 350 will now be described. After the anchor 30 has been inserted into a hole formed in bone, the first portion 66 of the suture tail 12 is removed from within the slot 376 of the pin 374. The first end 16 of the suture tail 12, which is included with the first portion 66, is then inserted or passed through the loop 380 of the pin 374. The suture tail 12 is threaded through the first adjustable suture loop 50 by withdrawing the pin 374 from within the transverse portion 364A of the slot 364 and from the handle 352 altogether, as illustrated in FIGS. 31 and 32. To decouple the suture construct 14 from engagement with the handle 352, the cap 368 is removed. With the cap 368 removed, both the second end 396 of the retention strand 390 and the suture construct 14 can be decoupled from the handle 352 by pulling them out through the slot 364. The first end 392 of the retention strand 390 can be untied from the knob 394 or be cut proximate to the knob 394. The suture construct 14 can then be tightened as described above.

Use of the knotless suture anchor device 10 to repair torn labrum tissue 402 of a glenoid cavity 404 will now be described with reference to FIGS. 33-38. Repair of the labrum tissue 402 is described for exemplary purposes only because the knotless suture anchor device 10 can be used to repair any suitable tissue, such as an acetabular labrum. The knotless suture anchor device 10 is described as being mounted to the insertion device 202 described above and illustrated in FIGS. 14-24, but any suitable insertion device can be used, such as the insertion devices 302 and 350.

Figure 33:
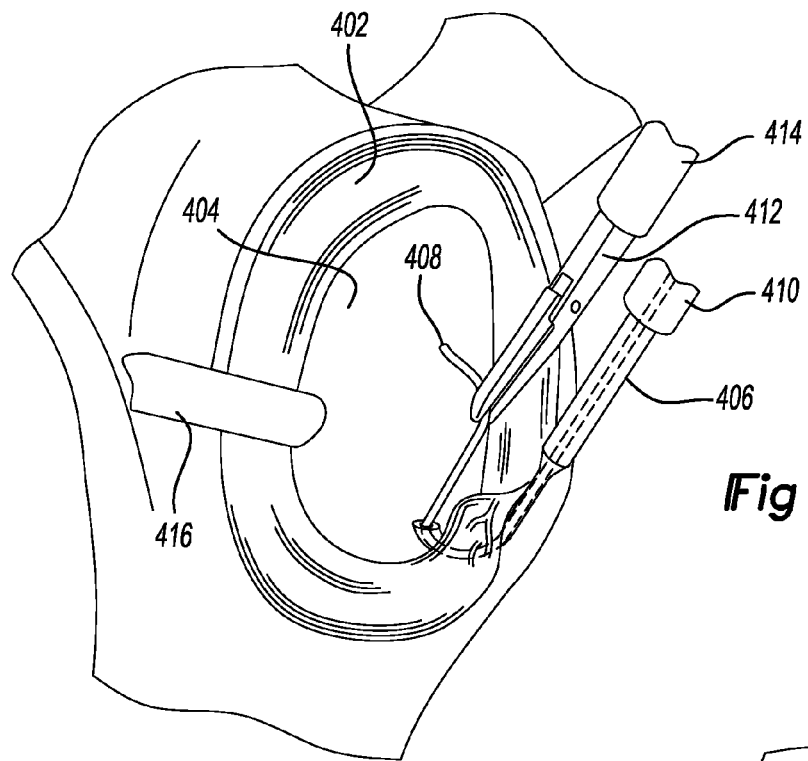
FIGS. 33-38 illustrate a method of repairing torn labrum tissue using the knotless suture anchor device of FIG. 1.

With initial reference to FIG. 33, a suture passer 406 with a suture passing strand 408 mounted thereto is inserted through a first cannula 410 underneath a torn portion of the labrum tissue 402. A grasper 412 is inserted through a second cannula 414. The grasper 412 is used to grasp the passing strand 408 and pull the passing strand 408 up from under the labrum tissue 402. The passer 406 is removed and another grasper (not shown) is inserted through the first cannula 410 to grasp the passing strand 408. The passing strand 408 is then pulled up through the first cannula 410. The first cannula 410 is positioned anteroinferior and the second cannula 414 positioned anterosuperior. To drain any excess fluid, a fluid cannula 416 can be introduced into the glenoid cavity 404

Figure 34:
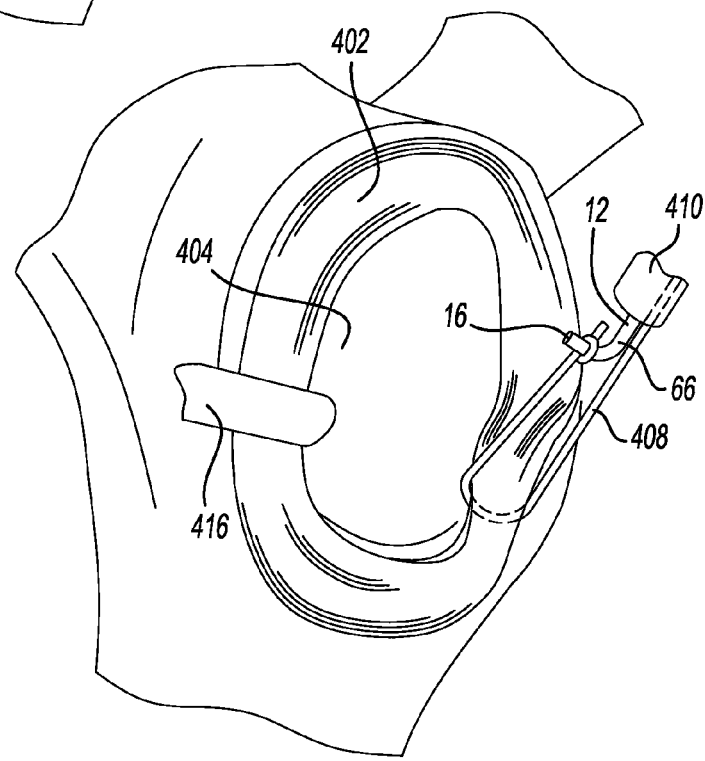
Figure 35:
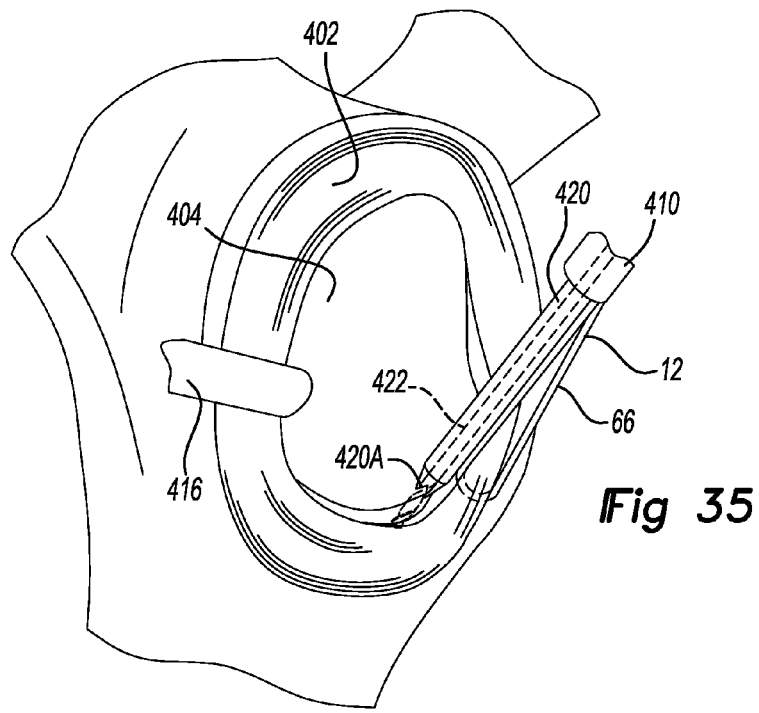
Figure 36:
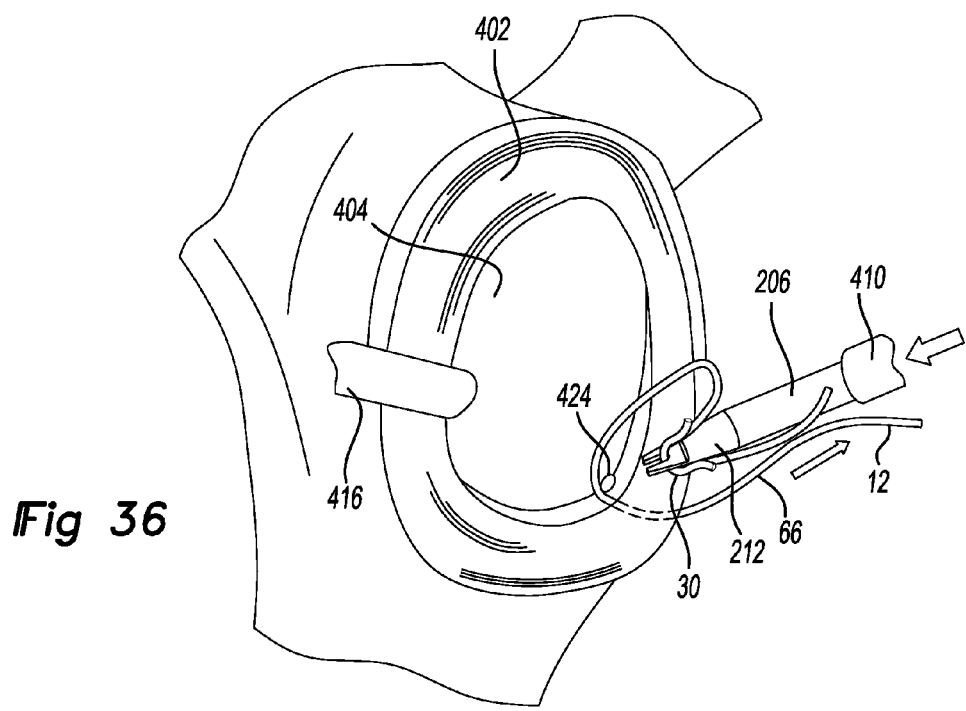

Outside of the joint space, the passing strand 408 is tied to the first portion 66 of the suture tail 12, which is detached from the insertion device 202 by unclipping the suture retention assembly 214 from the handle 204, as illustrated in FIG. 19, for example. As illustrated in FIG. 34, the passing strand 408 is pulled out of the first cannula 410 to draw the suture tail 12 into the glenoid cavity 404 and around the labrum tissue 402. FIG. 35 illustrates the first portion 66 of the suture tail 12 looped around the labrum tissue 402.

FIG. 35 also illustrates a drill guide 420, which includes teeth 420A at a distal end thereof configured to cut bone for example, inserted through the first cannula 410. The drill guide 420 is positioned superiorly to the suture tail 12 and a drill 422 is inserted therethrough to form a bone hole 424 in the glenoid cavity 404. The rod 206 of the insertion device 202 is inserted through the first cannula 410 to implant the anchor 30 within the bone hole 424, such as illustrated in FIG. 19 with respect to the anchor 30 being implanted in bone hole 110. Tension is maintained on the suture tail 12 by the surgeon as the anchor 30 is implanted. The anchor 30 can be implanted by impaction, such as by striking the distal end 210 of the handle 204 with a hammer. After the anchor is implanted, the rod 206 can be removed out from within the first cannula 410.

Figure 37:
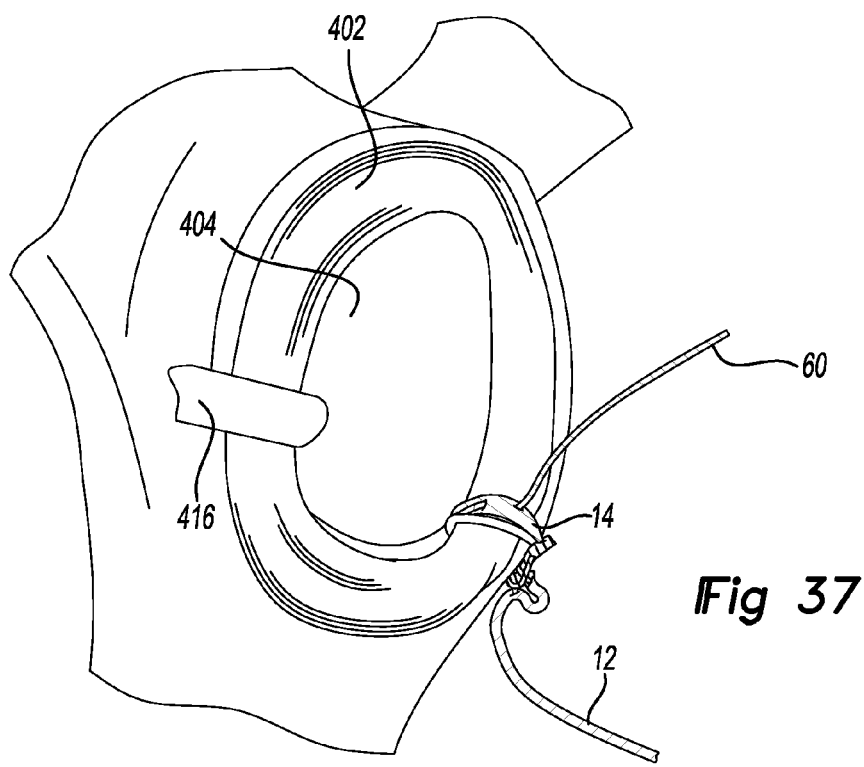
Figure 38:
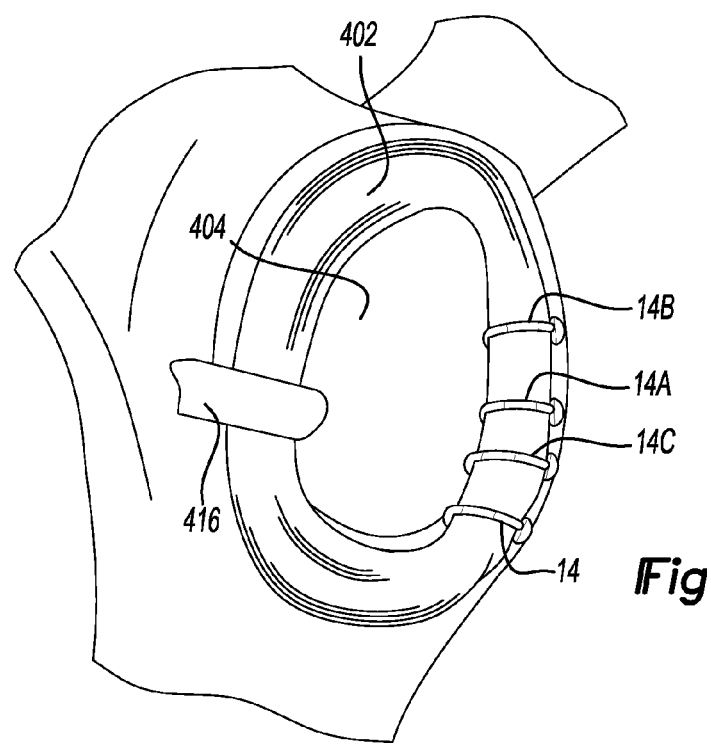

The suture tail 12 is then inserted through the first adjustable suture loop 50 by inserting the first end 16 thereof through the ring 238 of the passing device 218, as illustrated in FIG. 20. As illustrated in FIG. 21, the passing device 218 is pulled outward from the anchor 216 to place the suture retention assembly 214 in the second position. The first adjustable suture loop 50 is thus released from cooperation with the rim 230. The suture tail 12 is then pulled through the anchor 30 to advance the suture construct 14 to the labrum tissue 402 and around the labrum tissue 402, as illustrated in FIG. 37. The anchor 30 is underneath, and obstructed by, the labrum tissue 402 in FIG. 37, and thus not specifically shown. The second end 60 of the suture construct 14 extends out from the second cannula 414, and can be grasped by the surgeon to tighten the suture construct 14 onto the labrum tissue 402 at a desired tension. FIG. 38 illustrates the suture construct 14 secured onto the labrum tissue 402 at its final position. Additional suture constructs 14A, 14B, and 14C can also be fastened to the labrum tissue in the same manner as described above to further secure the labrum tissue 402 to the glenoid cavity 404.

Although the insertion tools 202, 302, 350 are illustrated and described above as including the anchor 30, the anchor need not be included. For example, any of the insertion tools 202, 302, and 350 can be used to insert the suture tail 12 and suture construct 14 through the first tissue portion 140A and the second tissue portion 140B to merge the first and the second tissue portions 140A and 140B together, which does not involve use of the anchor 30.

As described above, the suture construct 14 allows a first tissue to be coupled to a second tissue without the need to tie knots, which makes surgery, particularly arthroscopic procedures, easier and faster. In some instances, by eliminating the need to tie knots the suture construct 14 may make the connection between first and second tissues more reliable. The suture tail 10 facilitates passing the suture construct through or around tissue, particularly during arthroscopic procedures. The suture tail 10 may be passed through or around the tissue before or after the anchor 30 has been implanted, which can further expedite and make arthroscopic procedures less complicated.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for coupling tissue with a flexible member including a tail and a self-locking construct coupled to the tail, the self-locking construct including a first loop and an adjustable second loop coupled thereto, the method comprising:
    implanting an anchor in bone, the anchor slidably mounted to the tail;
    positioning the tail relative to the tissue;
    inserting an end of the tail through the first loop;
    passing the tail through the first loop, pulling the adjustable second loop into the anchor, and positioning the self-locking construct relative to the tissue; and
    tightening the self-locking construct against the tissue by pulling on an end of the self-locking construct,
    wherein positioning the tail includes positioning the tail such that the tail passes through a first tissue portion and a second tissue portion to arrange the self-locking construct across the first tissue portion and the second tissue portion, and couple the first tissue portion to the second tissue portion.

2. The method of claim 1, further comprising positioning the tail relative to the tissue one of before or after implanting the anchor in bone.

3. The method of claim 1, wherein positioning the tail includes positioning the tail such that the tissue is between a first portion of the tail and a second portion of the tail, and wherein positioning the self-locking construct includes wrapping the self-locking construct around the tissue.

4. The method of claim 1, further comprising tightening the first loop to the adjustable second loop by sliding a first body of the self-locking construct along the self-locking construct to decrease the size of, and adjust, the first loop, and tensioning the adjustable second loop by pulling on the end of the self-locking construct to move the anchor from an expanded position to a collapsed position by flexing the anchor to secure the anchor within the bone.

5. The method of claim 1, wherein the tissue is labrum tissue and the method further includes:
    passing a shuttling strand under the tissue with a passer;
    pulling the shuttling strand from under the tissue with a grasper;
    pulling the shuttling strand through a portal and coupling the shuttling strand to the tail;
    pulling the tail under the tissue with the shuttling strand and arranging the tail such that the tissue is generally between a first portion and a second portion of the tail;
    forming a bone hole in the glenoid with a drill, the bone hole formed near the tail;
    implanting the anchor in the bone hole using an insertion tool;
    passing the tail through the first loop outside of the body;
    pulling the tail out of the joint space and entirely through the first loop; and
    pulling the end of the self-locking construct to tighten the self-locking construct onto the labrum tissue.

6. A method for coupling tissue with a flexible member including a tail and a self-locking construct coupled to the tail, the self-locking construct including a first loop and a second adjustable loop coupled thereto, the method comprising:
    implanting an anchor in bone, the anchor slidably mounted to the tail;
    passing the tail through the tissue;
    inserting an end of the tail through the first loop;
    passing the tail through the first loop, pulling the second adjustable loop into the anchor, and positioning the self-locking construct through the tissue; and
    tightening the self-locking construct against the tissue by pulling on an end of the self-locking construct.

7. The method of claim 6, further comprising implanting the anchor one of before or after passing the tail through the tissue.

8. The method of claim 6, further comprising passing the anchor through the tissue prior to implanting the anchor in the bone.

9. The method of claim 6, further comprising passing the tail through the tissue from an inner surface to an outer surface of the tissue.

10. The method of claim 6, further comprising passing the tail through the tissue twice, such that the self-locking construct extends through the tissue in a first direction and returns through the tissue in a second direction.

11. The method of claim 6, wherein the anchor is a first flexible anchor, the method further comprising implanting a second flexible anchor in the bone, the second flexible anchor slidably mounted to the tail.

12. The method of claim 11, further comprising implanting the first flexible anchor in the bone medial to the second flexible anchor.

13. The method of claim 11, further comprising implanting a third flexible anchor in the bone, the third flexible anchor slidably mounted to the tail.

14. The method of claim 6, further comprising passing the tail through rotator cuff tissue.

15. The method of claim 6, further comprising tensioning the tissue in the lateral direction by pulling on the end of the self-locking construct.

16. A method for coupling tissue with a flexible member including a tail and a self-locking construct coupled to the tail, the self-locking construct including a first loop and a second adjustable loop coupled thereto, the method comprising:
   passing the tail through a first tissue and a second tissue;
   inserting an end of the tail through the first loop;
   passing the tail through the first loop, pulling the second adjustable loop into and across both the first tissue and the second tissue; and
   tightening the self-locking construct against both the first tissue and the second tissue by pulling on an end of the self-locking construct to couple the first tissue to the second tissue.

17. The method of claim 16, wherein the first tissue and the second tissue are separated rotator cuff tissue.

18. The method of claim 16, wherein the first loop is adjustable, and further comprising closing the first loop onto the second adjustable loop of the self-locking construct to secure the first loop to the second adjustable loop and retain the first tissue in contact with the second tissue.

19. The method of claim 18, further comprising passing the entire tail through the first loop and pulling the end of the suture construct to decrease the size of the second adjustable loop.

* * * * *